United States Patent
Tal

(10) Patent No.: US 11,419,634 B2
(45) Date of Patent: Aug. 23, 2022

(54) CAUSING ISCHEMIA IN TUMORS

(71) Applicant: Empress Medical, Inc., Wilmington, DE (US)

(72) Inventor: Michael Gabriel Tal, Tel Aviv (IL)

(73) Assignee: Empress Medical, Inc., Wilmington, DE (US)

( * ) Notice: Subject to any disclaimer, the term of this patent is extended or adjusted under 35 U.S.C. 154(b) by 320 days.

(21) Appl. No.: 16/539,800

(22) Filed: Aug. 13, 2019

(65) Prior Publication Data
US 2020/0054358 A1 Feb. 20, 2020

Related U.S. Application Data

(60) Provisional application No. 62/719,177, filed on Aug. 17, 2018.

(51) Int. Cl.
*A61B 17/42* (2006.01)
*A61B 17/12* (2006.01)
(Continued)

(52) U.S. Cl.
CPC ........ *A61B 17/42* (2013.01); *A61B 17/00234* (2013.01); *A61B 17/0401* (2013.01);
(Continued)

(58) Field of Classification Search
CPC .............. A61B 17/42; A61B 17/12009; A61B 2017/0496; A61B 2017/00358; A61B 17/1327; A61B 2017/0417–0419
See application file for complete search history.

(56) References Cited

U.S. PATENT DOCUMENTS 5,083,570 A * 1/1992 Mosby ............... A61B 17/3403
604/116
5,116,340 A 5/1992 Songer et al.
(Continued)

FOREIGN PATENT DOCUMENTS

CA 2634284 A1 7/2007
CN 203763237 U 8/2014
(Continued)

OTHER PUBLICATIONS

International Search Report and Written Opinion, dated Feb. 14, 2020, in International Application No. PCT/US2019/064030.
International Search Report and Written Opinion dated Oct. 7, 2019 in International Patent Application No. PCT/US2019/046384.
Milosevic et al. (1999) "The relationship between elevated interstitial fluid pressure and blood flow in tumors—a bioengineering analysis".
(Continued)

*Primary Examiner* — Darwin P Erezo
*Assistant Examiner* — Brigid K Byrd
(74) *Attorney, Agent, or Firm* — Veros Legal Solutions, LLP

(57) ABSTRACT

A method for treating a tumor at least partially within an organ in a subject's body. The method comprises volumetrically compressing the tumor to increase a pressure within the tumor above a threshold level to cause ischemia of the tumor; and maintaining the pressure above the threshold level for a period sufficient to cause necrosis in the tumor. The method may include passing a tension member within the organ around a predetermined volumetric region encompassing at least a portion of the tumor. The method may include tightening the tension member to cause compression of the volumetric region, thereby directly increasing a pressure within the tumor. The method may include maintaining the increased pressure such that most or all tissues of the tumor undergo ischemia and/or necrosis resulting directly from the compression caused by the tightened tension member.

28 Claims, 28 Drawing Sheets

(51) Int. Cl.
*A61B 17/132* (2006.01)
*A61B 17/00* (2006.01)
*A61B 17/04* (2006.01)
*A61B 17/062* (2006.01)

(52) U.S. Cl.
CPC ...... *A61B 17/0469* (2013.01); *A61B 17/0482* (2013.01); *A61B 17/062* (2013.01); *A61B 17/12009* (2013.01); *A61B 17/1327* (2013.01); *A61B 2017/00022* (2013.01); *A61B 2017/00358* (2013.01); *A61B 2017/0454* (2013.01); *A61B 2017/0496* (2013.01); *A61B 2017/4216* (2013.01)

(56) References Cited

U.S. PATENT DOCUMENTS

| | | |
|---|---|---|
| 5,281,238 A | 1/1994 | Chin et al. |
| 5,417,700 A | 5/1995 | Egan |
| 5,439,467 A | 8/1995 | Benderev et al. |
| 5,447,512 A | 9/1995 | Wilson et al. |
| 5,484,399 A | 1/1996 | DiResta et al. |
| 5,611,357 A * | 3/1997 | Suval ............... A61B 17/12009 128/898 |
| 5,735,289 A | 4/1998 | Pfeffer et al. |
| 5,788,709 A | 8/1998 | Riek et al. |
| 5,792,151 A | 8/1998 | Heck et al. |
| 5,846,180 A | 12/1998 | Kulisz et al. |
| 5,957,936 A * | 9/1999 | Yoon ............... A61B 17/12013 606/144 |
| 6,102,920 A | 8/2000 | Sullivan et al. |
| 6,159,234 A | 12/2000 | Bonutti et al. |
| 6,254,601 B1 | 7/2001 | Burbank et al. |
| 6,471,715 B1 | 10/2002 | Weiss |
| 6,546,933 B1 | 4/2003 | Yoon |
| 6,550,482 B1 | 4/2003 | Burbank et al. |
| 6,602,251 B2 | 8/2003 | Burbank et al. |
| 6,605,097 B1 | 8/2003 | Lehe et al. |
| 6,659,105 B2 | 12/2003 | Burbank et al. |
| 6,764,488 B1 | 7/2004 | Burbank et al. |
| 6,905,506 B2 | 6/2005 | Burbank et al. |
| 6,936,048 B2 | 8/2005 | Hurst |
| 7,122,011 B2 | 10/2006 | Clifford et al. |
| 7,207,996 B2 | 4/2007 | Burbank et al. |
| 7,223,279 B2 | 5/2007 | Burbank et al. |
| 7,229,465 B2 | 6/2007 | Burbank et al. |
| 7,338,502 B2 | 3/2008 | Rosenblatt |
| 7,354,444 B2 | 4/2008 | Burbank et al. |
| 7,594,890 B2 | 9/2009 | Burbank et al. |
| 7,662,128 B2 | 2/2010 | Salcudean et al. |
| 7,771,357 B2 | 8/2010 | Burbank et al. |
| 7,842,050 B2 | 11/2010 | Diduch et al. |
| 7,875,036 B2 | 1/2011 | Burbank et al. |
| 7,883,475 B2 | 2/2011 | Dupont et al. |
| 8,137,372 B2 | 3/2012 | Kondoh et al. |
| 8,298,145 B2 | 10/2012 | Deckman et al. |
| 8,357,176 B2 | 1/2013 | Gross |
| 8,361,093 B2 | 1/2013 | Wright |
| 8,460,322 B2 | 6/2013 | Burg et al. |
| 8,528,563 B2 | 9/2013 | Gruber |
| 8,535,336 B2 | 9/2013 | Trovato |
| 8,568,385 B2 | 10/2013 | McIntyre |
| 8,574,253 B2 | 11/2013 | Gruber et al. |
| 8,647,367 B2 | 2/2014 | Kassab et al. |
| 8,795,295 B2 | 8/2014 | Sauer |
| 8,808,313 B2 | 8/2014 | Thorne et al. |
| 8,858,528 B2 | 10/2014 | Sicvol |
| 8,951,274 B2 | 2/2015 | Adams et al. |
| 9,095,366 B2 | 8/2015 | Sullivan et al. |
| 9,144,428 B2 | 9/2015 | Binmoeller et al. |
| 9,174,020 B2 | 11/2015 | Allen et al. |
| 9,198,664 B2 | 12/2015 | Fung et al. |
| 9,282,988 B2 | 3/2016 | Goshayeshgar |
| 9,289,205 B2 | 3/2016 | Rohl et al. |
| 9,301,770 B2 | 4/2016 | Gruber |
| 9,339,288 B2 | 5/2016 | Sullivan et al. |
| 9,392,935 B2 | 7/2016 | Adams et al. |
| 9,539,019 B2 | 1/2017 | Sullivan et al. |
| 9,808,237 B2 | 11/2017 | Murray et al. |
| 9,808,240 B2 | 11/2017 | Parsons et al. |
| 9,820,794 B2 | 11/2017 | Ott et al. |
| 9,936,956 B2 | 4/2018 | Fung et al. |
| 10,085,763 B2 | 10/2018 | Binmoeller et al. |
| 10,085,764 B2 | 10/2018 | Binmoeller et al. |
| 10,130,389 B2 | 11/2018 | Sullivan et al. |
| 10,143,475 B2 | 12/2018 | Ibrahim et al. |
| 2001/0047152 A1 | 11/2001 | DiResta et al. |
| 2002/0087178 A1 | 7/2002 | Nobles et al. |
| 2002/0124853 A1 * | 9/2002 | Burbank ............... A61B 17/42 128/898 |
| 2002/0147456 A1 | 10/2002 | Diduch et al. |
| 2004/0010273 A1 | 1/2004 | Diduch et al. |
| 2004/0097962 A1 | 5/2004 | Burbank et al. |
| 2004/0127915 A1 * | 7/2004 | Fleenor ............ A61B 17/06004 606/144 |
| 2004/0202694 A1 | 10/2004 | Burbank et al. |
| 2005/0182433 A1 | 8/2005 | Nady |
| 2005/0245947 A1 * | 11/2005 | Harmanli ............... A61B 17/02 606/157 |
| 2006/0178698 A1 | 8/2006 | McIntyre et al. |
| 2006/0265042 A1 * | 11/2006 | Catanese, III ...... A61B 17/0625 623/1.11 |
| 2006/0276808 A1 | 12/2006 | Arnal et al. |
| 2006/0276871 A1 * | 12/2006 | Lamson ........... A61B 17/06109 623/1.11 |
| 2006/0287658 A1 | 12/2006 | Mujwid et al. |
| 2007/0038229 A1 | 2/2007 | Torre et al. |
| 2007/0225702 A1 | 9/2007 | Kaouk |
| 2008/0114382 A1 | 5/2008 | Mujwid et al. |
| 2008/0200939 A1 | 8/2008 | MacLean et al. |
| 2009/0043295 A1 | 2/2009 | Arnal et al. |
| 2009/0054916 A1 | 2/2009 | Meier et al. |
| 2009/0062599 A1 | 3/2009 | Brizzolara |
| 2009/0149808 A1 | 6/2009 | Hansen et al. |
| 2009/0222025 A1 | 9/2009 | Catanese et al. |
| 2010/0198235 A1 | 8/2010 | Pierce et al. |
| 2011/0071551 A1 | 3/2011 | Singhatat et al. |
| 2011/0093009 A1 | 4/2011 | Fox |
| 2011/0106107 A1 * | 5/2011 | Binmoeller ......... A61B 17/1285 606/139 |
| 2011/0166514 A1 | 7/2011 | Trovato et al. |
| 2011/0224596 A1 | 9/2011 | Flaherty et al. |
| 2011/0251455 A1 | 10/2011 | Popovic |
| 2011/0256225 A1 | 10/2011 | Ghoroghchian et al. |
| 2011/0295199 A1 | 12/2011 | Popovic et al. |
| 2012/0093716 A1 | 4/2012 | Jennische et al. |
| 2012/0123448 A1 | 5/2012 | Flom et al. |
| 2012/0271230 A1 | 10/2012 | Amal et al. |
| 2013/0018385 A1 | 1/2013 | Keene et al. |
| 2013/0090526 A1 | 4/2013 | Suzuki et al. |
| 2013/0158578 A1 | 6/2013 | Ghodke et al. |
| 2013/0184680 A1 | 7/2013 | Brewer et al. |
| 2013/0324986 A1 | 12/2013 | Ott et al. |
| 2014/0271612 A1 | 9/2014 | Leppert et al. |
| 2014/0276913 A1 | 9/2014 | Tah et al. |
| 2014/0276979 A1 | 9/2014 | Sauer et al. |
| 2014/0276981 A1 | 9/2014 | Hendricksen et al. |
| 2014/0364835 A1 | 12/2014 | Allen et al. |
| 2014/0378963 A1 | 12/2014 | Batchelor et al. |
| 2015/0094739 A1 | 4/2015 | Norton et al. |
| 2015/0250476 A1 | 9/2015 | Feezor et al. |
| 2016/0120549 A1 | 5/2016 | Fung et al. |
| 2016/0120647 A1 | 5/2016 | Rogers et al. |
| 2016/0278781 A1 * | 9/2016 | Fung ................... A61B 90/361 |
| 2016/0296244 A1 | 10/2016 | Thomas et al. |
| 2016/0346000 A1 | 12/2016 | Abreu |
| 2016/0348769 A1 | 12/2016 | Siegal |
| 2017/0007259 A1 | 1/2017 | Kimura et al. |
| 2017/0119455 A1 | 5/2017 | Johnson et al. |
| 2017/0128062 A1 | 5/2017 | Eguchi et al. |
| 2017/0360706 A1 | 12/2017 | Ghoroghchian |
| 2018/0008250 A1 | 1/2018 | Joseph |
| 2018/0028178 A1 | 2/2018 | Murray et al. |
| 2018/0228486 A1 | 8/2018 | Ravikumar et al. |

(56) References Cited

U.S. PATENT DOCUMENTS

| | | |
|---|---|---|
| 2018/0310941 A1 | 11/2018 | Fung et al. |
| 2018/0344312 A9 | 12/2018 | Diduch et al. |
| 2019/0000497 A1 | 1/2019 | Binmoeller et al. |
| 2019/0117229 A1 | 4/2019 | Ibrahim et al. |

FOREIGN PATENT DOCUMENTS

| | | |
|---|---|---|
| DE | 4317328 C2 | 8/1996 |
| EP | 0669101 A1 | 8/1995 |
| EP | 1967146 A2 | 9/2008 |
| WO | 03034926 A1 | 5/2003 |
| WO | 2006137051 A1 | 12/2006 |
| WO | 2016007973 A3 | 3/2016 |
| WO | 2017083694 A1 | 5/2017 |
| WO | 2021202256 A1 | 10/2021 |

OTHER PUBLICATIONS

Shore (2000) "Capillaroscopy and the measurement of capillary pressure".

Boucher, et al., Interstitial Pressure Gradients in Tissue-isolated and Subcutaneous Tumors: Implications for Therapy1 Cancer Res Aug. 1, 1990; 50 (15): 4478-4484.

Jain RK. Determinants of tumor blood flow: a review. Cancer Res. May 15, 1988;48(10):2641-58. PMID: 3282647.

Stylianopoulos, et al., Coevolution of solid stress and interstitial fluid pressure in tumors during progression: implications for vascular collapse. Cancer Res. Jul. 1, 2013;73(13):3833-41. doi: 10.1158/0008-5472.CAN-12-4521. Epub Apr. 30, 2013. PMID: 23633490; PMCID: PMC3702668.

* cited by examiner

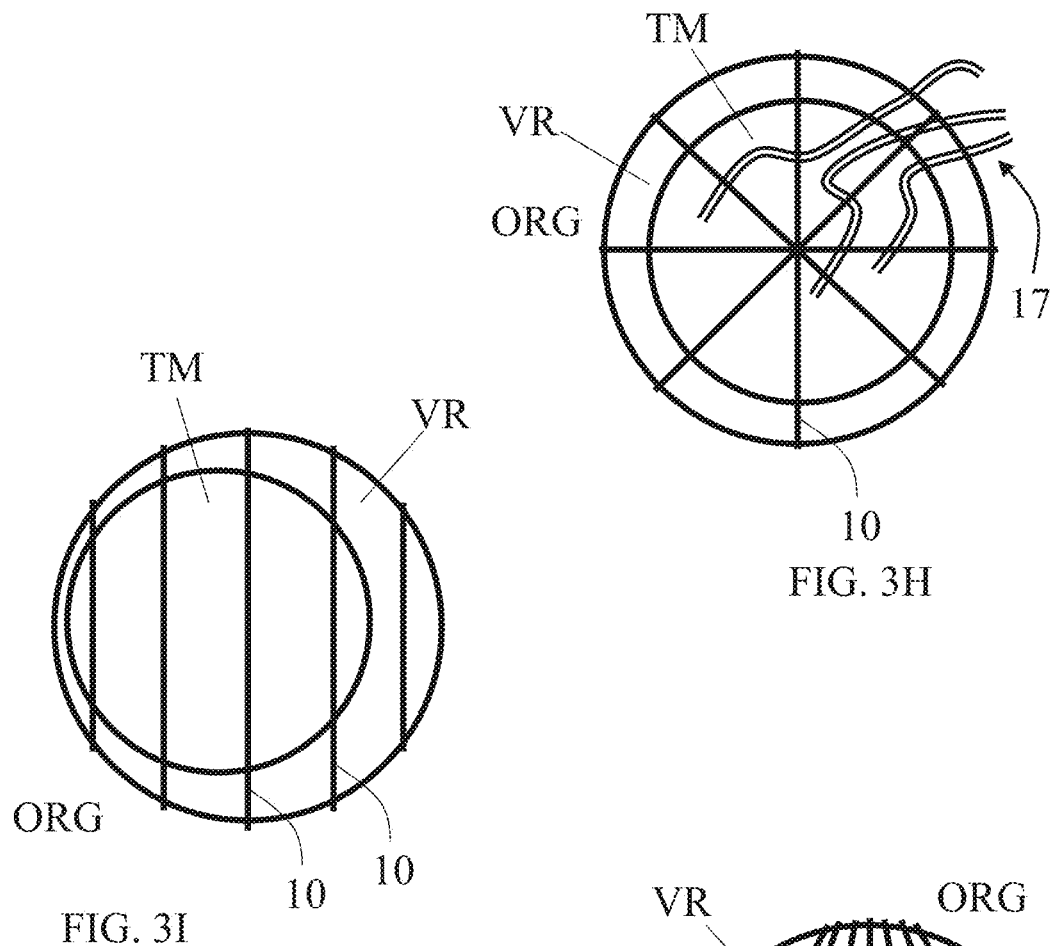
FIG. 3H
FIG. 3I
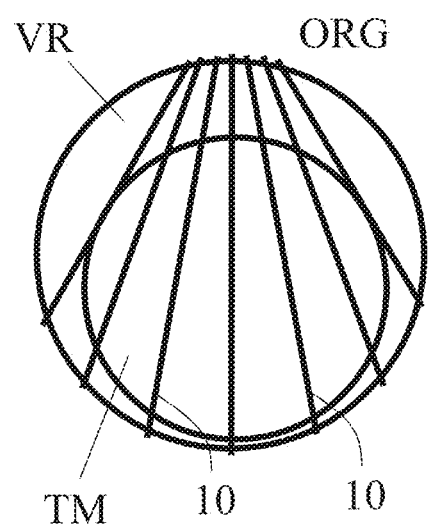
FIG. 3J
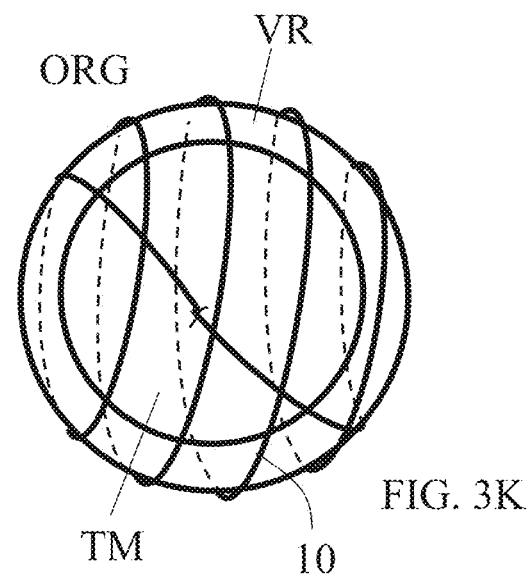
FIG. 3K

50

51 — Defining a volumetric region of a tumor

52 — passing tension member around the volumetric region

53 — tightening the tension member with a chosen tension force so as to affect radial compression of the volumetric portion for increasing pressure within the tumor

FIG. 4

CAUSING ISCHEMIA IN TUMORS

CROSS-REFERENCE TO RELATED APPLICATIONS

This application claims the benefit under 35 U.S.C. § 119(e) of U.S. Provisional Patent Application No. 62/719,177, filed on Aug. 17, 2018, titled AFFECTING ISCHEMIA TO TUMORS, the entire contents of which are hereby incorporated by reference herein.

FIELD OF THE INVENTION

The present disclosure relates to devices and methods for affecting blood supply to target tissues within a body of a subject, and more particularly, but not exclusively, to devices and methods (e.g., minimally invasive devices and methods) for suppressing tumors such as uterine fibroids by way of causing ischemia and/or necrosis thereto.

BACKGROUND OF THE INVENTION

A uterine fibroid (also referred to as a "myoma") is a benign tumor that is fed by the uterine artery and grows within the muscle tissue of the uterus. Myomas are solid fibrous tissue growing as a single nodule or in clusters and may range in size from about 1 mm to more than 20 cm in diameter. Myomas are the most frequently diagnosed tumor in the female pelvis and the most common reason for a woman to undergo hysterectomy. The prevailing symptoms of myomas include heavy menstrual bleeding, prolonged menstrual periods, pelvic pressure or pain and lower urinary tract symptoms (LUTS).

FIG. 1 illustrates an exemplary uterus with three types of fibroids. Uterine fibroids are classified by their location relative to the uterus, which affects the symptoms they may cause and how they can be treated. Fibroids that are inside the cavity of the uterus (submucous or submucosal fibroids) often cause bleeding between periods and severe cramping. Some submucous fibroids are submerged partially in the cavity and partially in the wall of the uterus. They too can cause heavy menstrual periods (menorrhagia), as well as bleeding between periods and are harder to remove in an hysteroscopic resection. Intramural fibroids grow in the wall of the uterus and can range in size from microscopic to larger than a grapefruit. Many intramural fibroids are not considered a risk to a patient's health until they reach a certain size. Subserous fibroids are found on the outside wall of the uterus and may even be connected to the uterus by a stalk (pedunculated fibroid). Known devices, systems, and methods for treating uterine fibroids suffer from a variety of limitations and drawbacks.

SUMMARY OF THE INVENTION

The present disclosure relates to devices and methods for affecting blood supply to target tissues within a body of a subject, and more particularly, but not exclusively, to devices and methods (e.g., minimally invasive devices and methods) for suppressing tumors such as uterine fibroids by way of causing ischemia and/or necrosis thereto.

In certain embodiments, there is provided a method for treating a tumor that is at least partially within an organ of a body of a subject. The method can comprise: passing a tension member within the organ between an entry opening and an exit opening, each opening being at a surface of the organ, and in close fit around a predetermined volumetric region that encompasses at least a portion of the tumor; tightening the tension member to cause compression of the volumetric region, thereby directly increasing a pressure within the tumor; and maintaining the increased pressure such that most or all tissues of the tumor undergo ischemia resulting directly from the compression caused by the tightened tension member.

In some embodiments, the passing includes winding the tension member and/or a plurality of additional tension members along separate paths around the volumetric region.

In some embodiments, the tightening includes tightening at least one of the tension member and/or the plurality of additional tension members to cause volumetric compression of the volumetric region.

In some embodiments, the volumetric region encompasses a majority or entirety of a volume of the tumor.

In some embodiments, the compression is maintained continuously at least until achieving necrosis in substantially all tissues of the tumor.

In some embodiments, the compression is maintained continuously for a period of no less than 1 hour.

In some embodiments, the tightening the tension member increases the pressure within the tumor to a first level and injures tissue within the volumetric region, the method further comprising: maintaining the tension member in a tightened state while tissue within the volumetric region that has been injured swells in response to the injury, wherein swelling of the tissue within the volumetric region increases the pressure within the tumor to a second level that exceeds the first level.

In some embodiments, the method further comprises passing the tension member along a predetermined passage line between the entry opening and the exit opening.

In some embodiments, the passage line projects across one or more blood vessels feeding the tumor, such that the tightening of the tension member directly causes occlusion of the one or more blood vessels.

In some embodiments, at least a portion of the tumor is situated intramurally within the organ, and wherein passing the tension member within the organ comprises passing the tension member through an intramural portion of the organ.

In some embodiments, the tumor is a uterine fibroid.

In some embodiments, the method further comprising creating a surgical access to the organ from outside the body, wherein at least one of the passing, tightening, and maintaining is performed via the surgical access.

In some embodiments, the method further comprising closing the surgical access while the tension member and the fastener remain within the body of the subject.

In some embodiments, the tightening includes or is followed by securing a first portion of the tension member protruding from the entry opening to a second portion of the tension member protruding from the exit opening, wherein the securing facilitates the maintaining.

In some embodiments, the securing is performed outside boundaries of the organ.

In some embodiments, the securing comprises attaching a fastener to the tension member.

In some embodiments, the securing comprises crimping the fastener to securely grasp the tension member.

In some embodiments, passing the tension member comprises advancing an end of the tension member through the exit opening, around the tumor, and through the entry opening such that a first portion of the tension member protrudes from the organ through the exit opening and a second portion of the tension member protrudes from the organ through the entry opening.

In some embodiments, the method further comprising: advancing an elongated member through the entry opening, around the tumor, and through the exit opening; and coupling the elongated member to the tension member prior to the passing the tension member, wherein the passing the tension member comprises withdrawing the elongated member through the exit opening, around the tumor, and through the entry opening while coupled to the tension member.

In some embodiments, the method further comprising: forming a passage around the volumetric region between the entry and exit openings, wherein the passing is performed after the forming and mostly or entirely within the passage and includes pulling the tension member towards the entry opening.

In some embodiments, the entry opening is located at a first location on or adjacent to the tumor and the exit opening is located at a second location on or adjacent to the tumor spaced from the first location, such that the tumor is located between the entry and exit openings.

In some embodiments, the tension member comprises a suture wire.

In some embodiments, the tightening comprises tightening the tension member and/or the plurality of additional tension members to collectively apply compressive force toward an interior of the tumor.

In some embodiments, the tightening comprises tightening the tension member to achieve a chosen tensioning force.

In some embodiments, the method further comprising measuring a tensioning force applied to the tension member, and/or measuring the pressure within the tumor, during the tightening.

In certain embodiments, there is provided a method for treating a tumor within a body of a subject. The method can comprise: deploying a plurality of windings of at least one tension member around the tumor, at least a portion of each of the windings being spaced apart from a portion of each adjacent winding; tightening the at least one tension member such that the plurality of windings collectively causes volumetric compression of the tumor; and maintaining the volumetric compression continuously to achieve ischemia in most or all tissues of the tumor.

In some embodiments, the tightening comprises tightening the at least one tension member to achieve a chosen tension force within the tumor and/or to achieve a chosen pressure within the tumor.

In some embodiments, the tightening comprises tightening the at least one tension member such that each of the plurality of windings applies compressive force toward an interior of the tumor.

In certain embodiments, there is provided a method that can comprise: volumetrically compressing a tumor within a patient to increase a pressure within the tumor above a threshold level that is sufficient to cause ischemia of the tumor; and maintaining the pressure above the threshold level for a period sufficient to permit at least a portion of the tumor to necrotize due to the ischemia.

In some embodiments, the method further comprising circumscribing the tumor with at least one device of foreign origin relative to the patient, wherein the volumetrically compressing the tumor and maintaining the pressure above the threshold level are achieved via the at least one device. In some embodiments, the volumetrically compressing the tumor comprises reducing a profile of the device around the tumor. In some embodiments, the volumetrically compressing comprises compressing the tumor along at least first and second lines of compression that extend around an outer surface of the tumor along different paths.

In some embodiments, the method further comprising encompassing the tumor with at least one tension member to define a three-dimensional shape around the tumor, wherein the volumetrically compressing the tumor comprises decreasing a size of the three-dimensional shape.

In some embodiments, decreasing the size of the three-dimensional shape is achieved by tightening the at least one tension member.

In some embodiments, the threshold level of the pressure is no less than 20 mmHg.

All technical or/and scientific words, terms, or/and phrases, used herein have the same or similar meaning as commonly understood by one of ordinary skill in the art to which the invention pertains, unless otherwise specifically defined or stated herein. Illustrative embodiments of methods (steps, procedures), apparatuses devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE DRAWINGS

Some embodiments are herein described, by way of example only, with reference to the accompanying drawings. With specific reference now to the drawings in detail, it is stressed that the particulars shown are by way of example and for purposes of illustrative description of some embodiments. In this regard, the description taken together with the accompanying drawings make apparent to those skilled in the art how some embodiments may be practiced.

In the drawings:

FIGS. 3A-3K schematically illustrate views of different exemplary fibroids treated using one or more tension members, according to some embodiments;

FIG. 4 shows a block diagram of an exemplary method for treating a tumor within a body of a subject, according to some embodiments;

DETAILED DESCRIPTION

Figure 1:
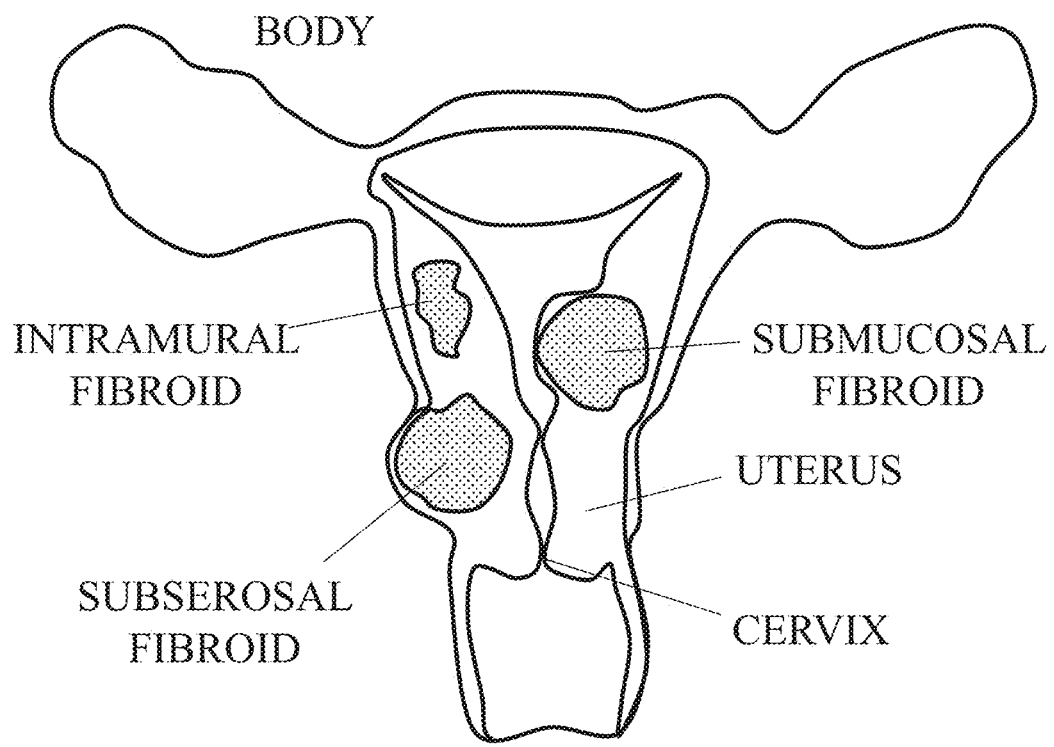
FIG. 1 schematically illustrates a frontal cross-sectional view of an illustrative female uterus having different types of fibroids growing therein.

Certain embodiments relate to devices and methods for affecting blood supply to target tissues within a body of a subject, and more particularly, but not exclusively, to devices and methods (e.g., minimally invasive devices and methods) for suppressing tumors such as uterine fibroids by way of causing ischemia and/or necrosis. One or more tension members are applied, according to certain illustrative methods described herein, around or through a target tumor, and are put under tensioning force in a manner that triggers, supports and/or induces tumor suppression.

In some embodiments, tension members are deployed and directly affect (cause) a continuous pressure within the tumor, including but not limited to pressure deriving from accumulated compression force causing radial and/or volumetric tissue compression of the tumor, interstitial pressure within the tumor and surrounding host tissue, and capillary blood pressure in the tumor and in proximity thereto, or any combination thereof, thus inhibiting blood flow into the tumor. Optionally, additionally or alternatively, tension members are deployed to pass over blood vessels nourishing the tumor and are configured and sufficiently taut so as to impinge the blood vessels and block blood flowing therethrough. Blocking blood supply to the tumor for several hours leads to fibroid ischemia and eventually to necrosis of the tumor cells.

In some embodiments, one or more (in any combination) of the following may be included in methods for triggering, supporting and/or inducing tumor suppression:

a) injecting a biocompatible material into the tumor, optionally having density greater than the original tumor density, such as hyaluronic acids, hydrogels, alginate, gelatin, BioGlue® Surgical Adhesive (available from CryoLife, of Kennesaw, Ga.), castor oil polyoxyethylene (POE), Pluronic® F127 hydrogel, collagen cells (Xenographt) or any other suitable material or combination of materials. To improve material absorption and for better insertion to the fibroid tissue, cuts/notches can be made in the fibroids and the material can be inserted to the notches directly;

b) directing energy to the tumor and/or surrounding tissue for elevating pressure in the tumor sufficiently to block blood supply to the tumor and cause ischemia in the tumor tissues. The energy may be delivered or maintained for a prolonged period sufficient to cause necrosis in all or most tumor tissues. Energy may include High intensity Focused Ultrasound, laser projection, direct or indirect thermal therapy or cryotherapy, or others.

c) applying mechanical pressure to the fibroid using tension members, for example by tying taut one or more sutures around and/or through the tumor. The sutures may be absorbable or permanent sutures. Additionally, or alternatively, springs, rods, bands, clips, clamps or any other force-applying elements may be used to increase the fibroid inner pressure; or d) exerting pressure directly on blood vessels present on the tumor surface, such as by encircling them with taught tension members, such as the ones described above, thereby blocking blood flow therein and thus contributing to the fibroid ischemia. The foregoing methods, which include material injection and mechanical pressure application, can be performed in any of an open surgical procedure, a laparoscopic surgical procedure or a vaginal approach procedure.

In some embodiments, in addition to causing increase in pressure within a tumor by tightening one or more tension members circumscribing the tumor, at least one tension member, and/or at least one other device implanted around, adjacent to the tumor, or together with the one or more tension members, can be applied to directly affect or facilitate treatment from a remote location directly in the tumor and/or surrounding host tissues. The at least one tension member and/or other device can be applied to mark certain points, lines or portion around the tumor for directing focused energy thereto. Alternatively or additionally, the at least one tension member and/or other device can be applied to deliver energy (for heat therapy or cryotherapy) and/or substance to the tumor and/or to its surrounding host tissues.

In some embodiments, at least some of the following steps are performed (not necessarily in the listed order) as part of a method for compressing a fibroid using taut tension members (e.g., sutures):

a) inserting a distal end of a suture delivery device into the abdominal cavity;

b) inserting a first needle (outer tube) through the fibroid perimeter;

c) pushing a second (inner) needle through the first needle and around the fibroid;

d) transferring a suture through the second needle;

e) providing ends of the suture in the abdominal cavity;

f) optionally repeating steps "b" to "e" at different angles on the fibroid (e.g. approximately 30-, 45-, 60-, or 90-degree angular shifts of offsets between sutures); and g) pulling the sutures ends out of the body and performing extracorporeal tie for each of the sutures and tightening the suture on the uterus outer surface, optionally using a knot pusher.

In some embodiments, at least some of the following steps are performed (not necessarily in the listed order) as part of a method for compressing a fibroid using taut tension members (e.g., sutures):

a) inserting a distal end of a suture delivery device into the abdominal cavity;

b) inserting a first needle to the fibroid center through the uterus wall;

c) inserting a second needle through or around the fibroid perimeter;

d) transferring a suture along a path from the first needle to the second needle (or vice versa);

e) providing the suture ends in the abdominal cavity;

f) optionally repeating steps "c" to "e" at different angles on the fibroid (e.g. 60 degrees shift between sutures); and g) pulling the sutures ends out of the body and performing extracorporeal tie for each of the sutures and tightening the suture on the uterus outer surface, optionally using a knot pusher.

As described further below, the tension members (e.g., sutures) can be placed around entire volume of the tumor (e.g., fibroid), optionally including portions of other tissues that surround the tumor (e.g., uterine tissue), or around one or more smaller volumetric portions of the tumor. In some instances, it can be advantageous to surround the entire tumor (fibroid) and/or avoid passing a tension member through a tumor volume, as there can be a sharp increase in density when entering the fibroid and/or there may be risk that the tumor is cancerous, such that puncturing therethrough increases risk of cancer spreading to surrounding tissues and the blood system. Nevertheless, in some procedures, it can be advantageous to pass a tension member through the tumor, such as, for example, in anatomies imposing difficulties to fully encompass the tumor.

Figures 2A, 2B:
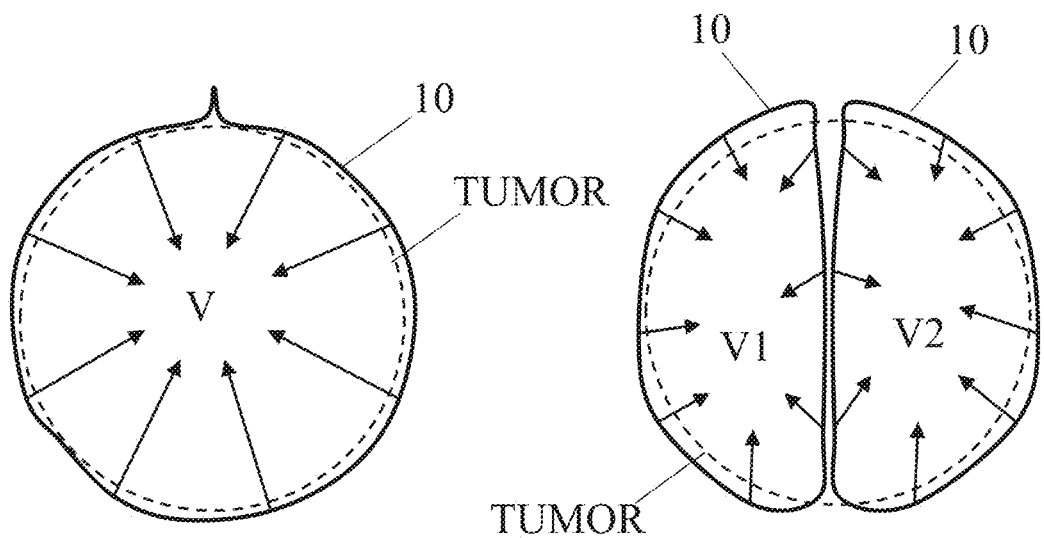
FIGS. 2A-2B schematically illustrate a cross-sectional view of an illustrative tumor being compressed—specifically, radially compressed—using one or more tension members, either about entire volume of the tumor (FIG. 2A) or about a number of volumetric portions of the tumor (FIG. 2B), according to some embodiments.

FIGS. 2A-2B schematically illustrate a cross-sectional view of an exemplary tumor being compressed using one or more tension members 10, which extend either about an entire volume V of the tumor (FIG. 2A) or about a number of volumetric portions V1 and V2 of the tumor (FIG. 2B). In the illustrated figures, each tension member 10 extends about a full periphery of the volume V (FIG. 2A) or the full periphery of the volumetric portion V1, V2 (FIG. 2B). Moreover, in the illustrated figures, each tension member 10 encompasses the volume V or volumetric portion V1, V2, respectively, substantially along a single plane—specifically, in FIGS. 2A and 2B, the plane corresponds with the plane of the drawing sheet.

With reference to FIG. 2A, in some embodiments, a plurality of tension members 10 may be employed, and each tension member 10 may extend about at least a portion of the volume V. As discussed more fully below, the additional tension members 10 may, in some instances, extend along different planes that are angularly offset from one or more of the other tension members 10. For example, additional tension members 10 may extend bout the volume V along planes that are at an angle to the plane of the drawing sheet for FIG. 2A. In various embodiments, when a plurality of tension members 10 are deployed, each one can encompass more than half of a periphery (e.g., circumference) of the tumor or of the volume V, more than two thirds the periphery (e.g., circumference), or substantially all or all of the periphery (e.g., circumference). Similarly, with reference to FIG. 2B, a plurality of tension members 10 may be employed about each of the volumetric portions V1, V2, and at least some of the additional tension members 10 can extend along or define planes that are angularly offset from the illustrated tension members 10.

When under a tensioning force, such as may result from, e.g., tightening, cinching, stretching, or otherwise tensioning the tension members 10, each tension member 10 can cause compression (e.g., radial compression) of the surrounded volume V or volumetric portion V1, V2. As further discussed below, the tensioning force may be chosen. For example, the tensioning force may be chosen, such as by being selected, preselected, predetermined, instructed (e.g., via instructions for use of a tensioning device), measured, and/or calculated.

A plurality of tension members can be arranged around a volume or volumetric portion of the tumor, such that the combined effect of all tension members thereto is compression towards an interior (e.g., toward the center) of the volume or tumor, or towards an interior (e.g., toward the center) of the volumetric portion. In some embodiments, each tension member 10 passes along a separate plane crossing or passing through the tumor. In some embodiments, tension members 10 are passed spaced apart from each other relative to a center of the tumor or the volume or volumetric portion, optionally evenly spaced apart; stated otherwise, the tension members 10 may be angularly offset from each other, and in some embodiments, the angular offsets are regular and/or of equal magnitude relative to each pair of adjacent tension members 10.

Figure 3A:
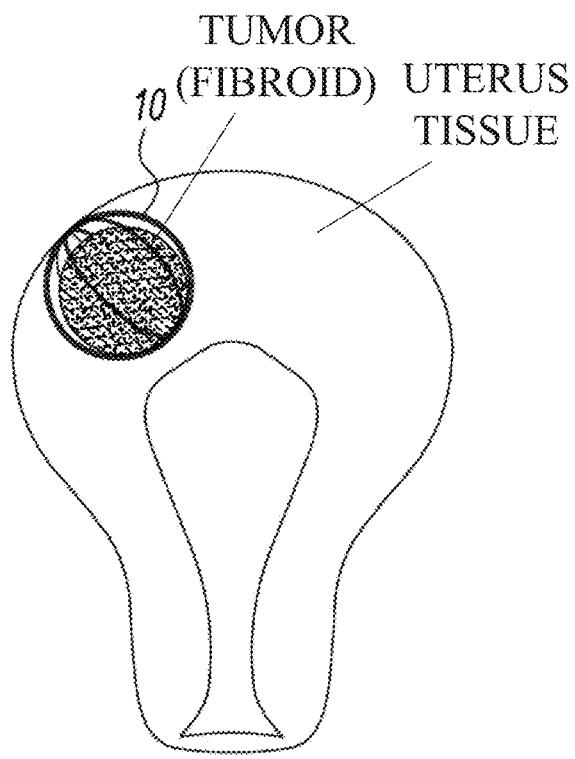

FIGS. 3A-3K schematically illustrate various views of different exemplary configurations of tumors (e.g., fibroids) formed within an organ (e.g., uterus) of a body of a subject, during or following treatment, according to some embodiments. In some embodiments, as shown in FIG. 3A, one or more tension members 10 may be provided (e.g., implanted) around the fibroid when passing partially or fully through uterus tissue (e.g., healthy uterus tissue) surrounding the fibroid, particularly in cases of intramural fibroids. In particular, FIG. 3A depicts three separate tension members 10, each of which extends about a full periphery of the tumor and also encircles a portion of healthy uterus tissue. Each of the three tension members 10 substantially defines a circular profile that is restricted to a single plane that passes through the tumor. The planes intersect at a line that passes through a center of the tumor. In the illustrated embodiment, each plane is angularly offset from each plane defined by the remaining two tension members by 60 degrees.

Figure 3B:
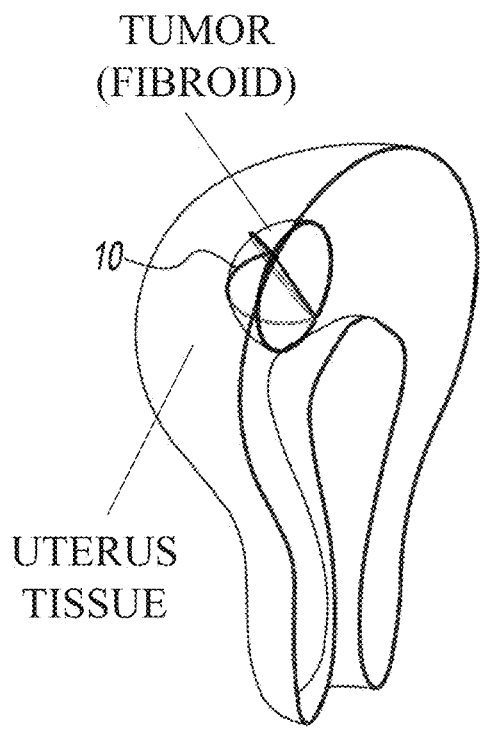
Figure 3C:
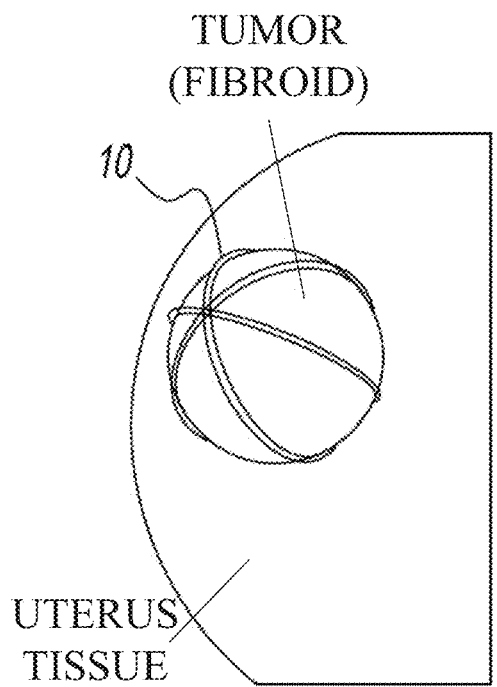
Figure 3D:
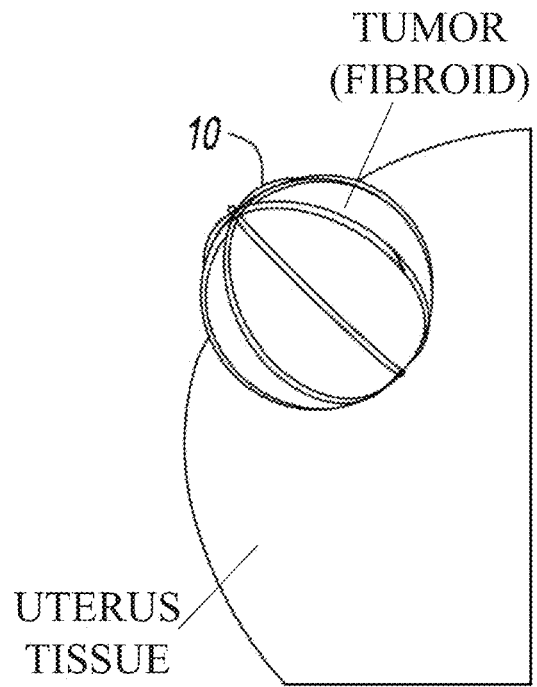

With reference to FIGS. 3B-3D, additionally or alternatively, one or more tension members 10 may be provided through the fibroid tissue, such as through its center or in proximity thereto. The number of tension members used can be determined according to need or tumor size or type, for example two, three, four or five tension members, or six tension members (FIG. 3C), or eight tension members (FIG. 3D), or more are contemplated.

Figure 3E:
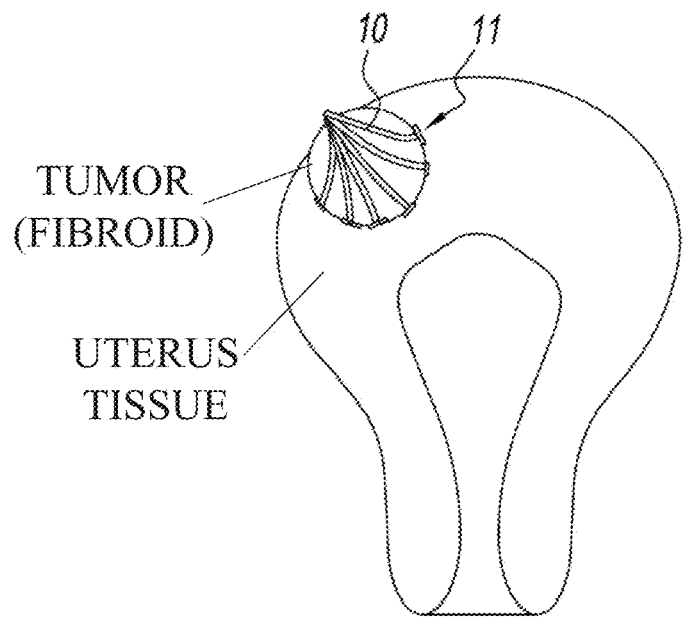
Figure 3F:
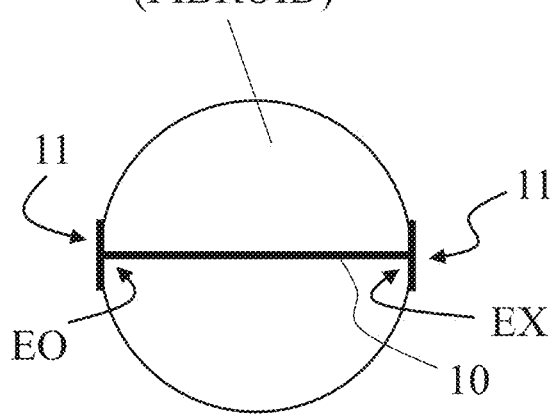

In some embodiments, one or more tension members 10 can be secured to the tumor and/or surrounding tissue by way of suturing or tying around the tumor or volumetric region (as shown in FIGS. 2A and 3A, for example) or a volumetric portion of the tumor (as shown in FIG. 2B, for example), or alternatively the one or more tension members 10 can be secured using anchors, such as anchors 11, as illustrated in FIG. 3E (showing use of a separate anchor 11 for each of six tension members 10) and FIG. 3F (showing a single tension member 10 extending taut between two anchors 11 at opposite sides of a tumor), for example.

In various embodiments, the tension members 10 that are secured via anchors 11, such as depicted in FIGS. 3E or 3F, can extend around an external periphery of the tumor. In other or further instances, at least a portion of the tension members 10 may extend through an interior portion of the tumor. The anchors 11 may serve as alternative system for securing the tension member(s) 10 to the tumor and maintaining tension in the tension members 10.

The tension member 10 can be configured in different forms and/or made from different materials. For example, in various embodiments, the tension members 10 can comprise wires or sutures (e.g., bioabsorbable or bioresorbable), strips, elongated fasteners (e.g., ratchet-type fasteners, such as a cable tie), or others.

Figure 3G:
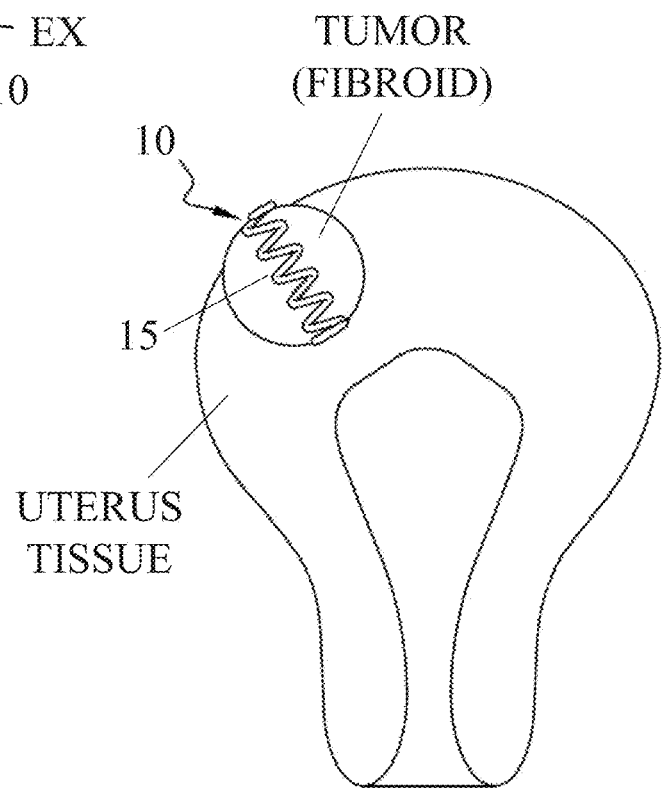

FIG. 3G shows another embodiment of a tension member 10, which is configured as a coiled implant 15. The implant 15 is formed as an elastically extendable or compressible helical band, configured to axially press (e.g., outwardly or inwardly) boundaries of the tumor in opposite directions. For example, in the illustrated embodiment, the implant 15 comprises a helical band (e.g., a compression spring) that has been expanded outwardly relative to a natural or resting orientation. This expansion gives rise to an inwardly directed bias. The implant 15 has been passed through a center of the tumor and the ends thereof have been affixed to the outer extremities of the tumor. Accordingly, the inwardly directed bias of the implant 15 tends to axially compress the tumor along a longitudinal or axial direction defined by the implant 15. Each end of the implant 15 is biased in opposite directions in this case, each end is biased inwardly in opposite directions toward a center of the tumor. In other embodiments, the implant may be secured to the tumor while in a compressed state, such that the implant 15 provides an outwardly directed bias in opposite directions along the longitudinal or axial direction. In some embodiments, one or more anchors 11 (such as depicted in FIGS. 3E. 3F) may be used to secure the ends of the implant 15 to a volumetric region and/or tumor to which the implant 15 is applied.

FIG. 3H depicts an arrangement similar to that of FIG. 3A, but with four tension members 10 rather than three, and depicts a top-plan view, rather than a perspective view. In particular, FIG. 3H shows a tension-member arrangement that provides a three-dimensional shape or compressive pattern that encompasses a tumor TM. In particular, a plurality of tension members 10 are placed around the volumetric region VR of an organ ORG that includes a tumor TM to define a three-dimensional shape. In the illustrated embodiment, the three-dimensional shape encompasses the tumor TM and a portion of healthy tissue of the organ ORG. In the illustrated embodiment, the shape is substantially spherical. The tension members 10 are tightened to decrease a size of the three-dimensional shape and thereby compress the volumetric region VR and the tumor TM.

In some embodiments, each tension member 10 is individually and sequentially placed around the tumor TM and tightened. That is, each tension member 10 is placed around the tumor TM and tightened prior to the placement and tightening of each remaining tension member 10. Accordingly, in some instances, the first-applied tension member 10 may define a substantially two-dimensional or planar shape, such as a circle or oval, and this shape may decrease in size due to tightening of the tension member 10. Thereafter, an additional tension member 10 may be placed round the tumor TM and tightened. When first placed around the tumor, the additional tension member 10 may, in cooperation with the first-placed tension member 10, define a three-dimensional shape that encompasses the tumor TM. The shape may be substantially oblong, with the first-placed tension member 10 defining a smaller diameter and the second-placed tension member 10 defining a larger diameter. As the second-placed tension member 10 is tightened, the three-dimensional shape may decrease in size. In particular, a size of the two-dimensional shape defined by the first-placed tension member 10 may remain substantially unchanged in its compressed state, while a size of a two-dimensional shape defined by the second-placed tension member 10 may decrease. The three-dimensional shape defined collectively by the first- and second-placed tension members 10 may likewise decrease, and may become less oblong or more equally proportioned. For example, the three-dimensional shape defined collectively by the first- and second-placed tension members 10 may transition from being substantially ovoid or substantially prolate spheroid in shape, to being substantially spherical in shape. As more tension members 10 are placed and tightened, the compressive three-dimensional shape that encompasses the tumor TM may increasingly resemble a sphere or, in other instances, may resemble some other three-dimensional shape, e.g., such as may correspond to a reduced-diameter version of an irregular three-dimensional shape initially defined by the tumor TM.

The tension members 10 may individually and/or collectively be referred to as a medical device, or as a device of foreign origin relative to the patient. The term "patient" is used broadly herein to refer to any suitable animal subject. The patient may, for example, be a human or any other mammal.

In other embodiments, the tension members 10 may be placed sequentially and tightened simultaneously. For example, in some embodiments, the tension members 10 may be placed about the volumetric region VR to substantially define a spherical three-dimensional shape. The tension members 10 may then be tightened simultaneously such that the spherical shape decreases in size, e.g., such that the radius of the sphere decreases.

In still other embodiments, a plurality of tension members 10 may be placed simultaneously and, in further embodiments, may be tightened sequentially or simultaneously. For example, in some embodiments, a mesh, net, or array that comprises a plurality of tension members may be placed around the tumor (e.g., fibroid). The mesh, net, or array, in some instances, may be applied at an exterior of an organ (e.g., uterus) in which the fibroid is embedded, and thus may also encompass a portion of the organ tissue. Once in place around the tumor and defining a three-dimensional shape of a first size, the constituent tensioning members can be tightened, either sequentially or simultaneously, thus shrinking, tensioning, compressing, reducing a profile of, or otherwise transitioning the three-dimensional shape to a second size that is smaller than the first size and compressing the tumor. In some embodiments an array may resemble the tension member patterns depicted, for example, in FIGS. 3I or 3J, but may be achieved without inserting any tension members through the organ (e.g., uterus) tissue. Rather, the tumor (e.g., fibroid) may be circumscribed by the tension members/array of tension members entirely externally relative to an outer surface of the organ (e.g., uterus).

With further reference to FIG. 3H, in the illustrated embodiment, four discrete tension members 10 arranged at about 45-degree angular offsets around the volumetric region VR of the organ ORG, which includes the tumor TM, in a body of a subject. Each tightened tension member 10 is circular in form and defines a discrete plane. In the illustrated embodiment, the planes intersect at a single line that passes through a center of volumetric region VR and/or tumor TM. In various embodiments, a minimum angular offset between adjacent tension members 10 can be no less than 10, 15, 20, 25, 30, 45, or 60 degrees.

When tightened, each of the tension members 10 can apply inwardly directed pressure to the tissue within the volumetric region VR—i.e., to the tumor and a circumscribed portion of the tissue of the organ ORG, in the illustrated embodiment—along separate lines of compression. In the illustrated embodiment, the compressive forces along each line of compression are directed inward, or toward an interior of the tumor. Moreover, in the illustrated embodiment, the compressive forces are radially compressive and directed toward a center of the tumor TM. In some embodiments, at least one of tension members 10 passes over and compresses blood vessels 17 (e.g., capillaries) feeding the tumor, thereby partially or fully occluding the blood vessels 17, for reducing or preventing, respectively, oxygenated blood from arriving at tumor tissue. In some embodiments, at least one of tension members 10 is deployed on a predefined passage, at least one predefined passage passes across one or more blood vessels.

FIG. 3I shows another example of a tension-member arrangement in which a different three-dimensional compressive pattern is formed. In this example, five discrete tension members 10 arranged in substantially parallel fashion around a volumetric region VR of an organ ORG that includes a tumor TM, in a body of a subject. Each tension member 10 defines a substantially circular two-dimensional form and defines a discrete plane. In the illustrated embodiment, the planes are parallel to one another. The four tension members 10 on the left can each direct compressive force toward an interior of the tumor. However, in some instances, some or all of the tension members 10 may not direct compressive forces to a center point of the tumor TM, but rather, may direct the compressive forces to a center line that passes through the tumor TM. Moreover, compressive forces of the rightmost tension member 10 may not be specifically directed toward an interior of the tumor, but may instead provide inwardly directed compressive forces to a circumscribed portion of the organ tissue that is adjacent to the tumor TM. Nevertheless, all of the tension members 10, and the volumetric or three-dimensional compression they provide to the volumetric region VR, can give rise to increased pressure within the tumor TM.

In the illustrated embodiment, each of the five tension members 10 can define a substantially two-dimensional compressive shape (e.g., a circle) that directs forces inwardly relative to the volumetric region VR, and the tension members 10 can collectively define a three-dimensional compressive shape that volumetrically compresses the volumetric region VR. In particular, in the illustrated embodiment, the three-dimensional compressive shape is substantially spherical.

FIG. 3J shows seven discrete tension members 10, each of which circumscribes a volumetric region VR of an organ ORG that includes a tumor TM, in a body of a subject. Each tension member 10 is circular in form and defines a discrete plane; the planes are angularly offset from each other by acute angles. In the illustrated embodiment, the planes all intersect at a line external to volumetric region VR and/or external to the tumor TM. A three-dimensional compressive shape defined collectively by the tension members 10 is substantially spherical, or substantially spherical with angled, truncated ends.

FIG. 3K shows a single tension member 10 circumscribing a volumetric region VR of an organ ORG that includes a tumor TM, in a body of a subject. Tension member 10 defines a spiral shape that extends along a length of volumetric region and, in the illustrated embodiment, extends through an angular rotation of approximately 5 full turns, or 1800 degrees, for example. In other embodiments, different numbers of turns are contemplated. For example, in various embodiments, the tension member 10 can extend about the tumor TM through an angular rotation of no less than about 360, 540, 720, 900, 1080, or 1260 degrees.

In some embodiments, the tension member 10 is placed around the volumetric region VR to define a three-dimensional shape, such as sphere. The tension member 10 can be tightened to reduce a size of the three-dimensional shape. For example, the tension member 10 can a suture that is wrapped around the volumetric region VR multiple times to substantially define a spherical, oblate spheroid, prolate spheroid, or other three-dimensional shape. The suture can then be pulled taut to reduce a size (e.g., volume) of the three-dimensional and compress the tumor TM. The suture may be tied or otherwise secured in the tightened state, such as in manners discussed hereafter.

It is noted that FIGS. 3A-3K are schematic and do not necessarily demonstrate all details of a compressed arrangement. For example, in some instances, the amount of organ (e.g., uterine) tissue that is present in the volumetric region VR may be relatively smaller than what is shown. Moreover, in some embodiments, the tension forces provided by the tension members 10 can be extremely large, such that a shape of the tumor TM may be altered by the presence of the tension members 10. In many instances, the tumor TM and/or the volumetric region VR, more generally, can bulge outwardly between adjacent tension members 10. Accordingly, the neat spherical arrangements of the tumor TM and volumetric region VR shown, for example, in each of FIGS. 3H-3K, may instead be less regular and include outward bulges between each set of adjacent tension members 10 (FIGS. 3H-3J) or adjacent turns of the tension member 10 (FIG. 3K).

FIG. 4 shows a block diagram of an illustrative method 50 for treating a tumor, optionally a uterine fibroid, within a body of a subject, optionally resulting in an arrangement of taut tension members provided round and/or through the tumor, as shown for example in FIGS. 2A, 2B, 3A-3F and 3H-3K, or in any combination thereof. The tumor may be intramural, subserous or submucosal (as shown in FIG. 1), and method 50 may involve treating simultaneously, in sequence, in parallel, or in any combination, a plurality or a cluster of tumors which may be of forms, sizes, shapes and/or types.

For example, with respect to simultaneous treatment of a cluster of tumors, it should be noted that although the previous examples depict a single tumor or a portion of a single tumor TM within a volume V (FIG. 2A), a volumetric region VR (FIGS. 3H-3K), or a volumetric portion V1, V2 (FIG. 2B), in other instances a plurality of tumors e.g., a tumor cluster) may be present within the volume V, volumetric region VR, or volumetric portion V1, V2. Thus, in some instances, a medical device, such as a plurality of tension members 10, can envelop, enshroud, encircle, enclose, encompass, or otherwise extend around the plurality of tumors, such as in the illustrative three-dimensional patterns previously discussed. The tension members 10 can be tightened or otherwise give rise to compressive forces that compress the plurality of tumors, thus simultaneously treating all tumors encompassed by the tension members 10.

In other or further instances, a plurality of tumors may be treated by individually encompassing each tumor with one or more tensioning members and tightening the one or more tensioning members, in manners such as described previously and hereafter. For example, a method can comprise performing the method 50 one or more times with respect to a first tumor, and separately repeating the method 50 one or more times with respect to a second tumor; separately repeating the method 50 one or more times with respect to each of second and third tumors; repeating the method 50 one or more times with respect to each of second, third and fourth tumors; etc.

With continued reference to FIG. 4, the illustrated method 50 includes the following steps or stages, which are performed sequentially in the illustrated embodiment, as shown by the arrows in FIG. 4. In other instances, the one or more of the stages may be performed simultaneously or in different orders. At stage 51, a volumetric region of a tumor, such as volume V of FIG. 2A, the volumetric portions V1 or V2 of FIG. 2B, or the volumetric regions VR of FIGS. 3H-3K, for example, is defined. The volumetric region can be defined in any suitable manner. For example, a practitioner may define the volumetric region by visually inspecting a tumor, such as a uterine fibroid, which may be covered by organ tissue (e.g., the uterine wall) via any suitable imaging system. In some instances, a laparoscope may comprise the imaging system. Defining the volumetric region thus may entail the identification of a region about which the practitioner intends to pass one or more tensioning members. In other or further instances, defining the volumetric region may comprise actually placing the one or more tensioning members around the volumetric region, such as described with respect to stage 52.

At stage 52, a tension member (e.g., tension member 10) is passed around the volumetric region, optionally in close fit or on or along a periphery of the volumetric region. Any suitable method of passing the tension member around the volumetric region is contemplated. For example, a number of illustrated methods for such placement are discussed below with respect to FIGS. 5A-12J. The term "close fit" is used herein to indicate that the tension member is near or in close proximity to the volumetric region. For example, in various embodiments, the close fit can represent a distance having a value that is no greater than 30, 25, 20, 15, 10, or 5 percent of a maximum diameter of the tumor.

At stage 53, the tension member is tightened, such as with a chosen tension force, so as to affect compression (e.g., radial compression) of the volumetric region for increasing pressure within the tumor. The increased pressure may be of one or more varieties.

For example, the increased pressure within the tumor may be related to (1) a total compressive force applied to the tension member, or optionally to a number of tensions members, and (2) the total surface area of the tumor or a volumetric region of the organ encapsulating the tumor or part thereof. For example, the pressure may be calculated as a total compressive force applied by the tension member divided by a surface area of the volumetric region physically contacted by the tension member. In other or further instances, the pressure may be calculated as the total compressive force divided by a total surface area of the volumetric region. The pressure may be ambient or absolute. The pressure may be an average pressure of the entire tumor volume, or a pressure measured adjacent to compressed lines or surfaces caused by the tightened tension member(s). In some embodiments, the increased pressure within the volumetric region and/or within the tumor is greater than about 20 mmHg, optionally greater than about 50 mmHg, optionally greater than about 100 mmHg, optionally greater than about 200 mmHg, optionally between 30 mmHg and 200 mmHg.

Additionally or alternatively, the increased pressure within the tumor may be related to capillary blood pressure. For example, the capillary pressure within the volumetric region, or as measured at a downstream position relative to blood vessels (capillaries or arteries) directly feeding the tumor, may increase. As a result, the raised capillary pressure can inhibit or prevent oxygenated blood from blood vessels (capillaries or arteries) that directly feed the tumor from supplying the oxygenated blood into the volumetric region. In some embodiments, the increased pressure within the volumetric region and/or within the tumor causes local capillary pressure greater than about 5 mmHg, optionally greater than about 10 mmHg, optionally greater than about 20 mmHg, optionally greater than about 25 mmHg, optionally greater than about 50 mmHg, optionally between 10 mmHg and 22.5 mmHg.

Additionally or alternatively, the increased pressure within the tumor may be related to interstitial fluid pressure measured in the tumor and/or in surrounding host tissue, which are known to cause physical barrier for delivery of cell nutrients and small molecules into the tumor. In some embodiments, the increased pressure within the volumetric region and/or within the tumor causes local interstitial pressure greater than about 0.1 mmHg, optionally greater than about 0.5 mmHg, optionally greater than about 1 mmHg, optionally greater than about 4 mmHg, optionally greater than about 10 mmHg, optionally between 0.1 mmHg and 5 mmHg.

Accordingly, in various embodiments, the increased pressure in the volumetric region can be one or more of an increased tension force as applied over a surface area (e.g., a contact area or a total surface area) of the volumetric region, an increased capillary pressure within the volumetric region, and/or an increased interstitial fluid pressure within the volumetric region. The one or more varieties of increased pressure can be above a suitable pressure threshold for each applicable variety of pressure that is sufficient to cause ischemia within the volumetric region and/or within the tumor. When the specified pressure is maintained above the ischemic threshold for a sufficient period, necrosis of affected tumor tissue can result. As discussed elsewhere herein, the elevated pressure (e.g., above the ischemic pressure threshold) can be maintained for a period sufficient to achieve the necrosis of tumor tissue (e.g., at least a majority of the tumor tissues, substantially all of the tumor tissues, etc.). In various instances, the period is at least 1 hour and/or no less than 4, 5, 6, 7, or 8 hours. In various instances, the elevated pressure is maintained for a period of no less than 1, 2, 3, 4, 5, 6, or 7 days; no less than 1, 2, 3, or 4 weeks, or no less than 1 or 2 months.

The passing at stage 52 may involve a plurality of tension members, optionally along separate paths around and/or through the volumetric portion defined. In case that the defining at stage 51 is for a plurality of volumetric portions, the passing at stage 52 may involve one or more of the tension members around and/or through one of the volumetric portions, and other of the tension members around and/or through another of the volumetric portions.

The tightening at stage 53 may involve increase of pressure inside the tumor to above capillary blood pressure by way of the inward or radial compression, and the increased pressure may be continuously maintained to cause ischemia in most of all tissues of the tumor. Once the pressure, e.g., capillary blood pressure, within the volumetric region has been raised to a sufficient level, blood flow into the volumetric region will decrease or cease. Thus, ischemia in most or all tissues of the tumor may be substantially instantaneous upon achieving a threshold pressure that exceeds, e.g., systolic capillary pressure. This ischemic condition can be maintained until necrosis of the tissue is achieved in full or in part. In case that the defined volumetric portion is for most or all volume of the tumor (e.g., volume V of FIG. 2A), the tightening at stage 53 may be configured to affect spherical radial compression of the tumor by one or more of tension members 10.

The tension member applicable for use with method 50, optionally tension member 10, may be configured as an elongated filament, cable, wire, strip, etc. For example, in various embodiments, the tension member 10 can comprise a suture cable or suture wire. The tension member in use may be comprised of a material comprising at least one of: implant-grade metal alloy, implant-grade polymer, implant-grade textile, and biodegradable material. In various embodiments, the tension member may be configured with a yield strength or a maximal tension force of at least 25 newtons (about 2.55 kg), at least 40 newtons (about 4 kg), at least 50 newtons (about 5.1 kg), at least 80 newtons (about 8.16 kg), or at least 120 newtons (about 12.24 kg). In various embodiments, the tension member 10, or each tension member 10 in instances where a plurality of tension members are used, can be tightened to or otherwise tensioned at tension force of no less than 20, 25, 30, 35, 40, 45, 50, 55, 60, 70, 80, 90, 100, 110, or 120 newtons.

The stage 51 of defining the volumetric portion may include choosing an entry opening and an exit opening, for passing the tension member therebetween and through, at a surface of the organ around and/or through the tumor; it may also include defining the plane crossing the volumetric portion and/or the tumor between the entry and exit points; and it may also include defining the volumetric portion as a whole. Optionally and alternatively, the stage 51 of defining can be considered an optional step that the user (surgeon) may chose to ignore without compromising integrality of method 50. The stage 51 of defining the volumetric portion or portions may include, may follow or be followed by, or may be replaced by a step of defining one or more passage lines (e.g., passage line 204 shown in FIG. 7A, for example) for passing therealong the tension member between an entry opening and an exit opening formed on the tumor and/or on tissue surrounding the tumor. When describing that the tension member is passed between the entry opening and the exit opening, an exemplary process may include the tension member first advanced through the exit opening, through the intramural region of the uterus, and then through the entry opening (which is a retrograde direction relative to an elongated member such a stylet or a needle applied for forming a surgical passage between these points for pulling the tension member therethrough). Nevertheless, the tension member extends between the entry and exit openings, and thus can be characterized as passing between the entry opening and the exit opening. In other embodiments, it is contemplated that the tension member can be passed in the opposite direction, i.e., in through the entry opening and out through the exit opening.

The at least one defined passage line optionally projects across blood vessels 17 feeding the tumor, such that the tightening of the tension member passing along the passage line directly affects occlusion of the blood vessels (as shown in FIG. 3H, for example). Defining 51 may include calculating, configuring, and/or optimizing a spatial arrangement of a plurality of tension members for affecting the occlusion for preventing an estimated maximal volume of blood from feeding the tumor upon the tightening and/or for affecting an estimated maximal radial compression of the volumetric portion.

Figure 5A:
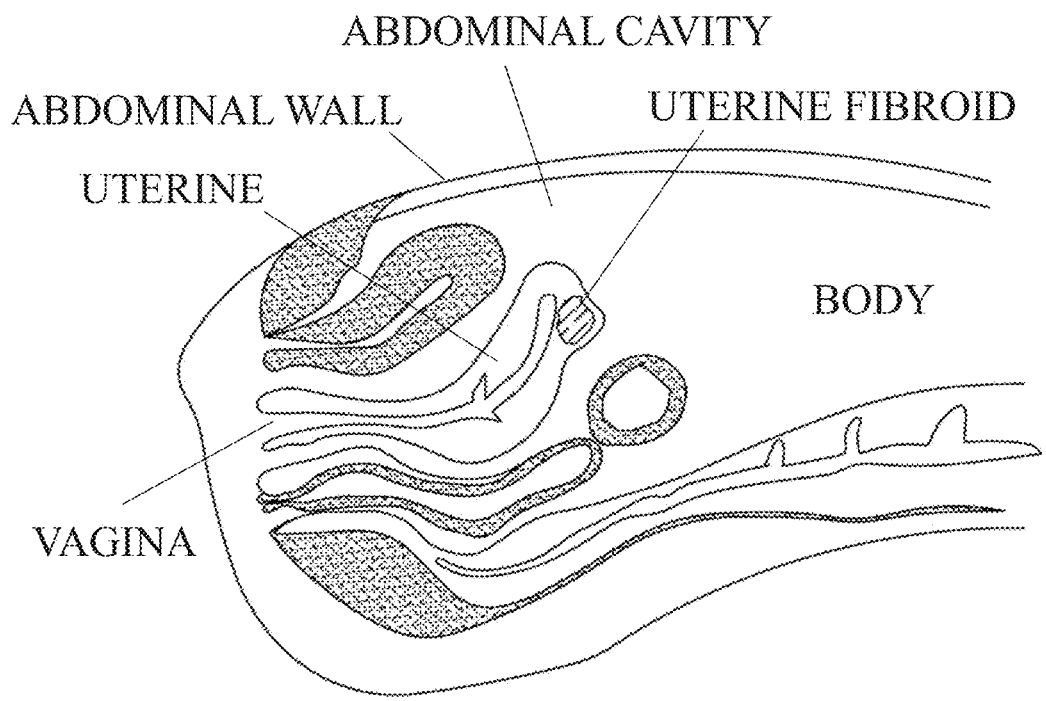
FIGS. 5A-5F schematically illustrate exemplary scenarios representing steps in an exemplary procedure for accessing a uterine fibroid, according to some embodiments.
Figure 5B:
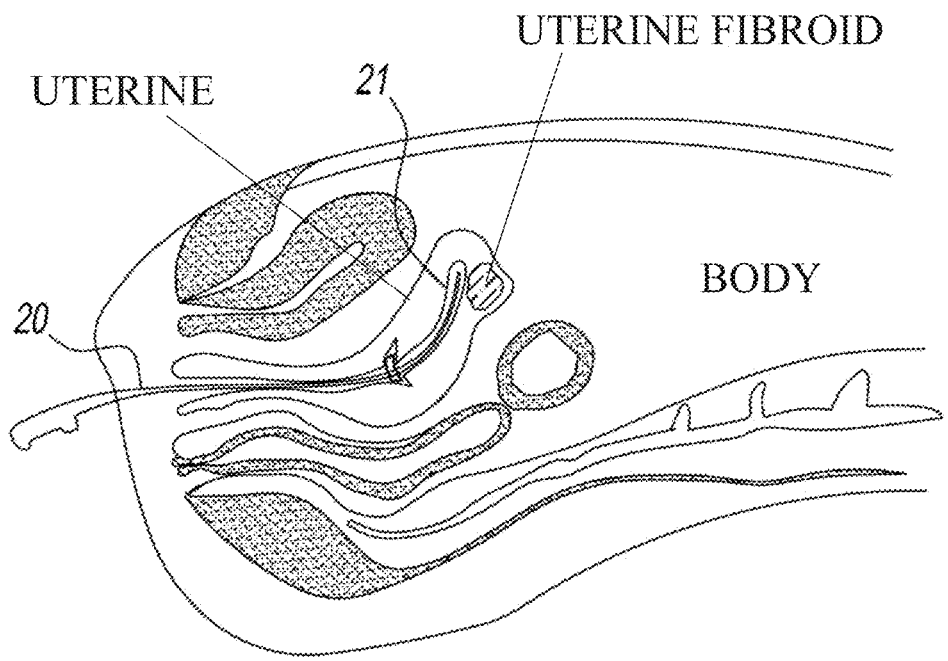
Figure 5C:
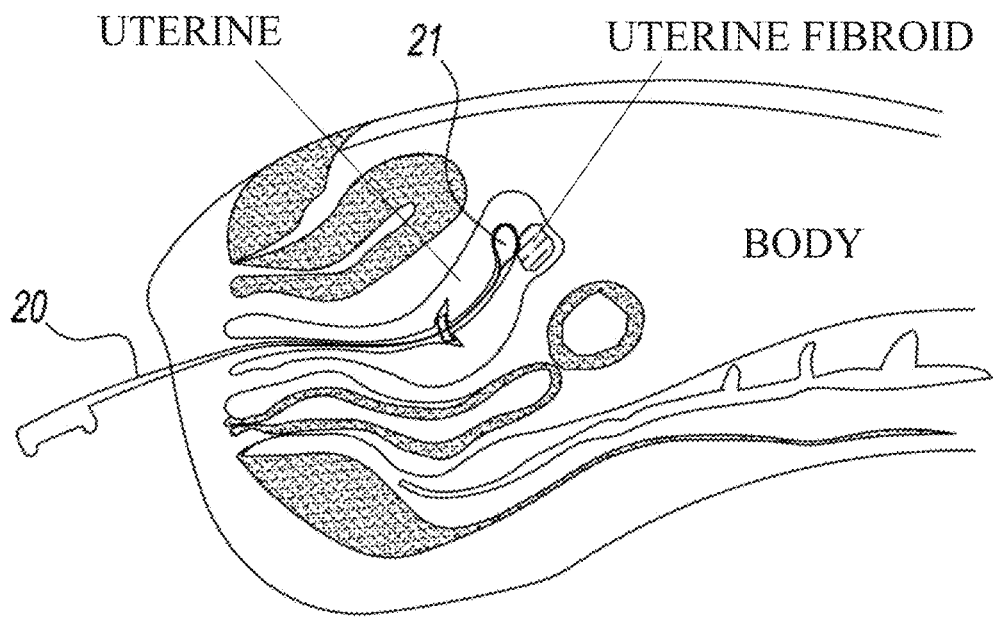
Figure 5D:
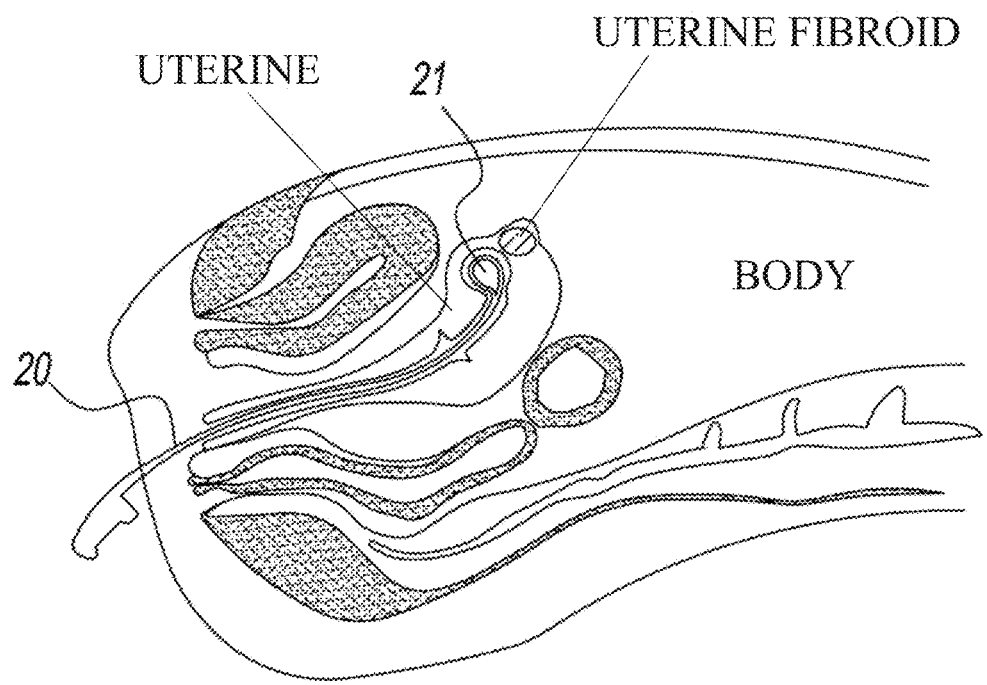

FIGS. 5A-5F schematically illustrate exemplary scenarios representing steps in an exemplary procedure for accessing a uterine fibroid (shown in FIG. 5A) for applying tension members thereto, such as by way of executing one or more versions of method 50 or similar methods, in a body of a subject. A uterine manipulator 20 with or without an expandable (e.g., inflatable) member 21 at a distal end thereof is deployed in the uterus, via the vagina (FIG. 5B), engages with uterus walls, (and expandable member 21 optionally partly conform to shape imposed by uterus wall inner boundaries and/or affect a dilated shape to uterus wall inner boundaries (FIG. 5C)). The uterine manipulator 20 can then be applied for contouring, shifting and/or pointing the uterus or a portion thereof in different directions, so that an operator can apply uterine manipulator 20 shift and direct the uterine fibroid closer to and/or towards the abdominal wall (as shown in FIG. 5D), for example, in case the access to the fibroid will be performed surgically via the abdominal wall and to the abdominal cavity (optionally inflated by $CO_2$ for ease of operation).

Figure 5E:
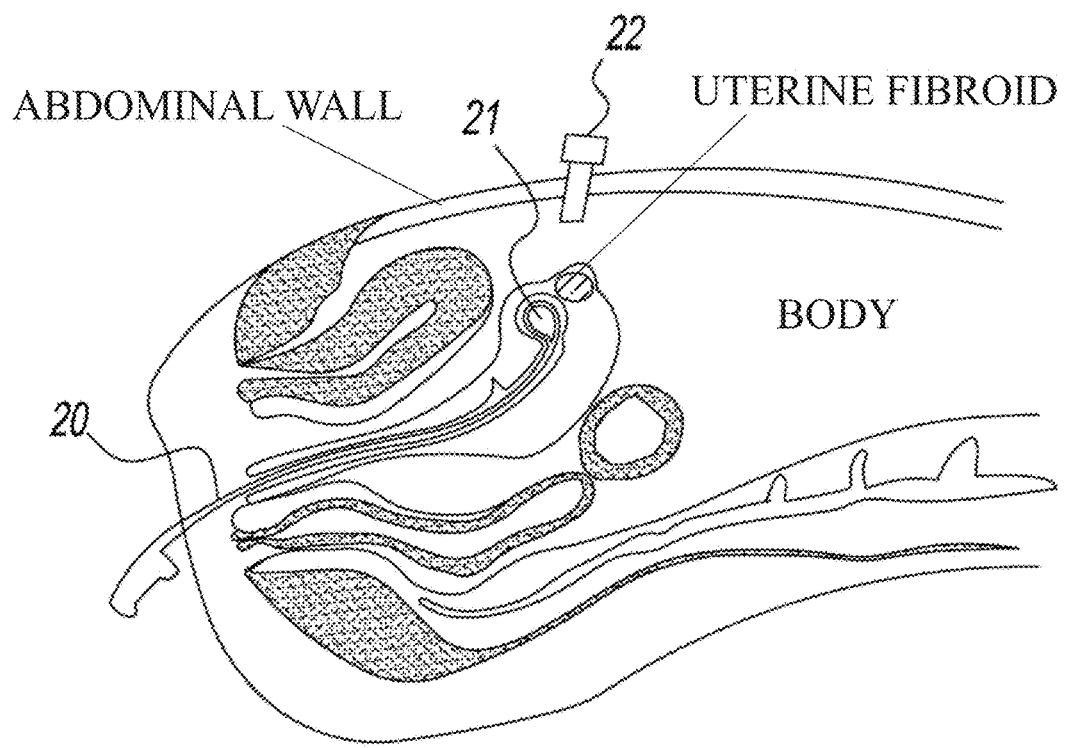
Figure 5F:
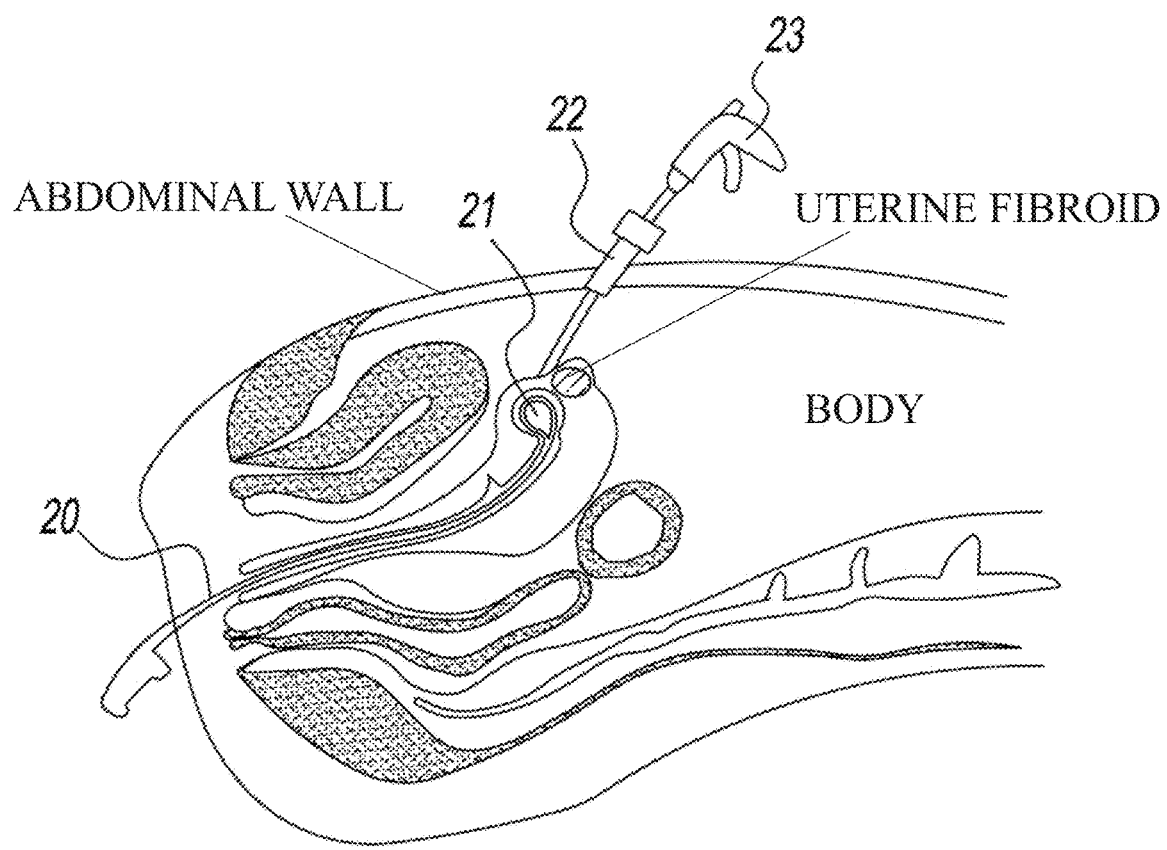

Stated otherwise, in certain methods, a uterine manipulator 20 can be used to achieve a desired orientation of the fibroid. Manipulation of the fibroid via the uterine manipulator 20 may orient the fibroid closer to the abdominal wall and/or more readily accessible via a laparoscopic procedure, as shown in FIGS. 5D-5F. The use of any suitable uterine manipulator 20 is contemplated, including those known in the art and those yet to be devised. Any suitable procedures for providing surgical access to the uterus via the abdomen are also contemplated, including any suitable procedure for providing laparoscopic access.

FIGS. 5E and 5F illustrate further steps that may be employed in some methods. In particular, in some instances, the uterine manipulator 20 may be used in conjunction with a minimally invasive surgical procedure, such as a laparoscopy. As shown in these figures, certain methods can include creating a surgical passage into the abdomen of a patient and reaching the surface of the uterus, provided in the abdominal cavity, by way of laparoscopy, using a laparoscopic port 22 and a laparoscopic apparatus 23. The laparoscopic apparatus 23 can be configured for delivering and/or passing one or more tension members in the uterus, around the fibroid. Illustrative embodiments of such laparoscopic apparatuses are described hereafter.

FIGS. 6A-6J schematically illustrate exemplary scenarios representing steps or stages in a method for treating a tumor within a body of a subject. In some instances, the stages may take place after direct access is formed (e.g., minimally invasively) from outside body of the subject (patient) to the tumor, such as, for example, via methods as depicted in FIGS. 5A-5F. The minimally invasive access to the tumor may be created by way of transvaginal procedures, endoscopy, laparotomy or laparoscopy.

Figure 6A:
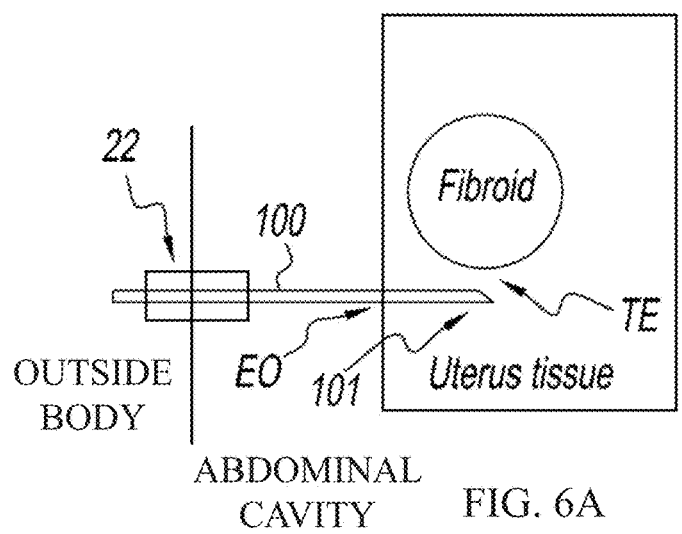
FIGS. 6A-6J schematically illustrate exemplary scenarios representing steps in a method for treating a tumor within a body of a subject, according to some embodiments.
Figure 6B:

FIG. 6A, illustrates use of a laparoscopic, minimally invasive access using the laparoscopic port 22. Via the surgically created access to the uterus, an outer tube 100 is positioned at an entry opening EO across a tissue wall (uterus tissue) surrounding the tumor (fibroid) such that a distal end 101 of outer tube 100 is located adjacent to a transverse extremity TE of the fibroid (FIG. 6A). A curved needle 102 is then pushed through a lumen of the outer tube 100, until a distal portion 103 of the curved needle 102, protruding from outer tube 100, regains a curved shape (FIG. 6B).

Figure 6C:
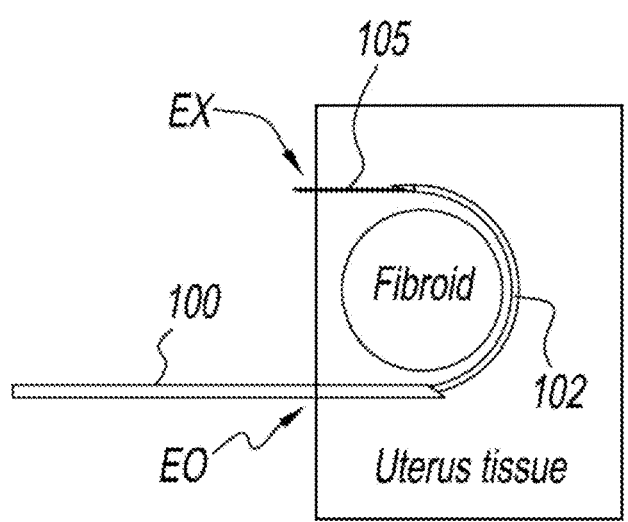
Figure 6D:
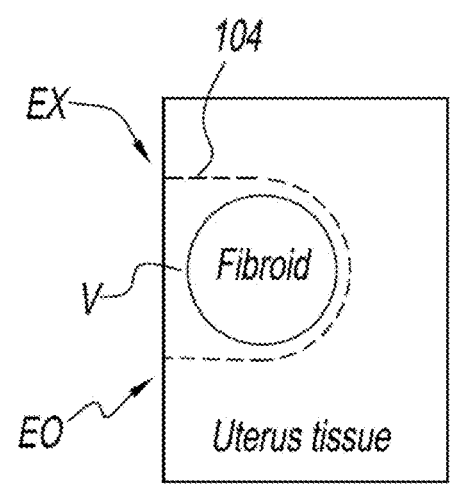

Curved needle 102 forms part of a passage 104 around at least half of perimeter of the fibroid. A stylet 105 is then pushed distally through curved needle 102 via entry opening EO, passing through the curved distal portion 103 of the needle 102 and exits the uterus tissue at an exit opening EX, thereby completing formation of the passage 104 around volumetric portion V. FIG. 6D schematically illustrates the same scenario as in FIG. 6C with virtual representation of passage 104 and volumetric portion V, without showing outer tube 100, curved needle 102 and stylet 105, which are present as shown in FIG. 6C, for ease of explanation only. Passage 104 is in a close fit and surrounds a volumetric portion V of the fibroid extending between entry opening EO and exit opening EX around the tumor and optionally some of the uterus tissue surrounding the tumor.

Stylet 105 includes means such as a loop 106, at a distal end thereof, configured for facilitating fixation to a tension member, which tension member may be in the form of a suture cable or suture wire 107. For example, as shown in FIG. 6F, a proximal end 108 of the stylet 105 may include a loop 106 through which the tension member 107 has been passed prior to passing the stylet 105 through the curved needle 102. The loop 106 may, for example, retain therein an intermediate portion of the tension member 107, such that the tension member 107 is folded over into two lengths, and the opposite ends of the tension member at the tip of each length remain at an exterior of the patient during passage of the stylet 105 and the intermediate portion of the tension member 107 through the passage 104 around the fibroid.

With reference again to FIG. 6E, the stylet 105 can be pushed through the outer and inner needles 100, 102 along a curved path around the fibroid. The distal end of the stylet 105 may be sufficiently sharp to, in some instances, pierce through a final portion of the uterine tissue to complete formation of the passage 106, as previously mentioned. As shown in FIG. 109, in some embodiments, a laparoscopic grasper 109 is inserted into the body (e.g., via the laparoscopic port 22) and manipulated to grasp a distal end of the stylet 105. The grasper 109 can be withdrawn proximally while holding the stylet 105 to draw the stylet 105 and the intermediate portion of the tension member 107 that is coupled thereto through the passage 104. Ultimately, the proximal end 108 of stylet 105 is pulled from exit opening EX (FIG. 6E) until stylet loop 106 with an intermediate portion of tension member 107 exit the uterus tissue (FIG. 6F), after passing through passage 104. The tension member 107 can thereby extend between and through entry opening EO and exit opening EX around volumetric portion V. Pulling of stylet 105 may continue until portion of tension member 107 (i.e., the intermediate portion) is provided outside subject's body (FIG. 6G). The outer tube 100, curved needle 102 and stylet 105 can be removed, leaving only tension member 107 in place along passage 104 (FIG. 6H). In the event tension member 107 runs along passage 104 in one direction and back (as shown in FIG. 6H), the tension member 107 may then be adjusted in a way that it will follow passage 104 only in a single direction (as shown in FIG. 6I), or stated otherwise, such that only a single strand of the tension member 107 passes through the passage 104. For example, in some embodiments, as previously discussed, two lengths of the tension member 107 pass through the passage 104 in FIG. 6H due to the folded-back arrangement of the tension member 107. One of these lengths can be pulled on at the exterior of the patient, such that the length passes through the passage 104 (e.g., in the direction of the entry opening EO to the exit opening EX) and ultimately out of the patient through the laparoscopic port 22 to arrive at the arrangement depicted in FIG. 6I.

Figure 6E:
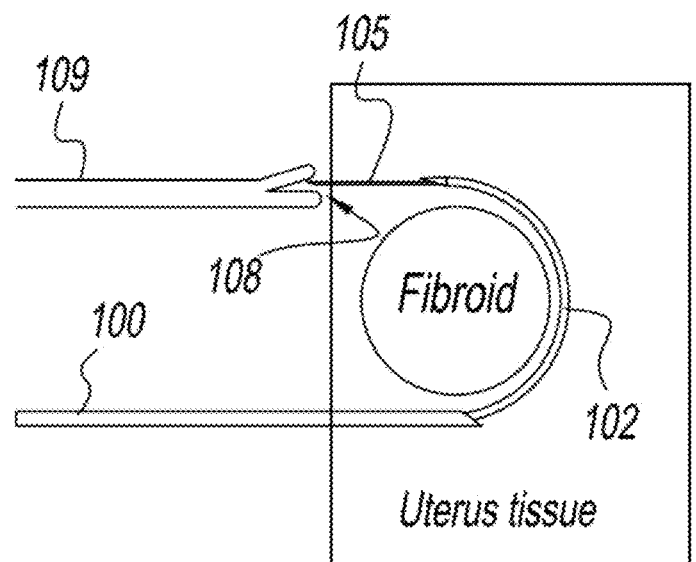
Figure 6F:
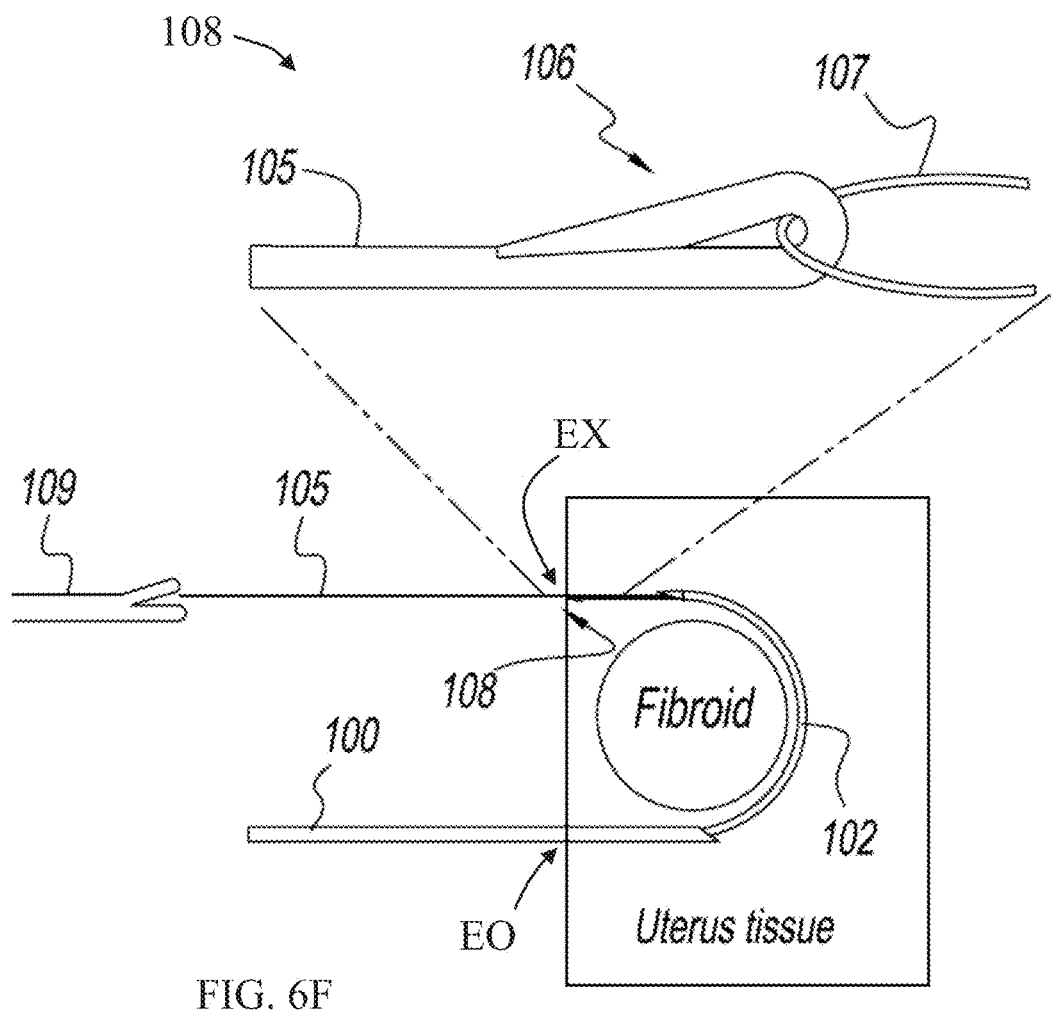
Figure 6G:
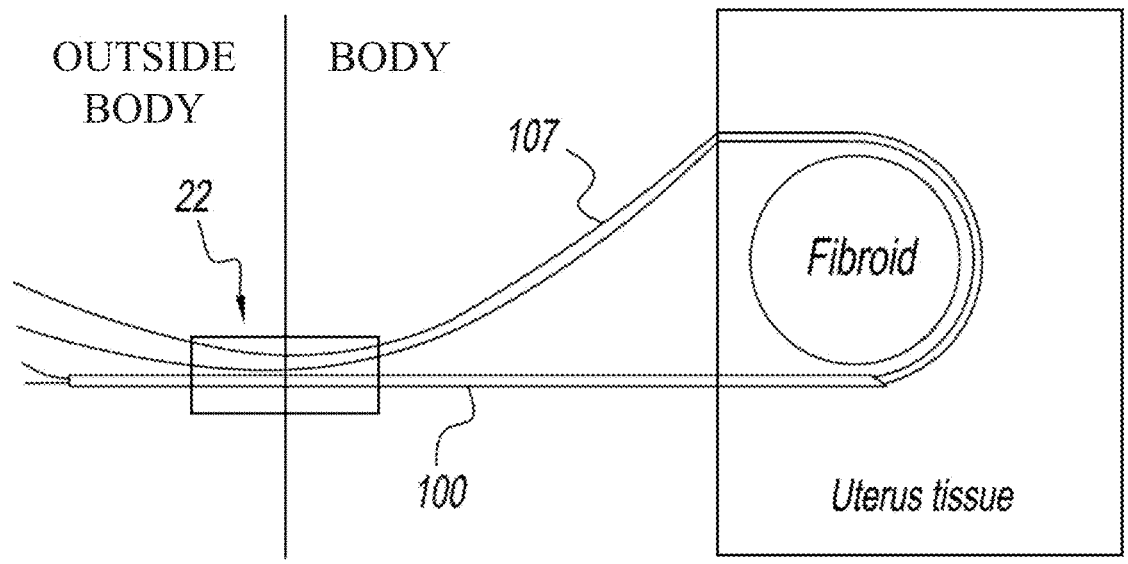
Figure 6H:
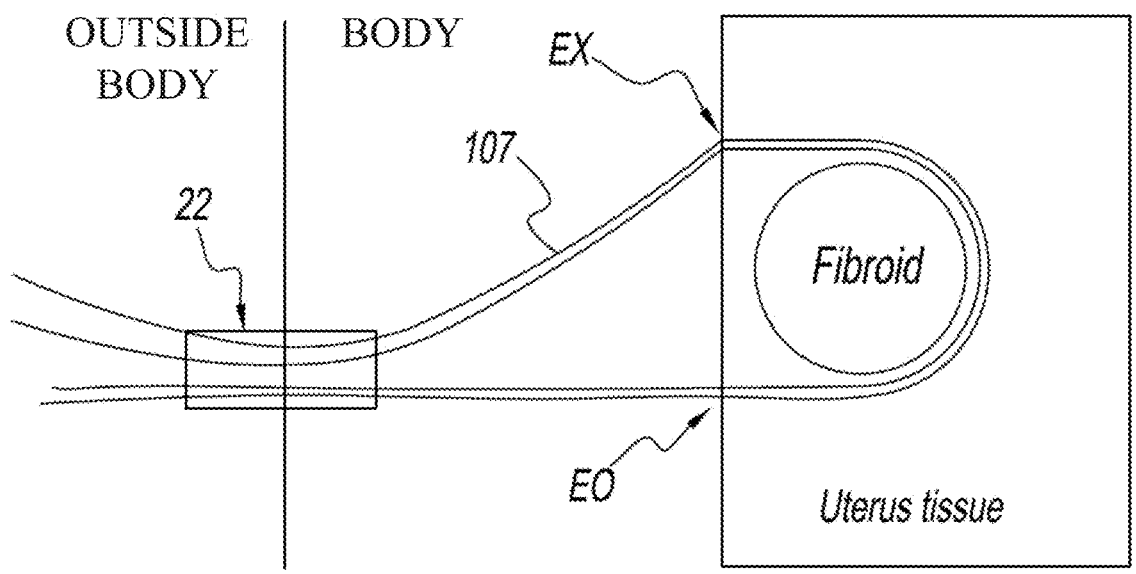
Figure 6I:
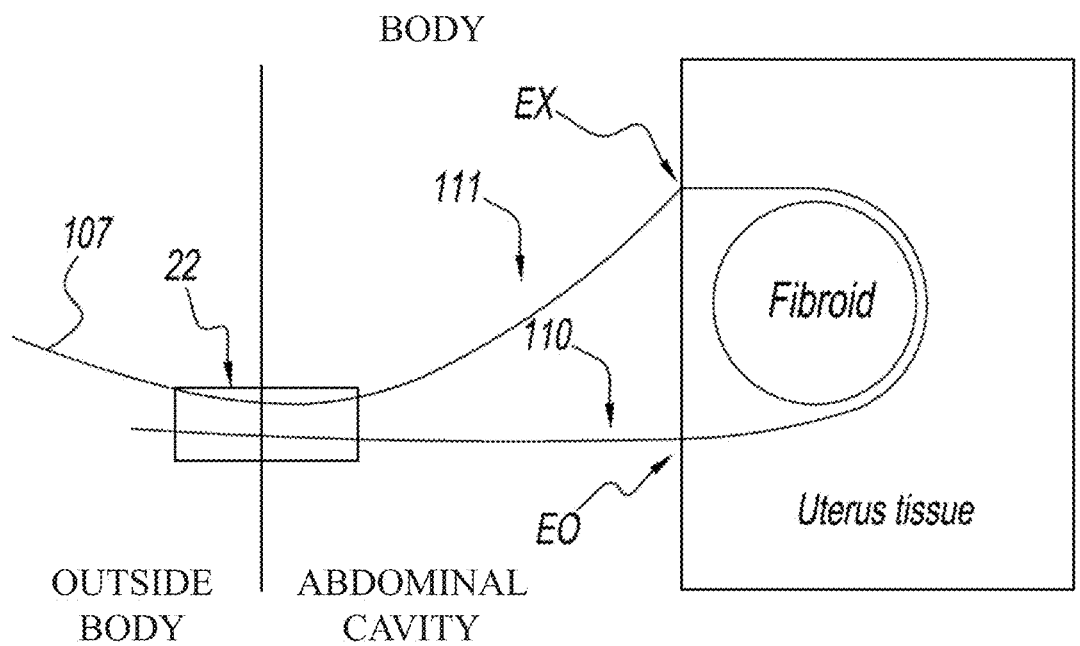
Figure 6J:
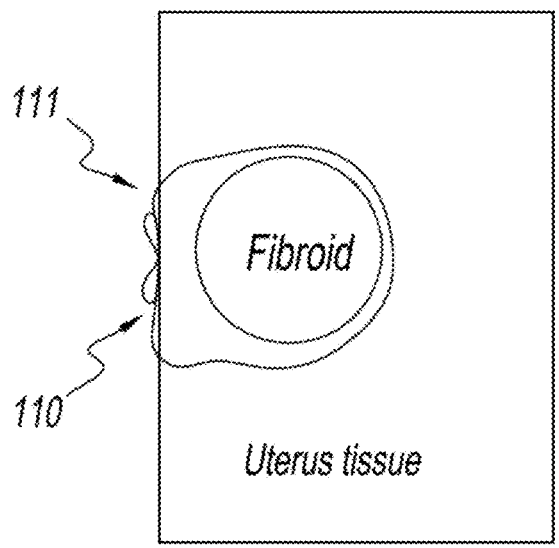

With reference to FIG. 6J, in certain embodiments, the tension member 107 is then tightened along its length, e.g., with a chosen tension force, so as to affect compression (e.g., radial compression) of the volumetric portion for increasing pressure within the tumor. A first portion 110 of tension member 107 protruding from entry opening EO is secured to a second portion 111 of tension member protruding from exit opening EX, such as via a suture knot and/or a fastener (e.g., a crimped fastener, as discussed elsewhere herein). The tension member 107 can be sufficiently taut to individually, or in combination with additional tension members 107 placed subsequently in similar manners, raise pressure within the volumetric region V and/or the fibroid by an amount sufficient to cause ischemia of the volumetric region V and/or the fibroid, as previously discussed. The tightening can be maintained after securing tension member 107, at least until most or all tissues of the tumor necrotize, as previously described. The described securement of the first and second portions of the tension member can be achieved outside boundaries of the tumor (e.g., the fibroid), and/or optionally outside boundaries of an organ (e.g., the uterus) in the body containing the tumor.

FIG. 6J is schematic, and does not necessarily depict an amount of tension being applied to the fibroid. In some instances, the amount of tension supplied by the tension member 107 is sufficient to dig into, embed into, squeeze, deform, reshape, or otherwise alter the fibroid.

The illustrative method stages depicted in FIGS. 6A-6J will now be further described in other or further terms. The illustrated methodology is performed via a system and/or an apparatus that includes a first needle, elongated member, access tube, or tubular member 100. The first needle 100 can include a sharpened (beveled, pointed, etc.) distal tip to facilitate entry into the uterus to a first depth. The first needle 100 can define an inner lumen. The first needle 100 can be formed of any suitable material, such as, for example, stainless steel. In some instances, the first needle 100 can be rigid so as to resist transverse deflections thereof during passage through the patient and/or organs thereof.

The system or apparatus can further include a second needle, elongated member, access tube, or tubular member 102 having an outer dimension (e.g., an outer diameter) of a sufficient size to be translational, slidable, advanceable and retractable, or otherwise movable within the lumen of the first needle 100. The second needle 102 can include a sharpened (beveled, pointed, etc.) distal tip to facilitate passage through the uterus and/or (in some instances) the fibroid to form a second length of the passage 104 around the volumetric region of the tumor. In some embodiments, the second needle 102 includes a pre-curved distal end. The distal end 103 of the second needle 102 can, in some embodiments, be resiliently flexible. In some embodiments, the rigidity of the first needle 100 is sufficient for the first needle 100 to maintain a substantially rectilinear orientation while the pre-curved distal end or distal portion 103 of the second needle 102 is maintained within the lumen of the first needle 100. For example, in some embodiments, the pre-curved distal end 103 of the second needle 102 can be positioned within the first needle 100 in a straightened orientation. The first needle 100 can be sufficiently rigid to maintain the pre-curved distal end 103 of the second needle 102 in the straightened orientation as the second needle 102 is advanced through the lumen of the first needle 100. Moreover, during retraction of the second needle 102 into the first needle 100 after use of the second needle 102, the first needle 100 may be sufficiently rigid to assist in transitioning the distal end 103 of the second needle 102 from the natural, pre-curved state back to the straightened state. The second needle 102 can be formed of any suitable material, such as, for example, stainless steel, nitinol, various plastics, etc. In some embodiments, the second needle 102 may desirably be sufficiently rigid to readily pass through uterine and/or fibroid tissue. The second needle 102 may be resiliently flexible, so as to readily and naturally transition from the temporary or restrained straightened orientation to the pre-curved orientation upon delivery of the second needle 102 through the distal end of the first needle 100. The second needle 102 may further define a lumen therethrough.

The system or apparatus can further include an elongated member for coupling with a suture, which may be referred to as a suture passer or stylet 105. The stylet 105 can be appropriately sized to be translational, slidable, advanceable and retractable, or otherwise movable within the lumen of the second needle 102. In the illustrated embodiment, the stylet 105 can be longitudinally rigid so as to be capable of being advanced longitudinally through the first and second needles 100, 102. The stylet 105 can further be transversely bendable or deflectable, so as to be readily passable through the curved distal region 103 of the needle 102. In the illustrated embodiment, the longitudinal rigidity of the stylet 105 is such that upon exiting the pre-curved portion 103 of the second needle 102, the distal portion of the stylet 105 forms a substantially rectilinear path, while more proximal portions of the stylet 105 that remain within the curved portion 103 are curved to match a curved profile of the lumen of the second needle 102. In some embodiments, a distal tip of the stylet 105 can be sufficiently sharp or otherwise configured to pierce through uterine and/or (in some instances) fibroid tissue.

The system may be used, for example, in a minimally invasive laparoscopic procedure. For example, a procedure such as depicted in and described with respect to FIGS. 5E and 5F, and/or additionally FIGS. 5A-5D, may be performed to provide access to the uterus and a fibroid. Via the laparoscopic port 22, the first needle 100 may be introduced into the patient and into the uterus, as depicted in FIG. 6A. In particular, the sharpened distal tip of the first needle can form the entry opening EO at the surface of the uterus. The distal tip of the first needle 100 may be further advanced through the uterus to a depth that is appropriate for deployment of the second needle 102, such that the second needle 102 can extend around an outer periphery of the fibroid.

With reference to FIG. 6B, the second needle 102 can be advanced through the lumen of the first needle 100 while the pre-curved distal end 103 thereof is retained (e.g., via the inner surface of the first needle 100 that defines the lumen thereof) in the in the straightened state. The second needle 102 can be advanced distally through a distal opening of the first needle 100. As the second needle 102 exits the first needle 100, the distal region 103 of the second needle 102 can naturally, automatically, and/or resiliently return to its pre-formed curvature, and thus may form a curved path around the fibroid as the second needle 102 is further advanced distally through the distal opening of the first needle 100. The pre-formed curvature may extend around at least a portion of a perimeter of the fibroid. For example, in various embodiments, the pre-curved distal region 103 may form a curved path that curves about an angle of no less than 30, 45, 60, 75, 90, 135, 180, or 270 degrees. In the illustrated embodiment, the angle is approximately 180 degrees. In various embodiments, the pre-curved distal region 103 may form a curved path that extends about no less than one fourth, one third, one half, two thirds, or three fourths of a perimeter (e.g., a circumference) of the fibroid.

In some embodiments, the pre-curved distal region 103 can be advanced until a distal end of the second needle 102 pierces through the outer surface of the uterus. In the illustrated embodiment, the pre-curved distal region 103 instead extends exclusively through intramural uterine tissue, and stops short of the upper surface, as shown in FIG. 6B.

With reference to FIG. 6C, in some embodiments, the stylet 105 can be advanced distally through the second needle 102. The distal end of the stylet 105 can pierce through uterine tissue to form the exit opening EX through the outer surface of the uterus. With reference to FIG. 6D, each of the first needle 100, the second needle 102, and the stylet 105 can form separate legs of the passage 104 around the volume V and the fibroid. Stated otherwise, the first needle 100, the second needle 102, and the stylet 105 can collectively form the passage 104 around the fibroid.

With reference to FIGS. 6E and 6F, as previously discussed, a proximal end 108 of the stylet 105 can be coupled with the tension member 107. The stylet 105 thus can be pulled, e.g., via the grasper 109, which can thread or otherwise pass the tension member 107 along the path or passage 104. In the illustrated embodiment, two lengths of a folded over tension member 107 are passed along the passage 104 through the entry opening EO, around the fibroid (e.g., exclusively through intramural uterine tissue), and through the exit opening EX. One of the lengths of the tension member 107 may continue to be passed through the passage 104 in the same direction until only one length of the tension member 107 protrudes through the entry opening EO and only the other length protrudes through the exit opening EX, as shown in FIG. 6I. The two lengths of the tension member 107 can be secured and tightened in manners such as previously discussed, and as schematically depicted in FIG. 6J.

In some methods, one or more additional tension members 107 are provided around the fibroid by repeating this method. The additional tension members 107 can yield three-dimensional compressive arrangements, such as previously described, for example, with respect to FIGS. 3A, 3H-3K. Other apparatus, systems, and methods discussed hereafter likewise can be used to place a plurality of tension members around a fibroid, such as by repeating disclosed steps using additional tension members. The additional tension members can yield three-dimensional compressive arrangements, such as previously described, for example, with respect to FIGS. 3A, 3H-3K.

FIGS. 7A-7F schematically illustrate exemplary scenarios representing steps or stages in another illustrative method for treating a tumor. The depicted stages may take place after direct access is formed (e.g., minimally invasively) from outside body of the subject (patient) to an organ (uterus) surrounding the tumor, as shown for example in FIGS. 5A-5F. The minimally invasive access may be created by way of transvaginal procedures, endoscopy, laparotomy or laparoscopy. An apparatus 299, comprising of an outer tube 200, a curved needle 202, a stylet 205 and optionally also a crimping mechanism or device 209, is applied. In some instances, a tension member 207 is also present within the apparatus 299.

Figure 7A:
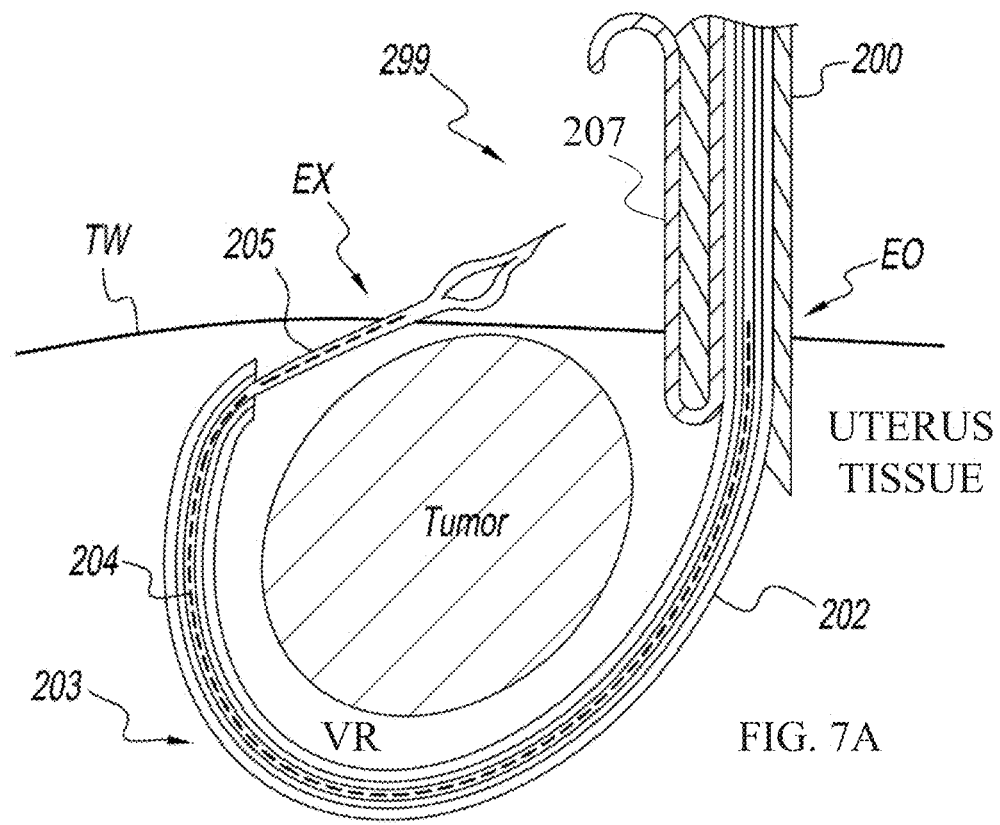
FIGS. 7A-7F schematically illustrate exemplary scenarios representing steps in a method for treating a tumor within a body of a subject, according to some embodiments.

As shown in FIG. 7A, an outer tube 200 is advanced into a tissue wall TW of a uterus tissue surrounding the tumor (e.g., fibroid). In particular, a sharpened distal end of the outer tube 200 can form an entry opening EO through an outer surface of the uterus. In the illustrated embodiment, a free end of the tension member 207 dangles out of a distal opening of the outer tube 200, and can remain at the exterior of the uterus (while yet remaining at an interior of the patient), as the distal end of the outer tube 200 is advanced into the uterine tissue. Once the distal end of the outer tube 200 is in place, as shown in FIG. 7A, the curved needle 202 is pushed through lumen of outer tube 200, until a distal portion 203 of curved needle 202, protruding from outer tube 200, elastically regains a curved shape.

As it is advanced distally, the curved needle 202 forms a passage 204 around a volumetric region VR which includes the tumor (in this example entire tumor can be provided in volumetric region VR although only part of the tumor can be surrounded by passage 204 if needed, in accordance with certain embodiments). Stylet 205 is then pushed distally through curved needle 202 along passage 204 until forming exit opening EX and protruding therefrom outside the uterus tissue (while yet still being within the subject's body) and may thereby complete formation of the passage 204, in case it has not previously been fully formed by curved needle 202. Passage 204 thus may be said to extend from the entry opening EO to the exit opening EX in another portion of the uterus tissue.

Stylet 205 includes means such as a loop 206, at a distal end thereof, configured for facilitating fixation to a tension member 207, which is in the form of a suture wire in the illustrated embodiment. In some embodiments, the stylet 205, or at least the distal end thereof, can be formed of a resiliently flexible material. The loop 206 thus may be held in a low-profile orientation when within a lumen of the curved needle 202, and may expend to the open profile of FIG. 7A when advanced out of the distal end of the curved needle 202. The loop 206 may be compressed back into the low-profile configuration when drawn proximally back into the curved needle 202, which can enhance a grip of the loop 206 on the tension member 207.

Figure 7B:
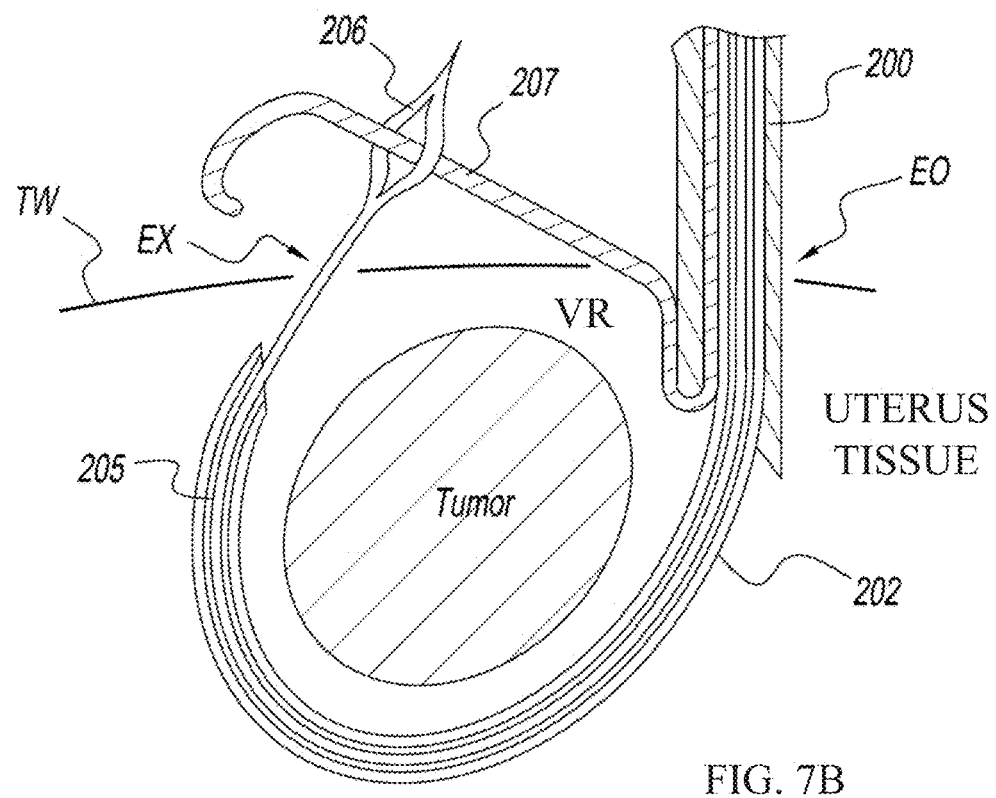

As shown in FIG. 7B, the end portion of tension member 207 that dangled or otherwise extended out of the outer tube 200 in the early stages of the procedure can be coupled to loop 206. For example, the end portion of the tension member 207 can be passed through the loop 206 by an amount sufficient to ensure that the tension member 207 is gripped by the loop 206. In some embodiments, a laparoscopic grasper or other suitable device may be used to manipulate the tension member 207 to thread it through the loop 206.

Figure 7C:
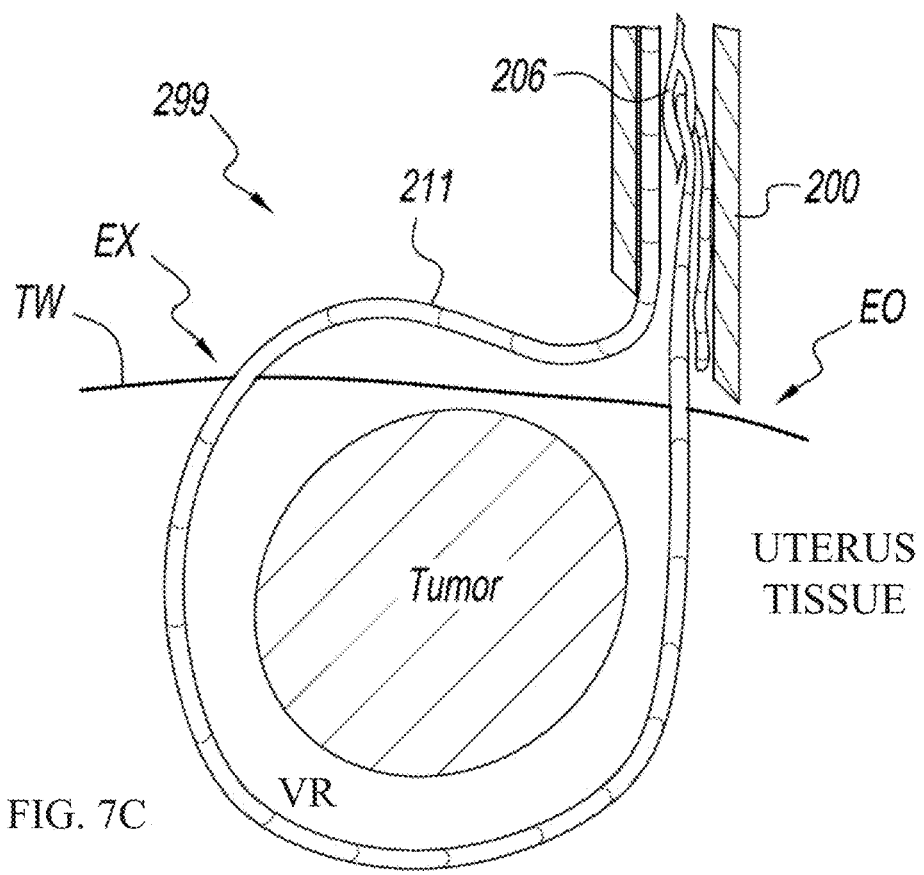
Figure 7D:
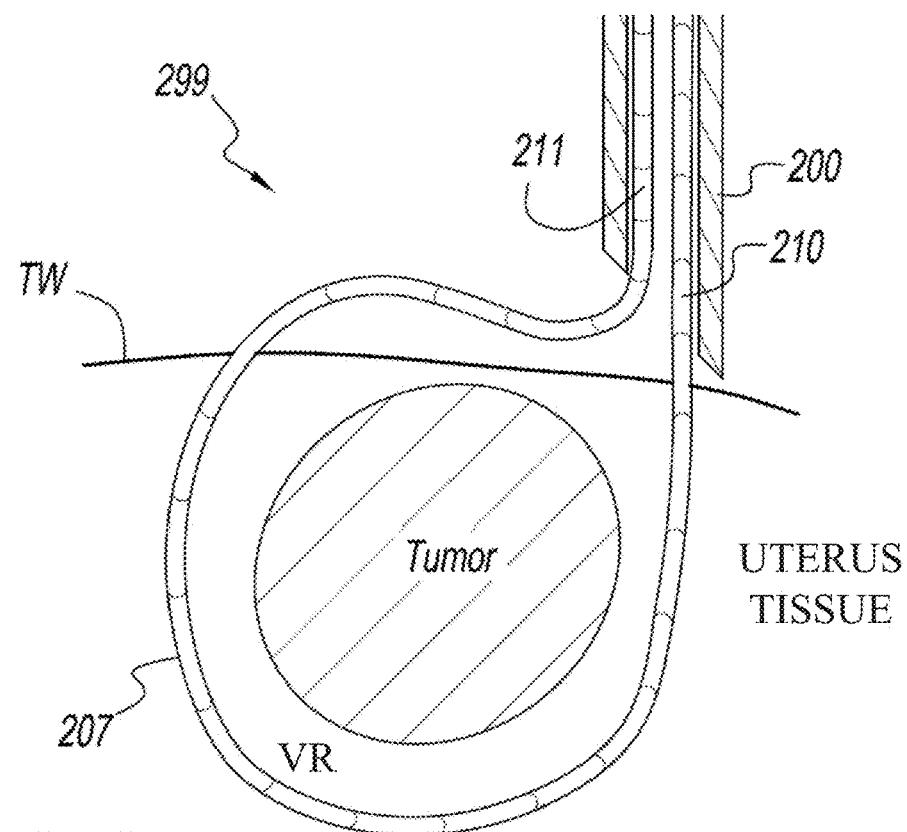

The stylet 205 is then pulled back (in the direction from exit opening EX towards entry opening EO) until loop 206, as coupled with end portion of tension member 207, exits the uterus tissue via entry opening EO into outer tube 200, after passing through passage 204. This action can draw the tension member 207 distally through the outer tube 200, through the passage 204, and back into the outer tube 200 in a proximal direction, such that tension member 207 extends between and through entry opening EO and exit opening EX around volumetric region VR (as shown in FIG. 7C).

Figure 7E:
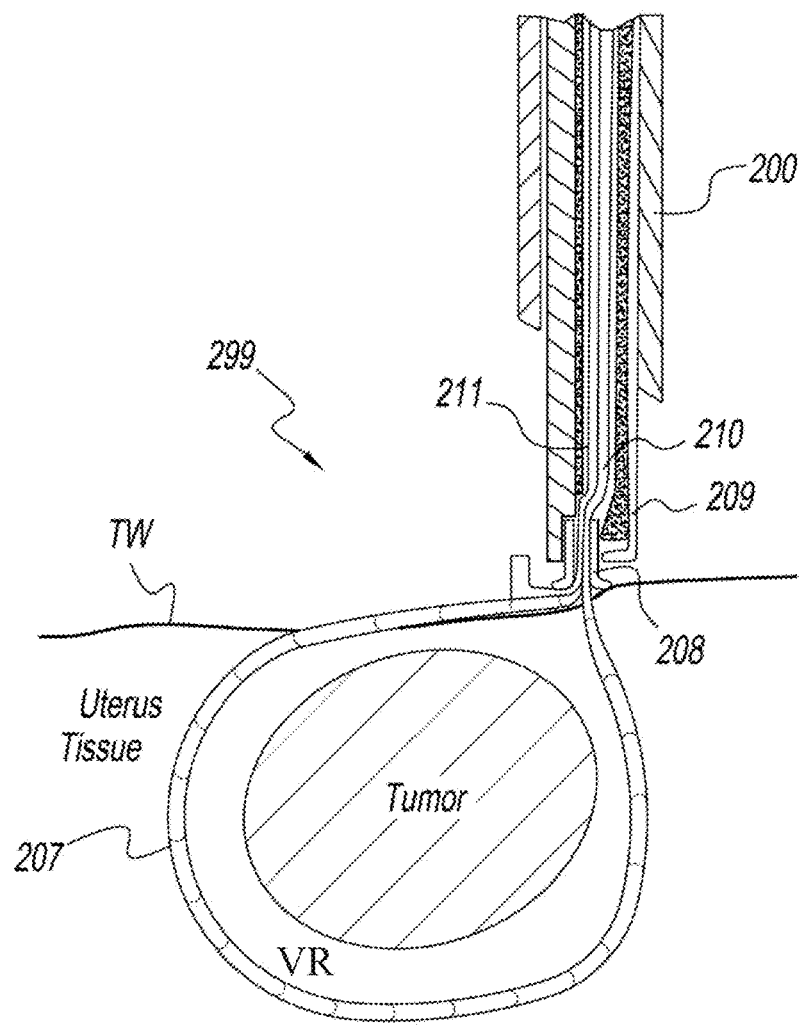
Figure 7F:
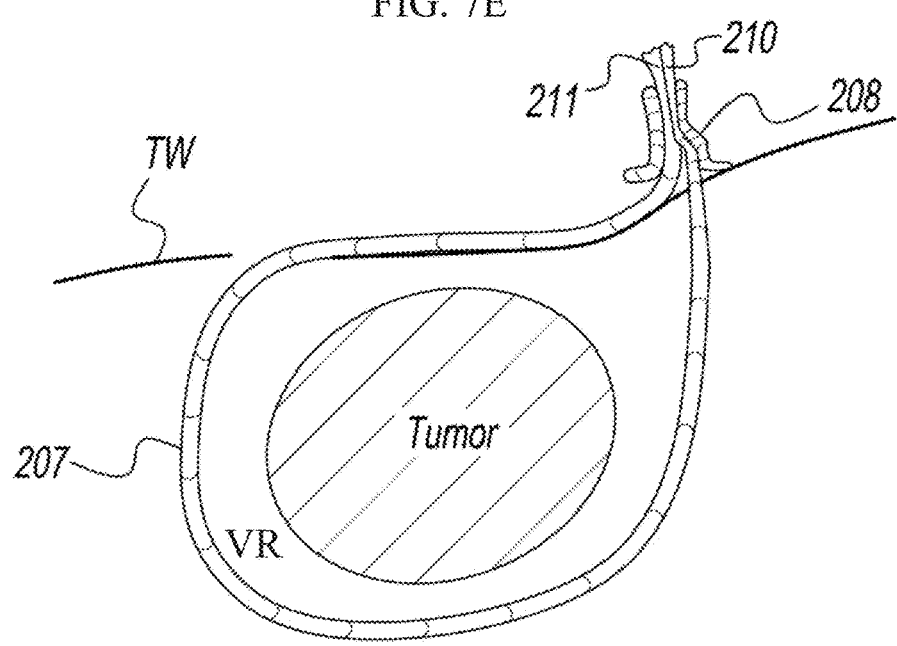

Stylet 205 is pulled completely through the outer tube 200 (FIG. 7D) until a first portion 210 of tension member 207 protruding from entry opening EO, and a second portion 211 of tension member 207 protruding from exit opening EX, are both positioned outside the subject's body. Then, a crimping device 209 carrying a fastener 208, which is configured as a tubular crimping element formed of a ductile material, in the illustrated embodiment, is pushed distally through outer tube 200 and passes over both first and second portions 210 and 211 of tension member 207. Outer tube 200 is pulled back from uterus tissue and crimping device 209 is pushed distally until a distal end thereof protrudes from outer tube 200 in proximity or in contact with tissue wall TW of the uterus tissue that surrounds the tumor (as shown in FIG. 7E). Tension member 207 is then tightened along its length with a chosen tension force, so as to affect radial compression of volumetric region VR for increasing pressure within the tumor. Tightening is made while ductile material 208 is in place or even pushed against tissue wall TW so as to counter the pulling force and achieve the tightening and compressing of volumetric region VR. Once tension member 207 is tightened with the chosen tension force, ductile material 208 is crimped over first and second portions 210 and 211 of tension member 207, using the crimping device 209, thereby securing the first and second portions 210, 211 together and maintaining the desired tensioning force in the tension member 207. As such, the tightening is maintained for ischemia within the volumetric region VR and/or the tumor and eventually necrosis in most or all tissues of the tumor, as previously described.

Figure 8A:
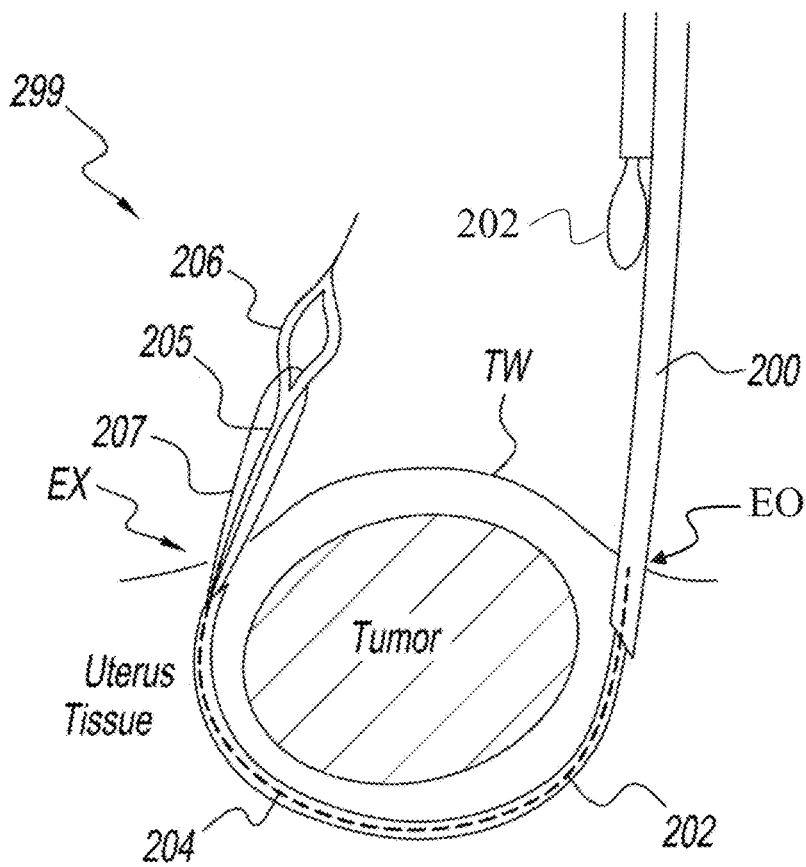
FIGS. 8A-8B schematically illustrate exemplary scenarios representing alternative steps to steps shown in FIGS. 7A-7B, according to some embodiments.
Figure 8B:
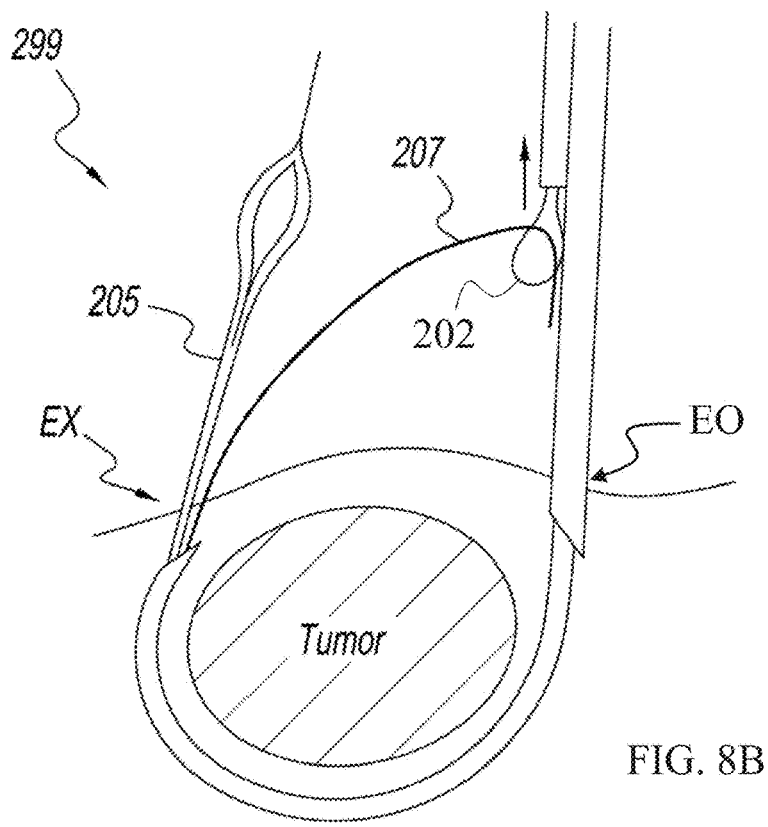

FIGS. 8A-8B schematically illustrate exemplary scenarios representing steps or stages of another method, which may differ in certain respects from steps shown in FIGS. 7A-7B. As previously discussed, in FIGS. 7A-7B, stylet 205 is not initially coupled with the tension member 207, but is coupled therewith after having formed and/or passed through the exit opening EX. Once coupled with the tension member 207, the stylet 205 pulls the tension member 207 along passage 204, first through exit opening EX towards and ultimately through entry opening EO. In contrast, in FIGS. 8A-8B, the stylet 205 is initially coupled with the tension member 207 and advances (e.g., pulls) the tension member 207 with it in tandem as the stylet 205 is advanced along passage 204, first through entry opening EO towards and ultimately through exit opening EX (FIG. 8A). With reference to FIG. 8B, an end portion of tension member 207 is captured with a snare 220 and pulled outside the body. In the illustrated embodiment, the snare 220 is moveable through a second lumen of an elongated member. In particular, the elongated member includes a needle portion, such as previously described first needles, which extends distally relative to a secondary tube. The secondary tube defines the second lumen through which the snare and tension member 207 can pass.

Figure 9A:
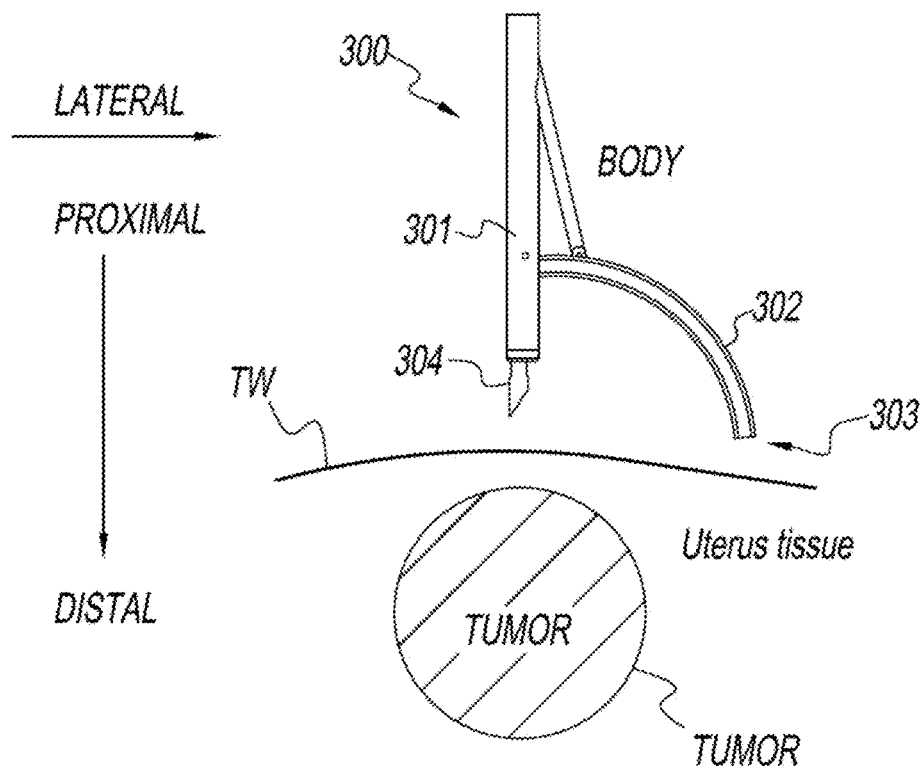
FIGS. 9A-9I schematically illustrate exemplary scenarios representing steps in a method for treating a tumor within a body of a subject, according to some embodiments.
Figure 9B:
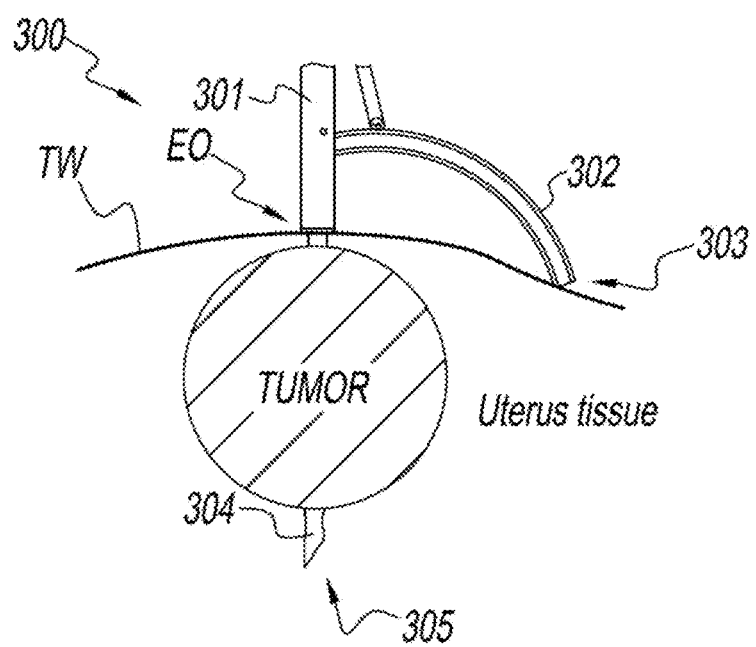
Figure 9C:
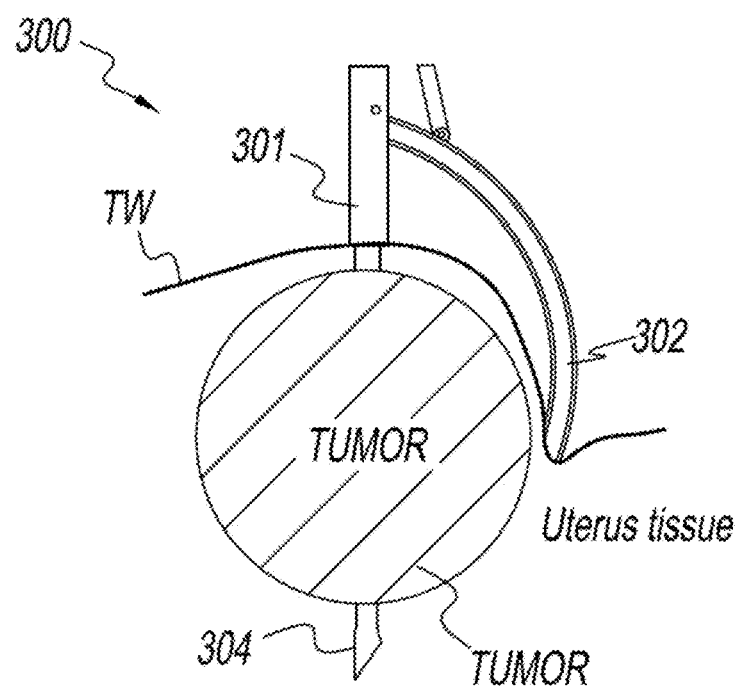

FIGS. 9A-9I schematically illustrate exemplary scenarios representing steps or stages of another illustrative method for treating a tumor. The depicted stages may take place after direct access is formed (e.g., minimally invasively) from outside body of the subject (patient) to the tumor, as shown for example in FIGS. 5A-5F. The minimally invasive access to the tumor may be created by way of transvaginal procedures, endoscopy, laparotomy or laparoscopy. A device 300 for deploying one or more tension members, each in a form of suture wire, is illustrated in FIG. 9A. Device 300 includes a straight central outer tube 301 and a curved lateral outer tube 302. Lateral outer tube 302 is hingedly connected to a lateral portion of central outer tube 301 and is selectively maneuverable between a lateral position, in which a distal end 303 thereof is positioned laterally farthest to central outer tube 301 (as shown in FIG. 9A, for example), and a forward position, in which lateral outer tube distal end 303 is positioned distally farthest to central outer tube 301 (As shown in FIG. 9C, for example). Device 300 also includes a straight central inner needle 304 which extends within central outer tube 301 and has a central needle distal end 305 that is selectively axially extendable or protrusible (and then retractable) along and relative to central outer tube 301. Device 300 further includes a curved lateral inner needle 306 which extends within lateral outer tube 302 and has a lateral inner needle distal end 307 that is selectively axially protrusible (and then retractable) along and relative to lateral outer tube 302. Each one of central outer tube 301, lateral outer tube 302, central inner needle 304 and lateral inner needle 306, is actuatable by an operator independently from the others at least with actuation related to the functions described above. Device 300 with each of its components 301, 302, 304 and 306 is also actuatable from a remote and/or proximal end thereof which can be located outside the body of the treated subject (human patient), such as via a laparoscopic port provided through an abdominal wall.

Figure 9D:
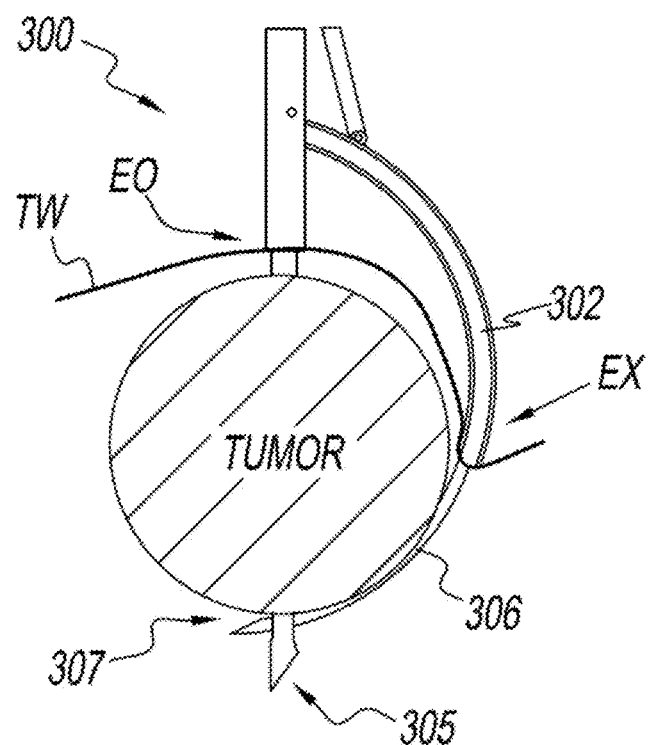

FIG. 9A shows device 300 approaching tissue wall TW of uterus tissue surrounding a tumor (fibroid), when lateral outer tube 302 is in a lateral position and each of central inner needle 304 and lateral inner needle 306 is provided in a retracted configuration. In FIG. 9B, central outer tube 301 is pressing against tissue wall TW above the tumor, and central inner needle 304 is pushed into a protruding configuration such that it penetrates through tissue wall TW and extends fully across the tumor, with distal end 305 thereof positioned beyond the tumor relative to tissue wall TW. Upon penetrating tissue wall TW, central inner needle 304 forms an entry opening EO at tissue wall TW into the uterus tissue and/or directly into the tumor. In FIG. 9C, lateral outer tube 302 is actuated into forward position thereby pressing against a lateral portion of the uterus tissue wall TW located sideway to the tumor, pushing it distally and laterally towards the tumor. In FIG. 9D, lateral inner needle 306 is pushed into a protruding configuration about tumor perimeter, such that lateral inner needle distal end 307 reaches central inner needle distal end 305 in a way which facilitates interaction therebetween. Upon penetrating tissue wall TW, lateral inner needle 306 forms an exit opening EX at tissue wall TW into the uterus tissue.

Figure 9E:
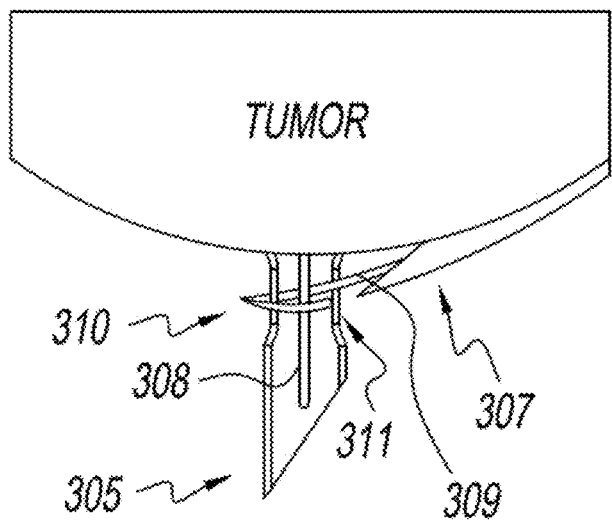
Figure 9F:
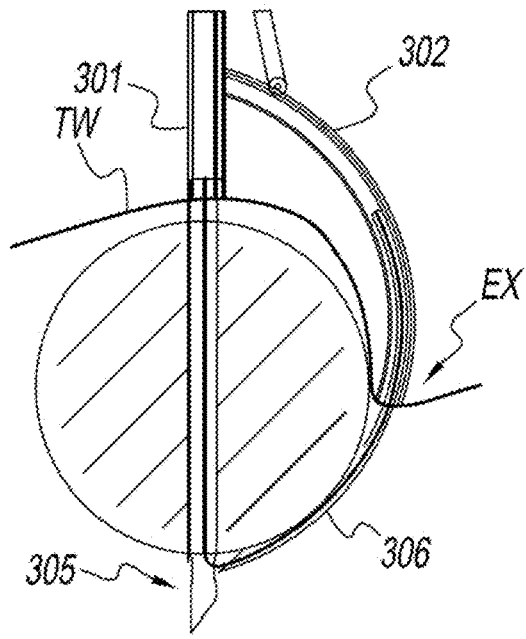
Figure 9G:
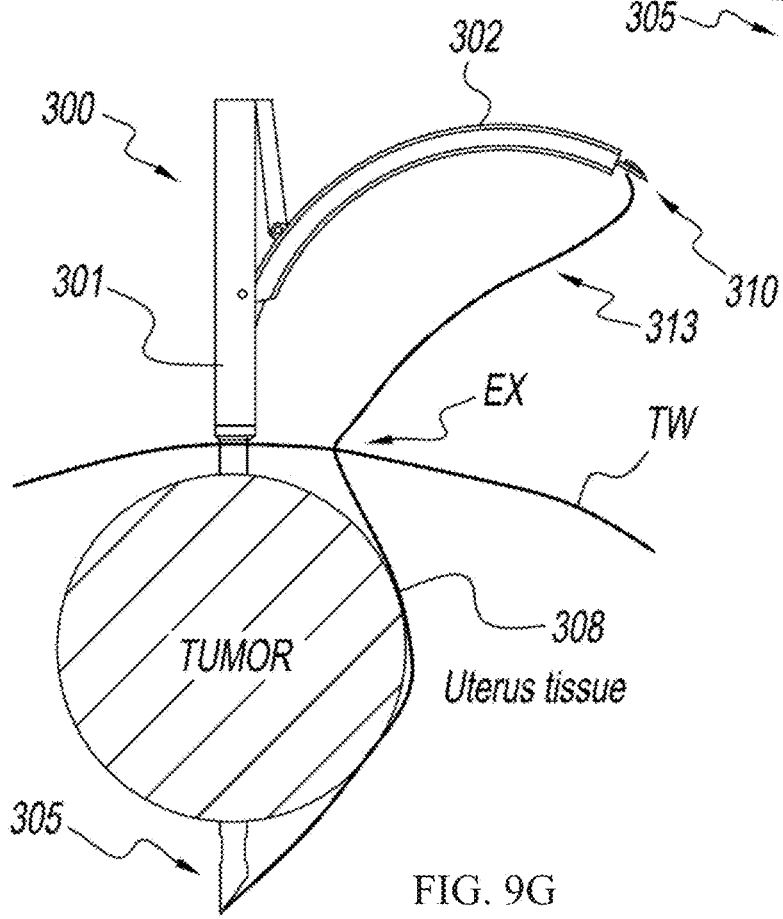
Figure 9H:
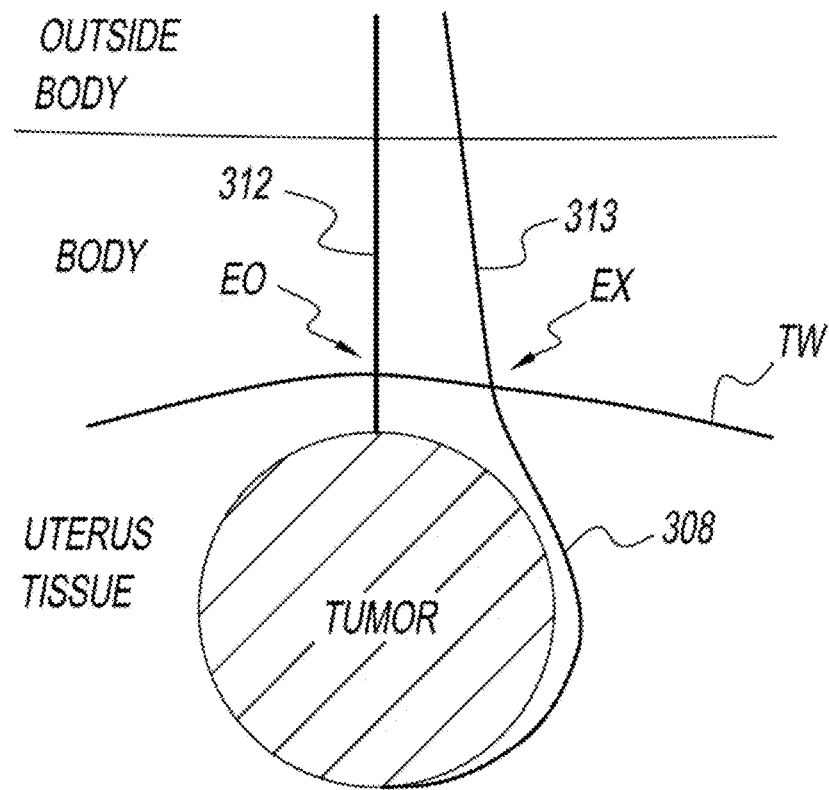
Figure 9I:
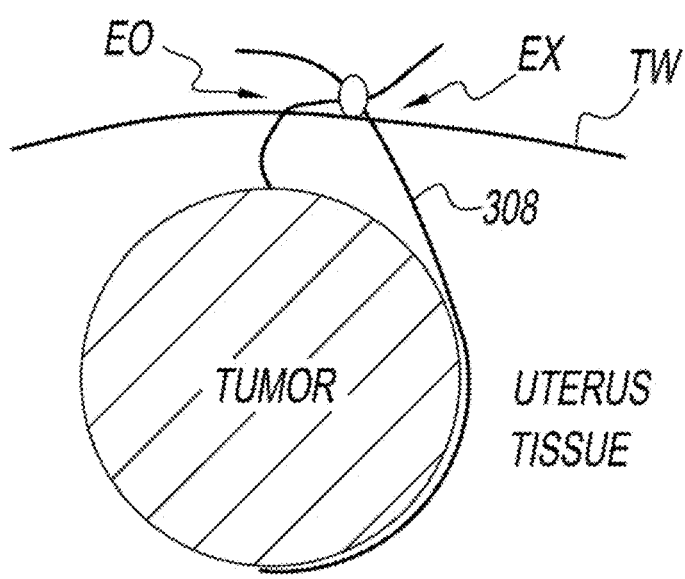

In FIG. 9E, a tension member 308, configured as a suture wire, is passed from outside the subject's body, in a distal direction, within central inner needle 304 until it extends across an entire thickness of the tumor. A stylet 309 carrying a hook 310 at a distal end thereof projects from lateral inner needle distal end 307 for capturing tension member 308. A lateral opening 311 on central inner needle distal end 305 allows hook 310 to pass transversely through lumen of central inner needle 304 and to interact directly with tension member 308 provided inside the lumen. In FIG. 9F, hook 310 is retracted while pulling tension member 308, and lateral inner needle 306 is also retracted into lateral outer tube 302. In FIG. 9G, lateral outer tube 302 is pulled into lateral position further pulling a second portion of tension member 308 via exit opening EX. In FIG. 9H, device 300 is withdrawn leaving only tension member 308 in place, such that it extends through the tumor with a first portion 312 thereof extending out of the uterus tissue via entry opening EO and optionally out of subject's body, and a second portion 313 thereof extending out of the uterus tissue via exit opening EX and optionally out of subject's body. Via the laparoscopic access, the operator (optionally using device 300) tightens tension member 308 and secures (e.g., by way of tying), intracorporeally or extracorporeally, first and second portions 312 and 313 of tension member 308 which maintains tension member 308 taught under a chosen tension force (FIG. 9I).

It is noted that in some instances, other methods previously discussed (e.g., with respect to FIGS. 6A-8B), securement of different portions of the tension member may be achieved intracorporeally, rather than extracorporeally. For example, certain suture-tying and/or suture tightening mechanisms can be employed at an interior of the body, e.g., via a laparoscopic port.

Figure 10A:
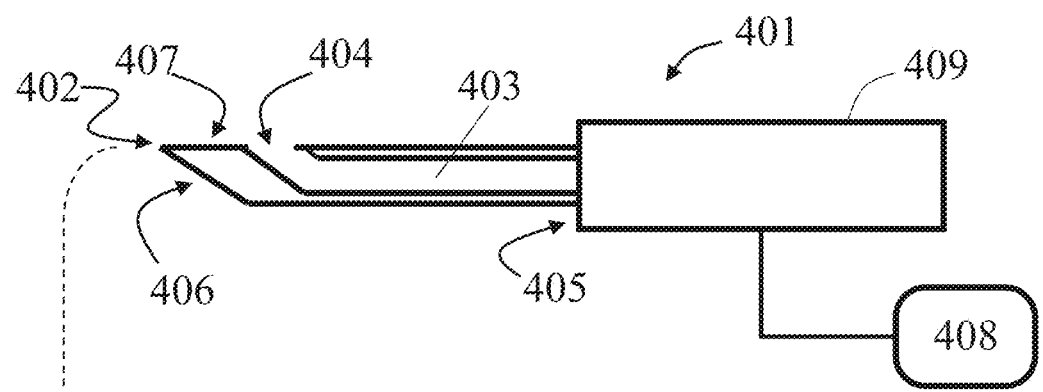
FIGS. 10A-10C schematically illustrate cross-sectional views of components of an exemplary apparatus for passing a tension member around a tissue mass, according to some embodiments.
Figure 10B:
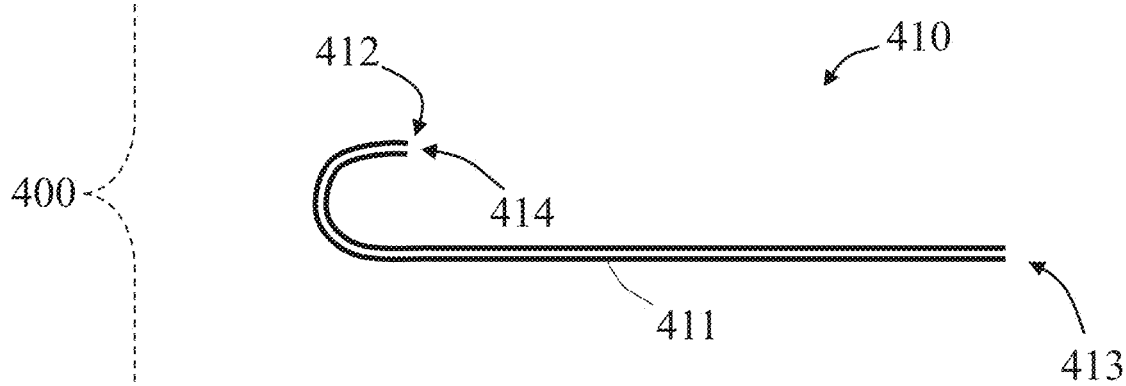
Figure 10C:
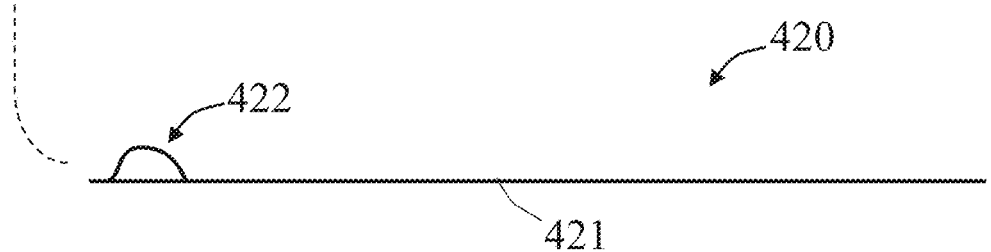
Figure 11A:
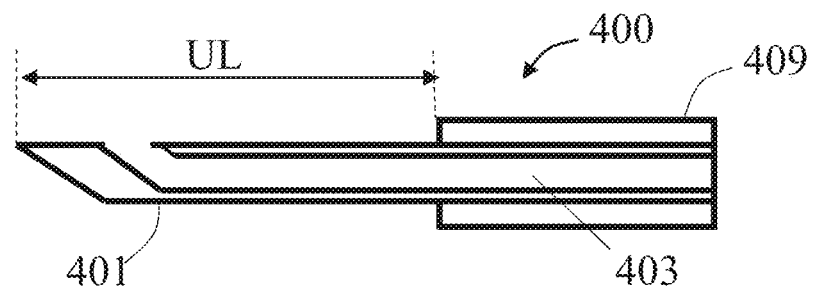
FIGS. 11A-11D schematically illustrate scenarios representing optional steps in an exemplary method for using the exemplary apparatus referred to in FIGS. 10A-10C, according to some embodiments.

FIGS. 10A-10C schematically illustrate cross-sectional views of components of an exemplary apparatus 400 with a suture passing mechanism configured for passing a tension member around a tissue mass. FIGS. 11A-11D schematically illustrate scenarios representing steps or stages in various exemplary methods for using apparatus 400. FIG. 10A shows a rigid outer tube 401 which comprises a sharp outer tube tip 402 and an outer tube lumen 403 opened to an outer tube opening 404 formed as a lateral opening in proximity to outer tube tip 402. Outer tube 401 includes a bevel configured with a bevel face 406 opposing a straight side 407 (relative to longitudinal axis of outer tube 401) that encloses outer tube side opening 404. An outer tube uncovering mechanism 408 is provided with outer tube 401 and configured for fixating a chosen uncovered length UL of outer tube 401 relative to a tube cover 409 covering remaining length of outer tube 401 (as shown in FIG. 11A). Tube cover 409 has a distal boundary 405 (e.g., outer diameter), being wider substantially from boundary (e.g., outer diameter) of outer tube 401, configured to resist penetration of outer tube 401 into soft tissue beyond a depth penetrable with uncovered length UL.

Figure 11B:
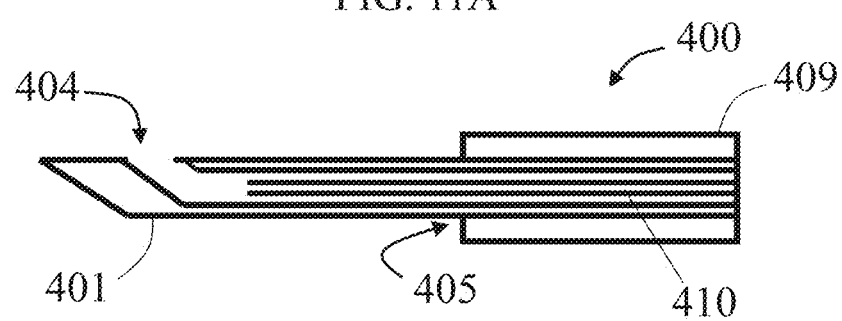
Figure 11C:
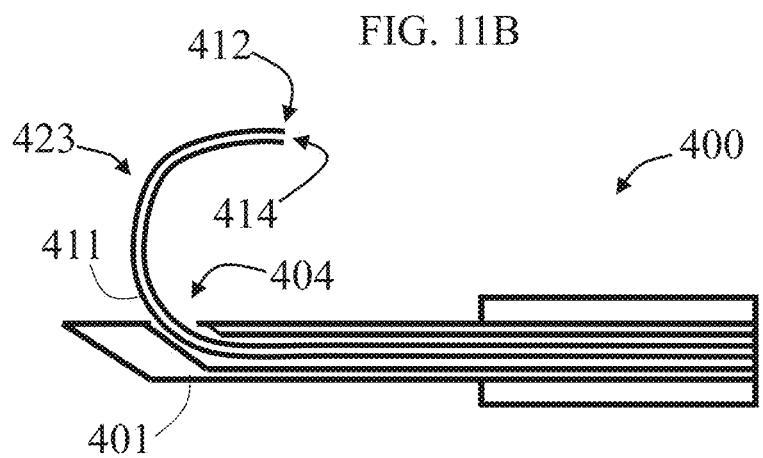

FIG. 10B shows an inner needle 410, in an unstressed relaxed length (in which no external forces or internal stresses are applied in a manner sufficient to deform its size and/or shape, at least not significantly and/or visually), which comprises an elastic needle body 411 ending with a sharp (e.g., beveled, pointed, piercing) needle tip 412 and enclosing an inner needle lumen 413. Inner needle lumen 413 is opened to an inner needle opening 414 in proximity to needle tip 412. Inner needle 410 is configured to pass, while in a straightened configuration, through outer tube lumen 403 due to its flexibility and the constraining rigid boundaries of outer tube lumen 403 achieved by surrounding wall of outer tube 401 (as shown in FIG. 11B). Once inner needle 401 partially protrudes via outer tube opening 404, the protruding portion 423 of inner needle 401 is configured to voluntarily flex (by its elasticity properties) and regain a curved form, as shown in FIG. 11C. When advancing in soft tissue while in its curved form, inner needle 410 is configured to pierce a curved passage around a target tissue mass, by rotationally advancing through the soft tissue surrounding the tissue mass, when pushed via outer tube opening 404.

The apparatus 400 is configured to pass tension members around a tissue mass such as fibroids, which can be of different sizes, shapes and/or depth (relative to surface of an internal body organ, for example). Accordingly, in some instances, it can be advantageous to preset a penetration length, predetermined or from within a range of allowed selectively fixable lengths, which is derived from, and equal to, the uncovered length UL. This measured penetration of outer tube 401 will allow outer tube opening 404 to be positioned near the outer periphery of the target tissue mass, such that the protruding portion 423 of inner needle 410 can be curved beyond and around the distal boundaries of the tissue mass and in proximity thereto. In some embodiments, uncovered length UL is determined in accordance with positioning outer tube opening 404 in proximity to a chosen part of the tissue mass, for example near its middle. Predetermining uncovered length UL may be performed in advance using analysis of invasive or noninvasive imagery.

Figure 11D:
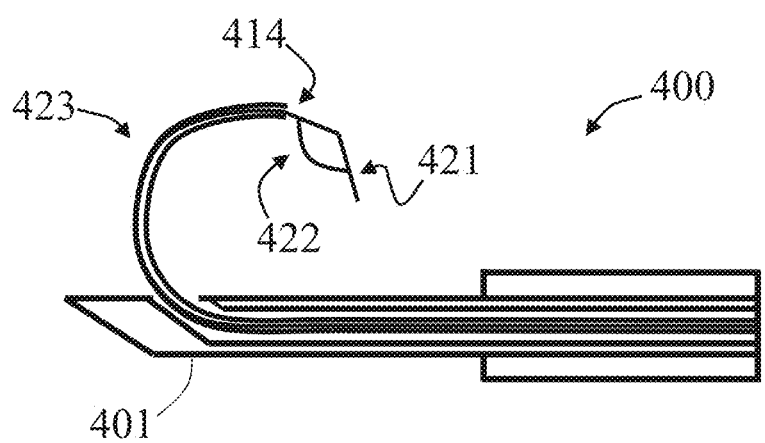

FIG. 10C shows a stylet 420, in an unstressed relaxed state, which comprises a stylet body 421, sized for passing through inner needle lumen 413, and a stylet securing member 422, optionally a wire forming a snare-like structure with stylet body 421, configured for securing a portion of a tension member to the stylet body 421. As shown in FIG. 11D, stylet 420 is advanced through inner needle lumen 413 until stylet securing member 422 protrudes (fully or partially) from inner needle opening 414. As will be described in details below, a tension member can be secured to stylet body 421 with stylet securing member 422, then the tension member can be withdrawn towards and/or into outer tube lumen 403 (via outer tube opening 404) by pulling it with stylet 420, optionally together with inner needle 410.

FIGS. 12A-12I schematically illustrate scenarios representing optional steps in an illustrative method for treating a tumor, shown as a tissue mass TM, that is at least partially within an organ or body region BR of a body of a subject. In various embodiments, the method includes at least the following steps: volumetrically compressing a tumor or a portion thereof within a patient to increase pressure (optionally an interstitial pressure) within the tumor above a threshold level that is sufficient to cause ischemia of the tumor; and maintaining the pressure above the threshold level for a period sufficient to permit at least a portion of the tumor to necrotize due to the ischemia.

The tumor is optionally circumscribed with at least one device of foreign origin relative to the patient, for example a tension member such as a surgical wire, wherein the volumetrically compressing the tumor and maintaining the interstitial pressure are achieved via the at least one device. Each circumscribing step may comprise advancing at least one tensioning member around the tumor at an exterior of a pseudo-capsule that surrounds the tumor. For example, uterine fibroids can be surrounded by a potential space, which may be referred to as a peri-capsular space, which exists between the uterine tissue and the fibroid tissue. Generally, the term "potential space" can apply to a region between opposed surfaces of different types of tissues (e.g., tumor tissue and healthy uterine tissue). Uterine fibroids can be surrounded by a fibroid pseudocapsule, which is a structure that separates the fibroid from uterine tissue. Accordingly, the pseudocapsule can represent an outer extremity of the uterine fibroid, and potential space can exist between the pseudocapsule and the uterine tissue.

The volumetrically compressing is optionally made along at least first and second lines of compression that extend around an outer surface of the tumor along different paths, optionally some or all are nonintersecting paths (see, e.g., FIG. 3I) or alternatively at least some cross at an intersection point (see, e.g., FIG. 3H, where the intersection point is shown at the center of the drawing). The first and second lines of compression may cross at multiple spaced-apart intersection points. For example, in FIG. 3H, due to symmetry, there may be a second intersection point of all of the tension members 10 at an opposite side (e.g., on the non-visible side, in FIG. 3H) of the volumetric region VR. The threshold level of the interstitial pressure may no less than about 2 mmHg, optionally 4 mmHg, optionally within a range of 0.1 mmHg and 10 mmHg.

The method may include circumscribing the tumor with at least one tensioning member along a first path, and along a second path different from the first path. The at least one tensioning member may comprise a single tensioning member looped around the tumor along the first and second paths (see, e.g., FIG. 3K). Optionally or alternatively, a first tensioning member and a second tensioning member are provided, wherein the circumscribing along the first path comprises circumscribing the tumor with the first tensioning member along the first path, and wherein the circumscribing along the second path comprises circumscribing the tumor with the second tensioning member along the second path (see, e.g., FIGS. 3H-3J).

In some illustrative embodiments, a method may include one or more of the following steps: passing a tension member within the organ between an entry opening and an exit opening, each opening being at a surface of the organ, and around a volumetric region that encompasses at least a portion of the tumor; tightening the tension member to cause volumetric compression of the volumetric region, thereby directly increasing pressure within the tumor; and maintaining the increased pressure continuously to achieve ischemic in most or all tissues of the tumor.

The treated tumor is optionally a uterine fibroid, and may be one of intramural, subserous or submucosal with respect to the organ it resides in. Optionally, at least a portion of the tumor is situated intramurally within the organ, and wherein passing the tension member within the organ comprises passing the tension member through an intramural portion of the organ. Passing the tension member through the intramural portion of the organ may comprise passing the tension member around the at least a portion of the tumor that is situated intramurally within the organ. In some such scenarios, passing the tension member within the organ may comprise passing the tension member exclusively through the intramural portion of the organ and/or the tumor between the entry opening and the exit opening.

In order to reach the surface of the organ and treat the tumor, a surgical access to the organ may be first created from outside the body, which may be formed using minimally invasive techniques or by way of open surgery, for example. At least one of the basic method steps (passing, tightening, and maintaining) can be performed via the surgical access.

The entry opening can be located at a first location on or adjacent to the tumor and the exit opening can be located at a second location on or adjacent to the tumor spaced from the first location, such that the tumor is located between the entry and exit openings.

Prior to passing the tension member, a passage can be formed around the volumetric region between the entry and exit openings, optionally also forming the entry and exit openings, such that the passing can be performed mostly or entirely within the passage, optionally by way of pulling the tension member via the exit opening towards the entry opening. The passage may be formed using apparatus 400 or any other applicable apparatus or mechanism. For example, an outer tube can be used to create the entry opening and positioned through the entry opening into the organ, in proximity to the tumor. A curved needle can then be advanced through a lumen of the outer tube around the volumetric region.

The volumetric portion may be predetermined by a user (practitioner, physician, surgeon, etc.) and passing the tension member may be performed in close fit to and around the volumetric portion. Determining the volumetric portion may include determining entry and exit points to and from the organ in relation to the tumor, and possibly also a particular plane crossing the tumor and the entry and exit points. Passing the tension member may be along a predetermined passage line between the entry opening and the exit opening. The passage line optionally projects across one or more blood vessels feeding the tumor, such that the tightening of the tension member directly causes occlusion of the blood vessels, such as previously discussed.

Passing the tension member may include encompassing more than half a circumference of the tumor with the tension member, and/or it may include winding the tension member or a plurality of additional tension members along separate paths and/or planes around the volumetric region. In case of an additional volumetric region encompasses at least another portion of the tumor, passing the tension member may also include deploying a plurality of windings around the additional volumetric region. The volumetric region optionally encompasses most of a volume of the tumor, or its entirety.

In various embodiments, tightening the tension member is performed in an effort to achieve a chosen tensioning force, optionally a predetermined tensioning force. The tensioning force applied to the tension member and/or the pressure within the tumor may be measured at least during tightening of the tension member.

Tightening of the tension member may be performed using a tightening device, which can optionally be removed from the body before and/or during the phase of maintaining the increased pressure within the tumor. The pressure within the tumor, upon the increase in pressure, may be above capillary blood pressure of blood vessels oxygenating the tumor, thereby diminishing or preventing transfer of oxygenated blood to tissues of the tumor and gradually causing the ischemia. The volumetric compression is optionally maintained continuously at least until achieving necrosis in most or all tissues of the tumor. Optionally the tension member and a plurality of additional tension members are tightened to collectively apply radially compressive force toward a center of the tumor.

Tightening the tension member may include or be followed by securing a first portion of the tension member protruding from the entry opening to a second portion of the tension member protruding from the exit opening, so as to facilitate the maintaining of the increased pressure. Securing together the portions of the tension member optionally includes coupling a fastener to the first and second portions of the tension member to maintain the tension member in a tightened state. The fastener optionally comprises a ductile material and securing the tension member then includes crimping the fastener around the first portion and the second portion of the tension member. Securing the tension member portions is optionally performed outside boundaries of the organ, optionally from outside the body through the surgical access, and may be performed using the tightening device or a separate device.

The tension member optionally comprises a flexible strip or a wire, such as a suture wire, and may be formed of at least one of implant-grade metal alloy, implant-grade polymer, implant-grade textile, and biodegradable material. In certain embodiments, the tension member is configured with a yield strength or a maximal tension force of at least 25 N (newtons) in order not to prevent failing during tumor compression. Optionally the tension member is configured to yield above about 80 newton or about 100 N (newton) before it can cause cutting in organ tissues resulting from tumor compression by the tension member. Optionally, the tension member is formed as a biodegradable suture wire and is configured to yield under tensioning forces below 25 N (newtons) after the tumor tissues are ischemic or necrotic, for example after a few weeks or months.

With further reference to FIGS. 12A-12G demonstrate an various stages of an illustrative method of passing a tension member, configured as wire (e.g., suture) 430, around a tumor TM within an organ ORG. FIGS. 12H-12J demonstrate stages of an illustrative method of compressing the tumor TM above a chosen pressure, and maintaining compression, by way of tightening one or more of tension member 430, in one or more windings, around tumor TM, and securing together a first and a second portions of tension member 430 while being tightened under tightening force. Performing the tension member passing around tumor TM may be carried out using a suture passing mechanism such as apparatus 400. Performing tightening (and/or compressing) and securing (and/or maintaining) may be carried out using separate mechanisms within same apparatus or via separate apparatuses, optionally within apparatus applicable for the suture passing (e.g., apparatus 400).

Figure 12A:
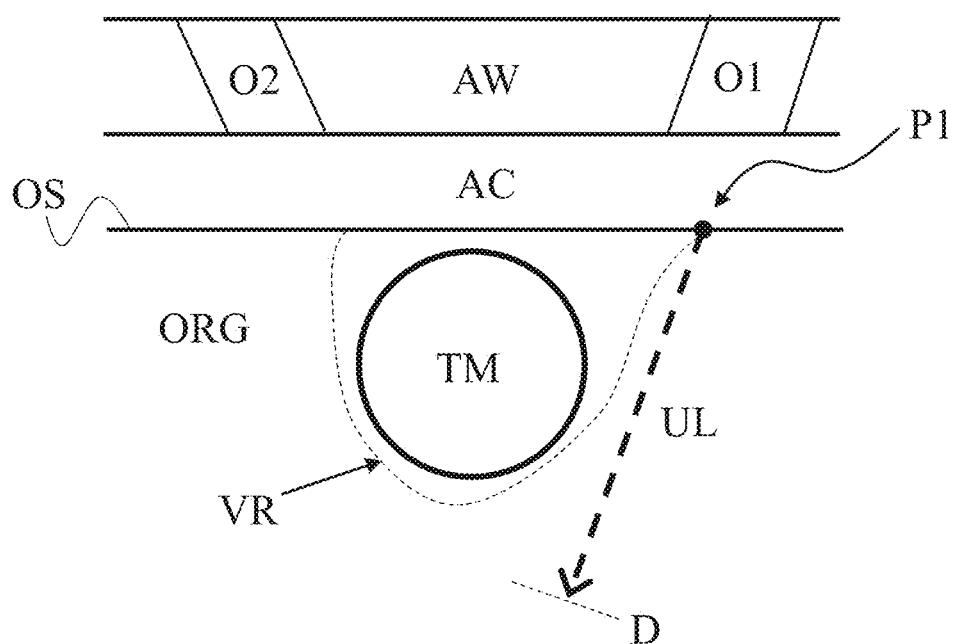
FIGS. 12A-12J schematically illustrate scenarios representing optional steps in an exemplary method for causing ischemia in a tumor, according to some embodiments.

FIG. 12A illustrates an exemplary scenario in which at least two surgical (e.g., minimally invasive or laparoscopic) access openings O1 and O2 are formed to an abdominal wall AW for creating separate passages into an abdominal cavity AC and therethrough to an outer surface OS of organ ORG (e.g., a uterus). Either one of surgical access openings O1 and O2 may be a transcutaneous cut or a fixed passage maintained by an artifact such as a trocar or a cannula.

As an optional preliminary step, the user (surgeon, practitioner, etc.) may determine a desired orientation for a tension member to pass within organ ORG with respect to tumor TM. Such a calculated, selected, and/or predetermined orientation may be spatial or two-dimensional. The user may determine an at least one volumetric region VR which encompasses at least a portion of tumor TM. Optionally, alternatively or additionally, the user determines a plane crossing or passing through tumor TM on which points of entry and exit to and from the organ ORG will be made. Optionally, a penetration depth D is defined, taken from an entry point P1 at surface OS relative to boundaries of tumor TM.

Figure 12B:
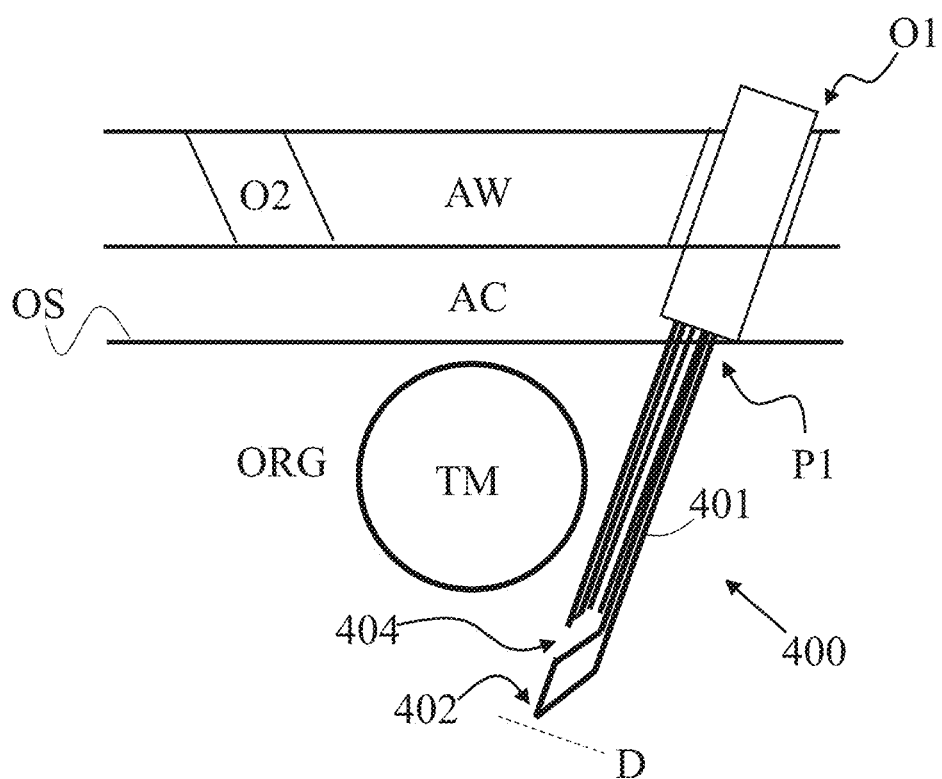

A suture passing mechanism, optionally part of apparatus 400, is then put into use. In some instances, a chosen uncovered length UL of outer tube 401 is first set or fixated, which uncovered length UL can be substantially equal to penetration depth D, by adequately withdrawing tube cover 409 (as described above). Apparatus 400 is then passed via first laparoscopic opening O1 and then pressed with sharp outer tube tip 402 at a chosen direction against surface OS until penetrating the soft tissue of the organ ORG in proximity to tumor TM (FIG. 12B). By doing so, tip 402 forms entry point P1 and a first segment of a surgical passage within organ ORG around tumor TM and/or volumetric portion VR. Apparatus 400 is pushed distally until outer tube tip 402 reaches the predefined penetration depth D, or possibly slightly beyond it, or until outer tube opening 404 is positioned a chosen distance (e.g., a chosen proximal distance) from a distal boundary of the tumor TM. For example, the opening 404 may, in some instances, desirably be positioned at a depth that corresponds to about the middle of tumor TM (i.e., a distance substantially equal to the radius of tumor TM, as spaced from a distal boundary of the tumor). In some embodiments, apparatus 400, or particularly outer tube 401 and/or inner needle 410, is of a chosen size out of a variety of sizes, such that the length between outer tube opening 404 and outer tube tip 402 is about the size of tumor TM radius. In such embodiments, penetration depth D will be determined so that if outer tube tip 402 is in proximity to distal boundary of tumor TM then outer tube opening 404 is also in proximity to middle of tumor TM.

Stated otherwise, in some instances, a plurality of inner needles 410 may be provided. Each needle 410 may have has a pre-curved region with a length and/or radius of curvature that differs from the lengths and/or radii of curvature of the remaining options. A user may choose one inner needle 410 out of the available plurality that will form a passageway of a desired shape, size, and/or orientation around the tumor. In some instances, the outer needle 401 is provided separately from one or more of the inner needles 410. In other instances, the outer needle or tube 401 and a plurality of inner needles 410 are provided together (e.g., are provided in a unitary kit).

Figure 12C:
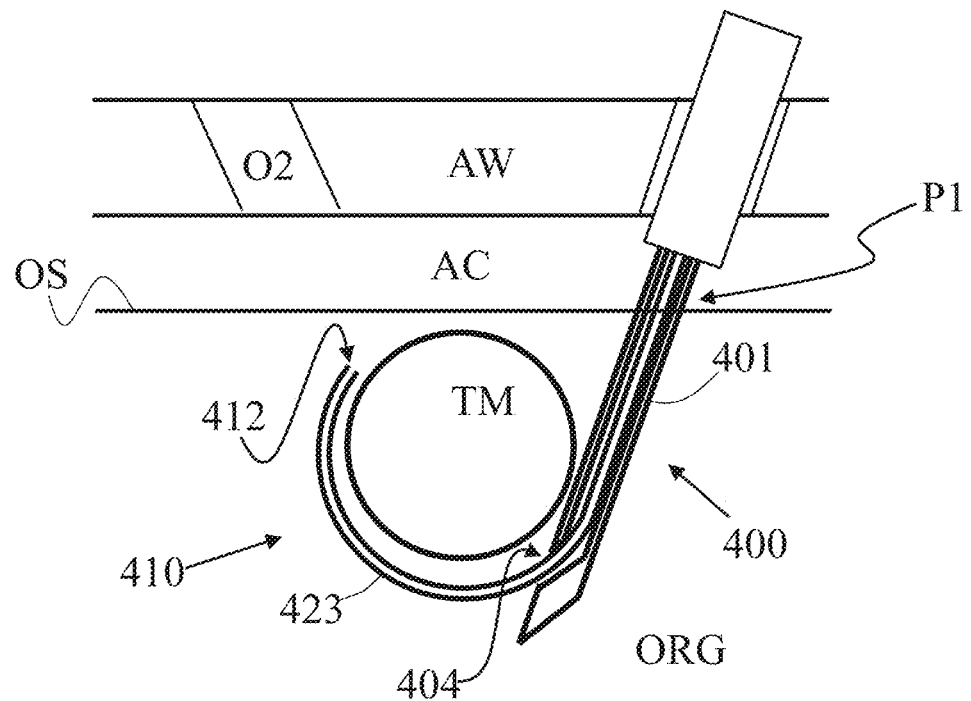

As shown in FIG. 12C, inner needle 410 can then be passed in outer tube lumen 413 in a travel length sufficiently for extending protrusion portion 423 in a chosen protrusion length via outer tube opening 404. Accordingly, by pushing inner needle 410 via outer tube opening 404, the surgical passage made in organ ORG is extended with a curved segment pierced with needle tip 412 around volumetric region VR and/or tumor TM, along span of protrusion portion 423. As described above, protruding portion 423 naturally flexes from a straightened form to regain a preformed curved form; and the curved portion can advance along a curved path through soft tissue surrounding the tumor TM so as to facilitate formation of (e.g., via piercing through tissue) the curved passage segment.

Figure 12D:
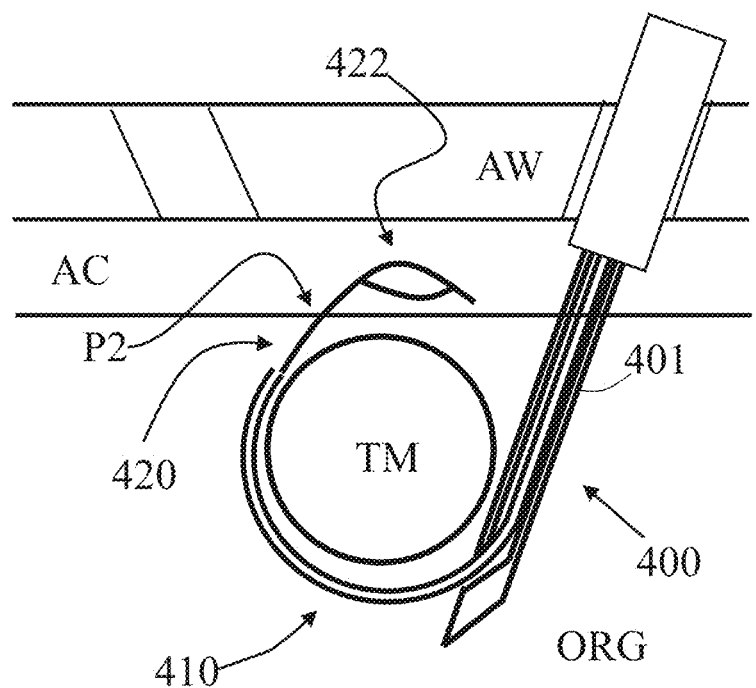

After formation of the curved portion of the path via the inner needle 410, the stylet 420, which may optionally be pre-loaded within the inner needle 410, is advanced through inner needle lumen 413 and out of inner needle opening 414 until the securing member 422 portion exits organ ORG at an exit point P2, which can be spaced from (e.g., opposingly located relative to) entry point P1, relative to tumor TM (FIG. 12D). Stated otherwise, the entry and exit points P1, P2 may be at opposing sides of the tumor along a surface of the organ (e.g., uterus). As described above, location of exit point P2 can be predetermined or at least selected or determined in advance in correlation with distance and orientation of inner needle tip 412 relative to internal body region outer surface OS. In some instances, it can desirable for the exit point P2 to be within a range of 2 cm to 5 cm from the entry point P1 in order to: keep both points P1, P2 within the user's visual range (e.g., using an endoscope or camera positioned in abdominal cavity AC via a separate channel or surgical opening); in some instances, sufficiently distant from adjacent organs which can be harmed if unintentionally penetrated; and/or effectively tension both ends of tension member 430 around tumor TM which ends of the tension member 430 will ultimately emerge from points P1 and P2, as shown in FIG. 12G, for example.

Figure 12E:
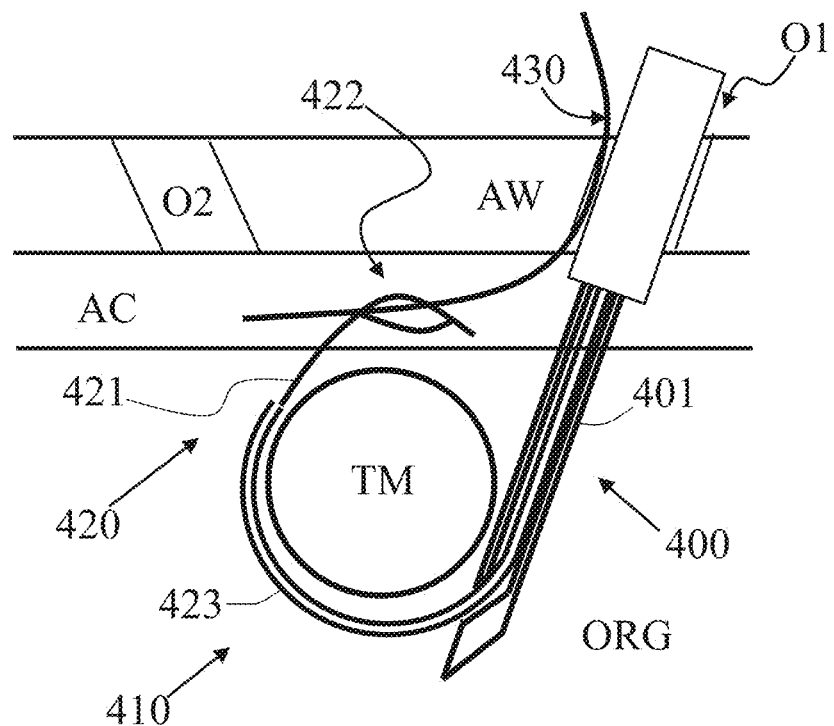
Figure 12F:
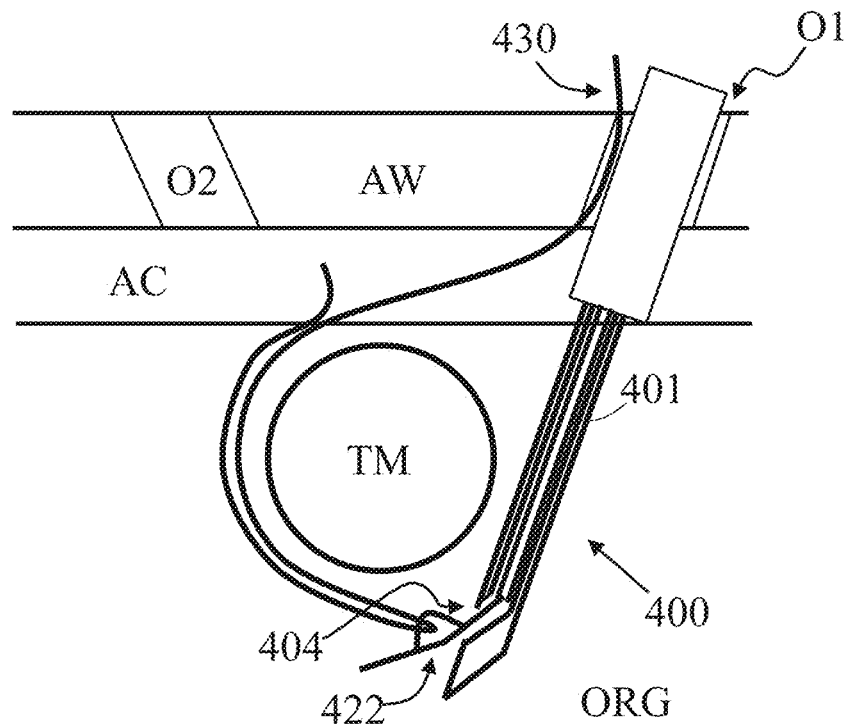
Figure 12G:
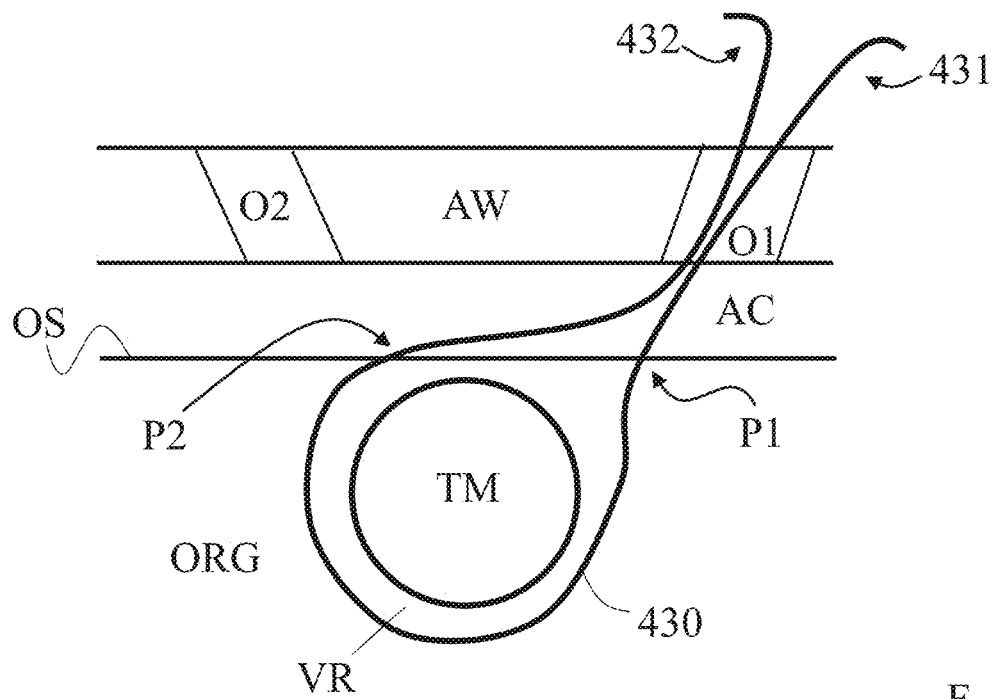
Figure 12H:
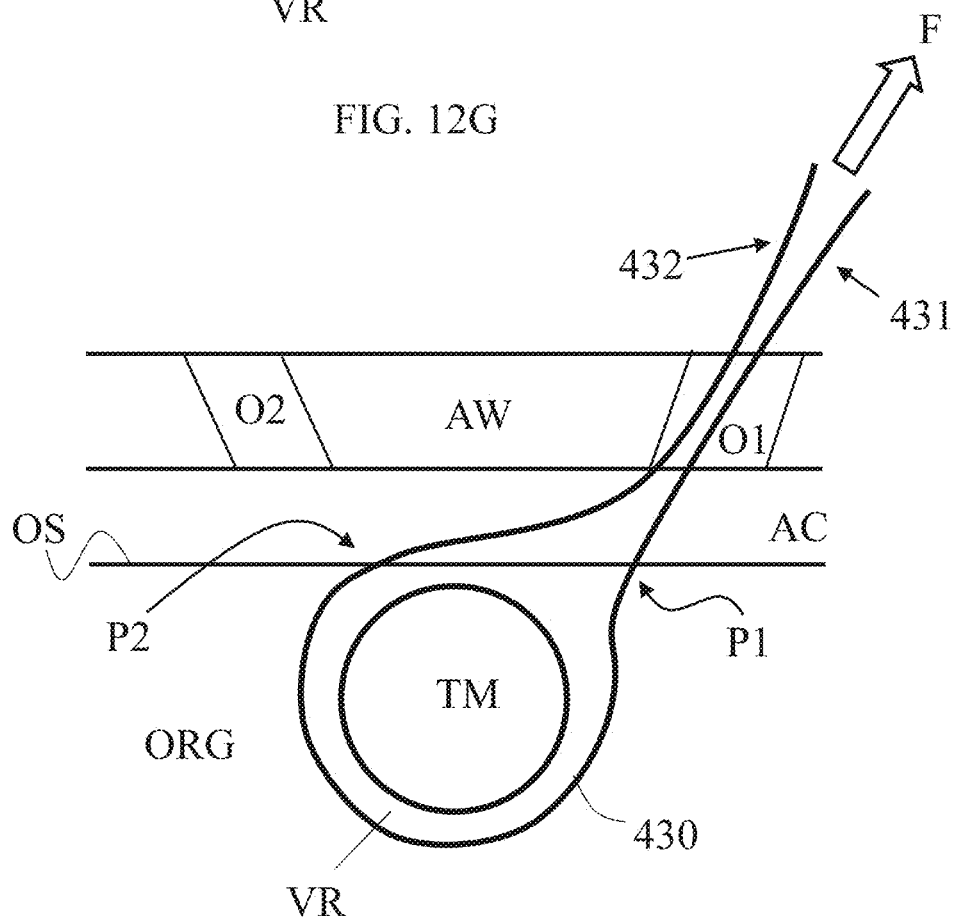
Figure 12I:
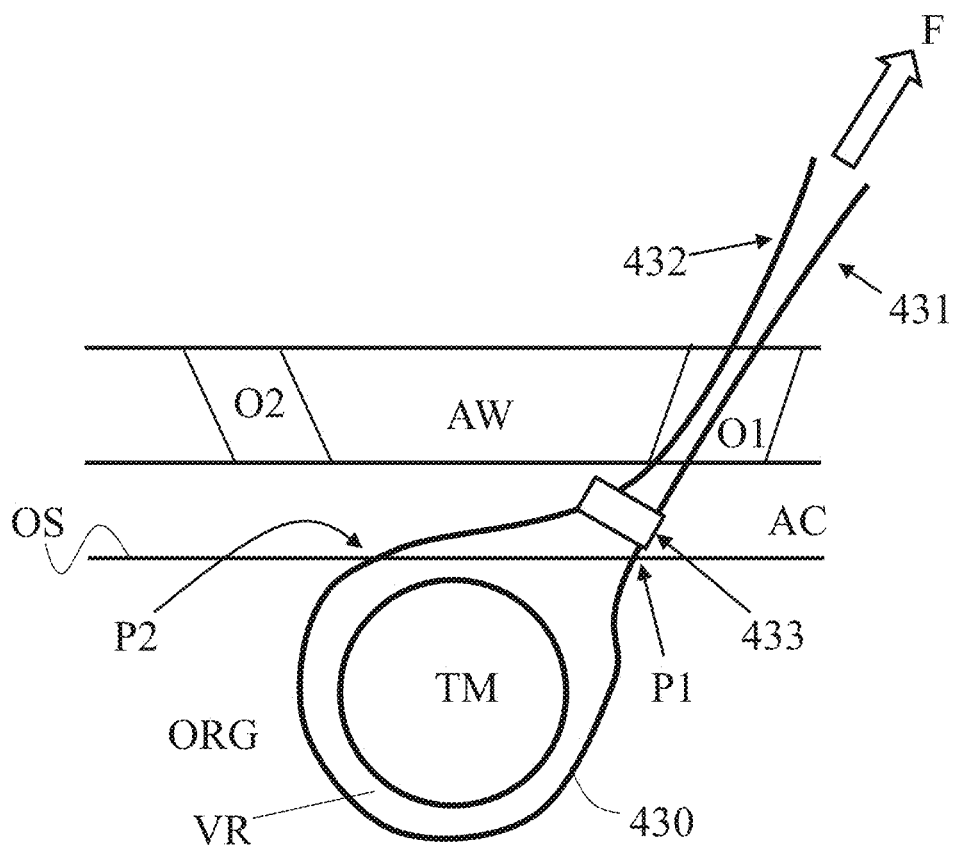
Figure 12J:
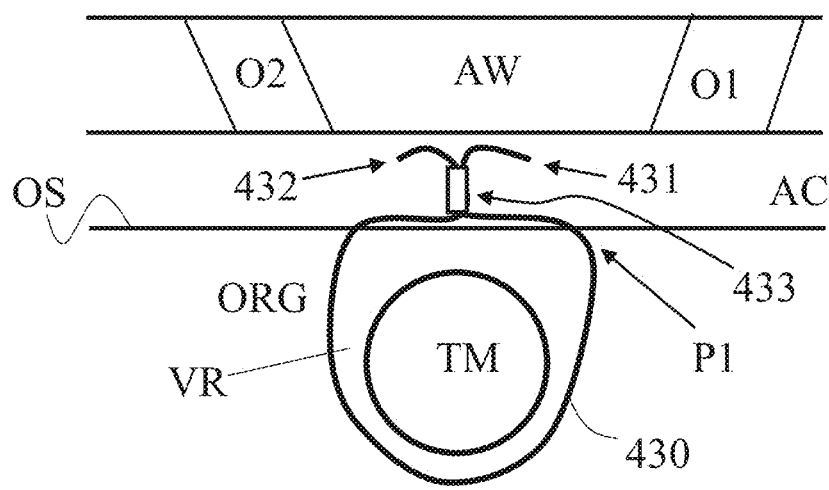

In certain embodiments, tension member 430 is inserted into abdominal cavity AC through first or second surgical opening O1, O2 (in this example, first opening O1, alongside, through or with apparatus 400) as shown in FIG. 12E. A portion of tension member 430 is then passed through the lumen of securing member 422, optionally using a surgical tool such as surgical grasper which may be operated via second opening O2. The tension member 430 therefore can be coupled or secured to stylet body 421 and drawn towards and/or into inner needle lumen 413 and/or outer tube lumen 403, by pulling stylet 420 with tension member 430 secured thereto (FIG. 12F). In some instances, a grip of the securing member 422 on the tension member 430 can increase or be enhanced as the securing member 422 is drawn into the lumen of the tube 401 and/or the inner needle 410, as a loop formed thereby may be resiliently compressed when passing into or through the lumens thereof.

Apparatus 400 is then pulled out from organ ORG while drawing the captured tension member 430, and then removed from patient's body. As a result, the tension member 430 can be left extended around volumetric region VR and/or tumor TM, such that one portion 431 of tension member 430 extends from entry point P1 through abdominal cavity AC and out of patient's body, and another portion 432 of tension member 430 extends from exit point P2 through abdominal cavity AC and out of patient's body (FIG. 12G). The two portions 431 and 432 of tension member 430 can be further manipulated from outside the body for the next steps of that method that includes tightening (and/or tumor compressing) and securing (and/or maintaining tumor compression) of tension member 430.

Optionally, for performing tightening and securing of the tension member 430, apparatus 400 is withdrawn and replaced with a single apparatus or separate apparatuses comprising a tightening mechanism for tightening tension member 430 and a securing mechanism for securing (e.g., fastening) together first and second portions 431 and 432 of tension member 430, for maintaining a chosen tightening force therein and through for continuously compressing volumetric region VR and/or tumor TM.

As shown in FIG. 12H, tension member 430 is tightened around volumetric region VR and tumor TM by applying a chosen tightening force F, optionally applied from outside of patient's body. Force F may be applied through one of, or both, portions 431 and 432 of tension member 430. In some embodiments, before, during, or after reaching a chosen tightening force F, a fastener 433 is applied over both ends and passed over portions 431 and 432 of tension member 430 into abdominal cavity AC until being positioned in proximity to entry and exit points P1 and P2 (as shown in FIG. 12I). By pushing fastener 433 towards organ ORG and applying tensioning force F to tension member 430, compression forces are applied to volumetric region VR and to tumor TM, which increases pressure in the tumor and optionally compresses tumor TM and/or its surrounding soft tissue. Once reaching a chosen pressure in tumor TM (e.g., correlated to force F magnitude or measured directly from the tumor), fastener 433 can be crimped over first and second portions 431 and 432 of tension member 430 (FIG. 12J), thereby maintaining the compressive forces applied to tumor TM, even when releasing tension member 430. Residual length of suture 430 can be trimmed and removed as needed or desired. In some instances, the suture 430 can be made of biodegradable or bioresorbable material and left implanted indefinitely.

In some instances, the fastener 433 can be formed of a non-bioresorbable material and may likewise be left implanted indefinitely, e.g., may be left within the patient after having closed a surgical access site. The fastener 433, being non-bioresorbable, may in some instances remain within the patient in integrated form longer than the tension member 430. Some or all steps may be repeated for the same fibroid, and each repetition may be performed using a different implanted device (tension member) around the same volumetric region, but along a different plane or spatial orientation and/or via different entry and exit points. In other or further instances, some or all steps may be repeated for one or more additional fibroids, in like manner.

A plurality of tension members circumscribing tumor TM, each provided along a different tumor crossing plane (as shown in FIGS. 3A-3K, for example) and maintained tightened at a chosen magnitude, can cumulatively cause a chosen volumetric (e.g., spherical) compression to tumor TM, thereby increasing pressure (e.g., homogeneously increasing pressure) therein to a degree known or tested (in-vivo or in-vitro, for example) to cause local ischemia. In some embodiments, the increased pressure increases local interstitial fluid pressure in tumor TM and/or in volumetric region VR to a degree being sufficient to suppress or cease flow of interstitial fluid to the tumor and surrounding host tissues. In some embodiments, the increased pressure in tumor TM and/or volumetric region VR is sufficient to suppress or cease tissue oxygenation from associated blood vasculature of the tumor and surrounding host tissues. In some embodiments, the tension member(s) is/are biodegradable and configured to autonomously yield and then dissolve after a period of time sufficient for naturally occurring necrosis of the organ and/or tumor tissues resulting from the continuous ischemia-causing compression affected by the tightened tension-member(s).

Figure 13:
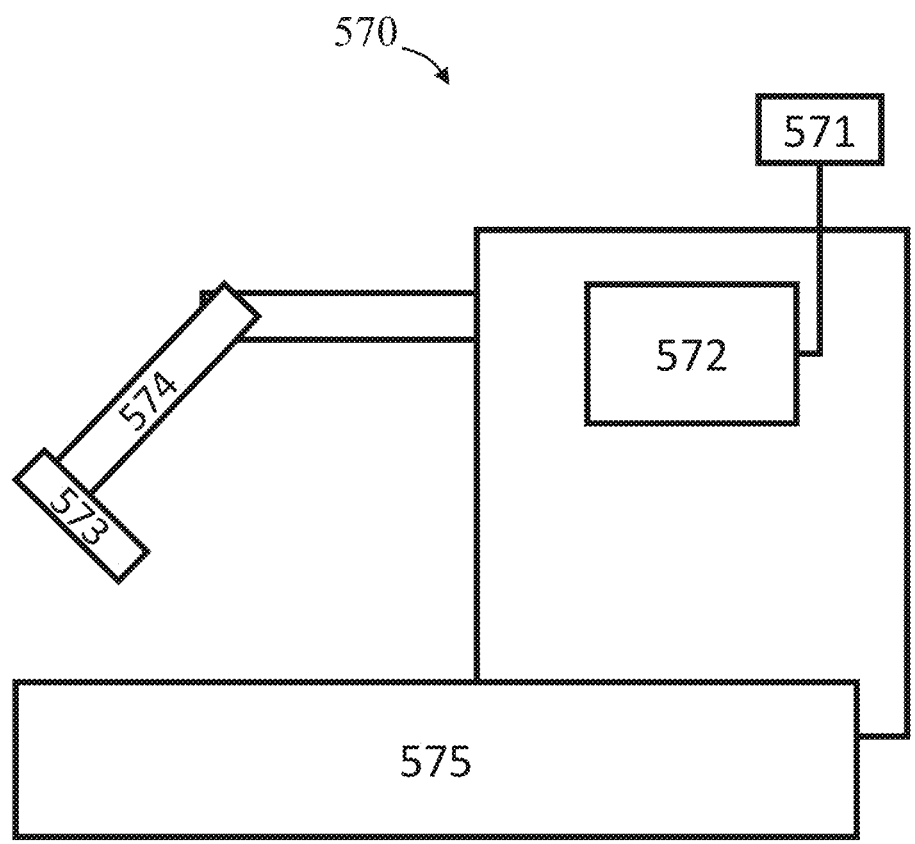
FIG. 13 schematically illustrates an exemplary robotic system, according to some embodiments.

FIG. 13 schematically illustrates an exemplary robotic system 570 comprising a tension member passing mechanism that includes one or more structural and/or functional features or components of apparatus 299, apparatus 300 or apparatus 400, for example. In some embodiments, robotic system 570 is programmed, programmable, or is configured to be remotely applied by a user, for executing methods or parts thereof according to this disclosure, including but not limited to method 50. In some embodiments, robotic system 570 is manipulated selectively using a power source 571 via a computerized controller 572. In some embodiments, the tension member passing mechanism and/or additional mechanisms are housed and operated from within a robotic arm end-effector 573 connected to a robotic arm 574. In some embodiments, robotic arm end-effector 573, and some or all mechanisms housed therein, is operatively connected to a bed unit 575 that may be controlled by robotic system 570 and/or provide information and/or feedback signals to implement automatic and/or remote procedures using either one of the housed mechanisms, including the tension member passing mechanism.

Following are various illustrative examples, each of which is a separate embodiment. This disclosure further includes all permutations of the "independent" examples below with their "dependent" examples. Moreover, additional embodiments capable of derivation from the independent and dependent examples that follow are also expressly incorporated into the present written description.

EXAMPLES

Example 1

A method for treating a tumor that is at least partially within an organ of a body of a subject can comprise: passing a tension member within the organ between an entry opening and an exit opening, each opening being at a surface of the organ, and in close fit around a predetermined volumetric region that encompasses at least a portion of the tumor; tightening the tension member to cause compression of the volumetric region, thereby directly increasing a pressure within the tumor; and maintaining the increased pressure such that most or all tissues of the tumor undergo ischemic resulting directly from the compression caused by the tightened tension member.

In various embodiments, the passing includes winding the tension member and/or a plurality of additional tension members along separate paths around the volumetric region. In various embodiments, each of the separate paths fully circumscribes the tumor. In various embodiments, each separate path defines a separate plane that extends through the tumor. In various embodiments, the separate planes intersect along a line that passes through the tumor. In various embodiments, wherein the separate planes intersect along a line that is external to the tumor. In various embodiments, the separate paths intersect at one or more points. In various embodiments, the one or more points of intersection are external to the tumor. In various embodiments, the tightening includes tightening at least one of the tension member and/or the plurality of additional tension members to cause volumetric compression of the volumetric region. In various embodiments, an additional predetermined volumetric region encompasses at least another portion of the tumor, and wherein the passing further includes deploying a plurality of windings around the additional volumetric region. In some embodiments, the tightening comprises tightening the tension member and/or the plurality of additional tension members to collectively apply compressive force toward an interior of the tumor. In some embodiments, the compressive force is radially compressive force applied toward a center of the tumor.

In various embodiments, the volumetric region encompasses a majority of a volume of the tumor.

In various embodiments, the volumetric region encompasses an entirety of the volume of the tumor.

In various embodiments, the tightening is performed using a tightening apparatus, and the method further comprises: removing the tightening apparatus from the body before and/or during the maintaining the increased pressure.

In various embodiments, the compression is maintained continuously at least until achieving necrosis in at least a majority of all tissues of the tumor. In various embodiments, the compression is maintained continuously at least until achieving necrosis in substantially all tissues of the tumor.

In various embodiments, the compression is maintained continuously for a period of no less than 1 hour, or no less than four hours. In some embodiments, the compression is maintained continuously for a period of no less than eight hours. In some embodiments, the compression is maintained continuously for a period of no less than 24 hours. In some embodiments, the compression is maintained continuously for a period of no less than three days.

In various embodiments, the tightening causes increase in capillary blood pressure in a region that is downstream relative to blood vessels feeding the tumor, thereby diminishing or preventing transfer of oxygenated blood from the blood vessels to tissues of the tumor and causing the ischemia.

In various embodiments, the tightening causes increase in interstitial fluid pressure in the tumor and/or in tissues of the organ surrounding the tissue, thereby diminishing or preventing transfer of cell nutrients and small molecules into the tumor.

In various embodiments, the tightening the tension member increases the pressure within the tumor to a first level and injures tissue within the volumetric region, and the method further comprises: maintaining the tension member in a tightened state while tissue within the volumetric region that has been injured swells in response to the injury, wherein swelling of the tissue within the volumetric region increases the pressure within the tumor to a second level that exceeds the first level. In various embodiments, the swelling of the tissue within the volumetric region occurs by natural bodily processes in response to the injury such that increasing the pressure within the tumor to the second level is an indirect result of the tightening the tension member.

In various embodiments, the method further comprises passing the tension member along a predetermined passage line between the entry opening and the exit opening. In some embodiments, the passage line projects across one or more blood vessels feeding the tumor, such that the tightening of the tension member directly causes occlusion of the one or more blood vessels.

In various embodiments, the tumor is intramural, subserous or submucosal with respect to the organ.

In various embodiments, at least a portion of the tumor is situated intramurally within the organ, and wherein passing the tension member within the organ comprises passing the tension member through an intramural portion of the organ. In some embodiments, the passing the tension member through the intramural portion of the organ comprises passing the tension member around the at least a portion of the tumor that is situated intramurally within the organ. In some embodiments, the passing the tension member within the organ comprises passing the tension member exclusively through the intramural portion of the organ and/or the tumor between the entry opening and the exit opening. In some embodiments, the passing the tension member within the organ comprises passing the tension member exclusively through the intramural portion of the organ and/or the tumor between the entry opening and the exit opening.

In various embodiments, the tumor is a uterine fibroid.

In various embodiments, the method further comprises creating a surgical access to the organ from outside the body, wherein at least one of the passing, tightening, and maintaining is performed via the surgical access.

In various embodiments, the method further comprises performing open surgery to provide access to the organ.

In various embodiments, the tightening includes or is followed by securing a first portion of the tension member protruding from the entry opening to a second portion of the tension member protruding from the exit opening, wherein the securing facilitates the maintaining. In some embodiments, the securing is performed outside boundaries of the organ. In some embodiments, the tightening and the securing are performed using a tightening device. In some embodiments, the tightening device is removed from the body prior to or during the maintaining. In some embodiments, the securing comprises attaching a fastener to the tension member. In some embodiments, the securing comprises crimping the fastener to securely grasp the tension member. In some embodiments, the method further comprises: creating a surgical access to the organ from outside the body, wherein at least one of the passing, tightening, and maintaining is performed via the surgical access; and closing the surgical access while the tension member and the fastener remain within the body of the subject. In some embodiments, the tension member comprises a bioresorbable material and the fastener comprises a non-bioresorbable material, and the method further comprises: leaving the tension member within the body of the subject for a time sufficient to permit the body to resorb the tension member; and leaving the fastener within the body of the subject beyond the time sufficient to permit the body to resorb the tension member.

In various embodiments, passing the tension member comprises advancing an end of the tension member through the exit opening, around the tumor, and through the entry opening such that a first portion of the tension member protrudes from the organ through the exit opening and a second portion of the tension member protrudes from the organ through the entry opening. In some embodiments, the method further comprises securing the first portion of the tension member to the second portion of the tension member. In some embodiments, the method further comprises: advancing an elongated member through the entry opening, around the tumor, and through the exit opening; and coupling the elongated member to the tension member prior to the passing the tension member, wherein the passing the tension member comprises withdrawing the elongated member through the exit opening, around the tumor, and through the entry opening while coupled to the tension member.

In various embodiments, the method further comprises: forming a passage around the volumetric region between the entry and exit openings, wherein the passing is performed after the forming and mostly or entirely within the passage. In some embodiments, the passing includes pulling the tension member towards the entry opening. In some embodiments, the forming includes advancing a curved needle around the volumetric region. In some embodiments, the forming further includes: positioning an outer tube through the entry opening into the organ, in proximity to the tumor, wherein the advancing the curved needle comprises advancing the needle through a lumen of the outer tube. In some embodiments, the positioning includes creating the entry opening with a distal end of the outer tube. In some embodiments, the positioning includes placing a distal end of the outer tube adjacent to a transverse extremity of the tumor.

In various embodiments, the entry opening is located at a first location on or adjacent to the tumor and the exit opening is located at a second location on or adjacent to the tumor spaced from the first location, such that the tumor is located between the entry and exit openings.

In various embodiments, the tension member comprises a wire. In some embodiments, the wire comprises a suture wire.

In various embodiments, the tension member comprises a flexible strip.

In various embodiments, the tension member includes at least one of implant-grade metal alloy, implant-grade polymer, implant-grade textile, and biodegradable material.

In various embodiments, the tension member is configured with a yield strength or a maximal tension force of at least 25 newtons.

In various embodiments, the passing comprises encompassing more than half a circumference of the tumor with the tension member.

In various embodiments, the tightening comprises tightening the tension member to achieve a chosen tensioning force. In some embodiments, the chosen tensioning force is predetermined.

In various embodiments, the method further comprising measuring a tensioning force applied to the tension member during the tightening.

In some embodiments, the method further comprising measuring the pressure within the tumor during the tightening.

In various embodiments, the volumetric region comprises a portion of the surface of the organ. In some embodiments, the method further comprising extending the tension member over the portion of the surface of the organ between the entry opening and the exit opening, wherein the tightening the tension member comprises tightening the tension member around the portion of the surface of the organ. In some embodiments, the volumetric region comprises an entirety of the tumor.

In some embodiments, one or more of the passing the tension member and the tightening the tension member is performed via a robotic system.

Example 2

A method for treating a tumor within a body of a subject can comprise: deploying a plurality of windings of at least one tension member around the tumor, at least a portion of each of the windings being spaced apart from a portion of each adjacent winding; tightening the at least one tension member such that the plurality of windings collectively causes volumetric compression of the tumor; and maintaining the volumetric compression continuously to achieve ischemia in most or all tissues of the tumor.

In various embodiments, the tightening comprises tightening the at least one tension member to achieve a chosen tension force within the tumor. In some embodiments, the tightening further comprises tightening the at least one tension member to achieve a chosen pressure within the tumor.

In various embodiments, the tightening comprises tightening the at least one tension member to achieve a chosen pressure within the tumor.

In various embodiments, the tightening comprises tightening the at least one tension member such that each of the plurality of windings applies compressive force toward an interior of the tumor. In some embodiments, the compressive force is applied radially toward a center of the tumor.

Example 3

A method for treating a tumor within a body of a subject can comprise: forming a surgical access into the body in proximity to an organ that surrounds the tumor; via the surgical access, advancing an outer tube into the organ via an entry opening at a surface of the organ, thereby forming a passage with a distal end of the outer tube from the entry opening to a first point adjacent to a transverse extremity of the tumor; pushing a pre-curved needle through a lumen of the outer tube while the needle is in a straightened state until a distal portion of the pre-curved needle protrudes from the outer tube; further pushing the pre-curved needle past the distal end of the outer tube to permit the needle to elastically regain a curved shape and to extend the passage along a curved path from the first point to a second point around a volumetric region that encompasses at least a portion of the tumor, relative to the first point; creating an exit point at the surface of the organ in proximity to the second point; passing a tension member mostly or entirely within the passage resulting with a first portion of the tension member protruding from the organ via the entry opening and a second portion of the tension member protruding from the organ via the exit opening; tightening the tension member so as to achieve volumetric compression of the volumetric region for increasing pressure within the tumor; and securing the first portion to the second portion of the tension member; wherein the tightening is maintained after the securing to achieve ischemic in most or all tissues of the tumor.

In various embodiments, the securing comprises coupling a fastener to the first and second portions of the tension member to maintain the tension member in a tightened state. In some embodiments, the fastener comprises a ductile material, and wherein the securing comprises crimping the fastener around the first portion and the second portion of the tension member.

In various embodiments, the creating includes advancing a stylet via a lumen of the pre-curved needle until a distal end of the stylet penetrates through the surface of the organ, thereby creating the exit opening and extending the passage from the second point to the exit opening. In some embodiments, the passing includes pulling the tension member through the passage from the exit opening to the entry opening using the stylet, wherein the stylet has an anchoring member at the distal end thereof configured for facilitating selective anchoring to the tension member.

Example 4

A method can comprise: circumscribing a tumor with at least one tension member along a first path; circumscribing the tumor with the at least one tension member along a second path different from the first path; tightening the at least one tension member to compress the tumor along the first and second paths to increase capillary blood pressure and/or an interstitial fluid pressure within the tumor above a threshold level that is sufficient to cause ischemia of the tumor; and maintaining the capillary blood pressure and/or the interstitial pressure above the threshold level via the at least one tension member for a period sufficient to permit at least a portion of the tumor to necrotize due to the ischemia.

In various embodiments, the at least one tension member comprises a single tension member looped around the tumor along the first and second paths.

In various embodiments, the at least one tension member comprises a first tension member and a second tension member, wherein the circumscribing along the first path comprises circumscribing the tumor with the first tension member along the first path, and wherein the circumscribing along the second path comprises circumscribing the tumor with the second tension member along the second path.

In various embodiments, the first path defines a first plane that extends through the tumor and the second path defines a second plane that extends through the tumor, the second plane being at an angle relative to the first plane. In some embodiments, the angle is no less than 30 degrees. In some embodiments, the first and second planes intersect along a line that extends through the tumor. In some embodiments, the line extends through the center of the tumor.

In various embodiments, the tightening comprises tightening the at least one tension member to collectively apply compressive force toward an interior of the tumor along the first and second paths. In some embodiments, the compressive force is radially compressive force applied toward a center of the tumor.

In various embodiments, the threshold level of the interstitial fluid pressure is no less than 1 mmHg, or no less than 2 mmHg, or no less than 4 mmHg.

In various embodiments, the threshold level of the capillary blood pressure is no less than 10 mmHg, or no less than 20 mmHg, or no less than 25 mmHg.

In various embodiments, the period sufficient to permit at least a portion of the tumor to necrotize due to the ischemia is no less than four hours.

In various embodiments, each circumscribing step comprises advancing the at least one tension member around the tumor at an exterior of a pseudo-capsule that surrounds the tumor.

In various embodiments, the method further comprises forming the first path by inserting a tubular member into a patient until a distal end of the tubular member is in proximity to the tumor, and advancing a needle past the distal end of the tubular member along a curved path that extends about at least a portion of the tumor. In some embodiments, the needle is pre-curved, and the method further comprises: retaining the needle in a straightened configuration when the needle is within the tubular member; and advancing the needle past the distal end of the tubular member to permit the needle to resiliently return to a curved configuration and form a curved path around at least a portion of the tumor. In some embodiments, circumscribing the tumor with the at least one tension member along the first path comprises: coupling a stylet to the at least one tension member; and passing the stylet along the first path while coupled to the at least one tension member.

Example 5

A method can comprise: volumetrically compressing a tumor within a patient to increase a pressure within the tumor above a threshold level that is sufficient to cause ischemia of the tumor; and maintaining the pressure above the threshold level for a period sufficient to permit at least a portion of the tumor to necrotize due to the ischemia.

In various embodiments, the volumetrically compressing the tumor comprises volumetrically compressing only a portion of the tumor.

In various embodiments, the method further comprises circumscribing the tumor with at least one device of foreign origin relative to the patient, wherein the volumetrically compressing the tumor and maintaining the pressure above the threshold level are achieved via the at least one device. In some embodiments, volumetrically compressing the tumor is achieved solely by reducing a profile of the device around the tumor. In some embodiments, maintaining the pressure above the threshold level is achieved solely by maintaining a reduced profile of the device around the tumor. In some embodiments, volumetrically compressing the tumor comprises reducing a profile of the device around the tumor, and maintaining the pressure above the threshold level is achieved solely by reducing a profile of the device around the tumor. In some embodiments, the device comprises at least one tension line. In some embodiments, the device comprises a mesh that comprises the at least one tension line.

In various embodiments, the volumetrically compressing comprises compressing the tumor along at least first and second lines of compression that extend around an outer surface of the tumor along different paths. In some embodiments, the first and second lines of compression are nonintersecting. In some embodiments, the first and second lines of compression cross at an intersection point. In some embodiments, the first and second lines of compression cross at no fewer than two spaced-apart intersection points. In some embodiments, the method further comprises encompassing the tumor with at least one tension member to define a three-dimensional shape around the tumor, wherein the volumetrically compressing the tumor comprises decreasing a size of the three-dimensional shape. In some embodiments, decreasing the size of the three-dimensional shape is achieved by tightening the at least one tension member. In some embodiments, the three-dimensional shape comprises a plurality of loops. In some embodiments, at least one of the loops overlaps another of the loops. In some embodiments, the loops cross at one or more points of intersection. In some embodiments, the loops define planes that are angularly offset from one another. In some embodiments, the planes intersect along a line that passes through the tumor. In some embodiments, each of the loops is substantially circular. In some embodiments, the three-dimensional shape comprises a spiral that extends along a length of the tumor and that extends through an angular rotation of no less than 360 degrees.

In various embodiments, the method further comprises passing a tension member through the tumor, wherein the volumetrically compressing the tumor is achieved via the tension member.

In various embodiments, the volumetrically compressing the tumor comprises continuously applying compressive force toward an interior of the tumor. In some embodiments, the compressive force comprises radially compressive force applied toward a center of the tumor.

In various embodiments, the threshold level of the pressure is no less than 10 mmHG, or no less than 20 mmHg, or no less than 50 mmHg, or no less than 75 mmHg, or no less than 100 mmHg.

Example 6

A method can comprise: passing a tension member through an intramural portion of an organ and around a tumor that is at least partially positioned in the intramural portion of the organ; tightening the tension member with a chosen tightening force to cause compression of the tumor, thereby directly increasing pressure within the tumor sufficient to achieve ischemia of the tumor; and maintaining the increased pressure continuously until most or all tissues of the tumor undergo necrosis resulting from the ischemia.

Example 7

A method can comprise: placing a medical device around a tumor such that the medical device defines a three-dimensional shape that encompasses the tumor; transitioning the medical device to a reduced profile to decrease a size of the three-dimensional shape and thereby achieve volumetric compression of the tumor in an amount sufficient to achieve ischemia of the tumor; and maintaining the medical device in the reduced profile until the ischemia causes necrosis of at least a portion of the tumor.

In various embodiments, the transitioning the medical device to the reduced profile increases pressure within the tumor to achieve the ischemia of the tumor.

In various embodiments, the medical device comprises one or more tension members. In some embodiments, the device comprises a plurality of tension members, wherein the placing the medical device around the tumor comprises advancing each tension member around the tumor sequentially, and wherein the transitioning the medical device to the reduced profile comprises tightening each tension member. In some embodiments, each tension member is placed around the tumor and tightened prior to the placing and the tightening of a subsequent tension member. In some embodiments, the medical device further comprises one or more anchors coupled to the one or more tension members.

In various embodiments, the increased pressure is maintained continuously until the ischemia causes necrosis of at least a majority of the tumor.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A method for treating a tumor that is at least partially embedded within healthy tissue of an organ of a body of a subject, the method comprising:
    defining a volumetric region internal to the organ in which the tumor is embedded, wherein the defined volumetric region contains at least a portion of the tumor;
    passing at least one tension member along a trajectory within the organ between an entry opening and an exit opening, each opening being at a surface of the organ, wherein the trajectory is in close fit around the defined volumetric region;
    tightening the at least one tension member to cause compression of the defined volumetric region, thereby directly increasing a pressure within the tumor; and
    maintaining the increased pressure such that most or all tissues of the tumor undergo ischemia resulting directly from the compression caused by the tightened at least one tension member.

2. The method according to claim 1, wherein the passing comprises winding the at least one tension member along a plurality of different trajectories around the volumetric region.

3. The method according to claim 2, wherein the tightening includes directly causing a volumetric compression of the volumetric region.

4. The method according to claim 1, wherein the volumetric region encompasses a majority or entirety of a volume of the tumor.

5. The method according to claim 1, wherein the compression is maintained continuously at least until achieving necrosis in substantially all tissues of the tumor.

6. The method according to claim 1, wherein the compression is maintained continuously for a period of no less than 1 hour.

7. The method according to claim 1, wherein the tightening the at least one tension member increases the pressure within the tumor to a first level and injures tissue within the volumetric region, the method further comprising:
    maintaining the at least one tension member in a tightened state while tissue within the volumetric region that has been injured swells in response to the injury, wherein swelling of the tissue within the volumetric region increases the pressure within the tumor to a second level that exceeds the first level.

8. The method according to claim 1, wherein the passing comprises passing the at least one tension member along a predetermined passage line between the entry opening and the exit opening.

9. The method according to claim 8, wherein the passage line projects across one or more blood vessels feeding the tumor, such that the tightening of the at least one tension member directly causes occlusion of the one or more blood vessels.

10. The method according to claim 1, wherein at least a portion of the tumor is situated intramurally within the organ, and wherein the passing the at least one tension member within the organ comprises passing the at least one tension member through an intramural portion of the organ.

11. The method according to claim 1, wherein the tumor is a uterine fibroid.

12. The method according to claim 1, further comprising creating a surgical access to the organ from outside the body, wherein at least one of the passing, tightening, and maintaining is performed via the surgical access.

13. The method according to claim 12, further comprising closing the surgical access while the at least one tension member remains within the body of the subject.

14. The method according to claim 1, wherein the at least one tension member includes a first portion protruding from the entry opening and a second portion protruding from the exit opening, wherein the tightening includes or is followed by securing the first portion to the second portion, and wherein the securing facilitates the maintaining.

15. The method according to claim 14, wherein the securing is performed outside boundaries of the organ.

16. The method according to claim 14, wherein the securing comprises attaching a at least one fastener to the at least one tension member.

17. The method according to claim 16, wherein the securing comprises crimping the at least one fastener to securely grasp the at least one tension member.

18. The method according to claim 1, wherein the passing the at least one tension member comprises passing an end of the at least one tension member through the exit opening, around the tumor, and through the entry opening such that a first portion of the at least one tension member protrudes from the organ through the exit opening and a second portion of the at least one tension member protrudes from the organ through the entry opening.

19. The method according to claim 18, further comprising:
- advancing an elongated member through the entry opening, around the tumor, and through the exit opening; and
- coupling the elongated member to the at least one tension member prior to the passing the at least one tension member, and
- withdrawing the elongated member with the at least one tension member coupled thereto through the exit opening, around the tumor, and through the entry opening.

20. The method according to claim 18, wherein the passing comprises:
- forming a passage around the volumetric region between the entry opening and the exit opening, wherein the sequentially passing is performed after the forming and mostly or entirely within the passage.

21. The method according to claim 1, wherein the entry opening is located at a first location on or adjacent to the tumor and the exit opening is located at a second location on or adjacent to the tumor spaced from the first location, such that the tumor is located between the entry and exit openings.

22. The method according to claim 1, wherein the at least one tension member comprises a suture wire.

23. The method according to claim 1, wherein the tightening comprises tightening the at least one tension member to collectively apply compressive force toward an interior of the tumor.

24. The method according to claim 1, wherein the tightening comprises tightening the at least one tension member to achieve a chosen tensioning force in the at least one tension member.

25. The method according to claim 1, further comprising measuring a tensioning force applied to the at least one tension member, and/or measuring the pressure within the tumor, during the tightening.

26. A method for treating a tumor within a body of a subject, the method comprising:
- deploying a plurality of windings of at least one tension member around the tumor, at least a portion of each of the windings being spaced apart from a portion of each adjacent winding of the windings such that the windings define a three-dimensional shape around the tumor;
- tightening the at least one tension member to cause a volumetric compression of the tumor; and
- maintaining the volumetric compression continuously to achieve ischemia in most or all tissues of the tumor.

27. A method according to claim 26, wherein the tightening comprises tightening the at least one tension member to achieve a chosen tension force within the tumor and/or to achieve a chosen pressure within the tumor.

28. The method according to claim 26, wherein the tightening comprises tightening the at least one tension member such that each of the plurality of windings applies compressive force toward an interior of the tumor.

* * * * *